(12) United States Patent
Watterson et al.

(10) Patent No.: US 8,354,398 B2
(45) Date of Patent: Jan. 15, 2013

(54) SUBSTITUTED ISOXAZOLE COMPOUNDS

(75) Inventors: Scott Hunter Watterson, Pennington, NJ (US); Alaric J. Dyckman, Lawrenceville, NJ (US); William J. Pitts, Newtown, PA (US); Steven H. Spergel, Warrington, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 13/145,730

(22) PCT Filed: Jan. 22, 2010

(86) PCT No.: PCT/US2010/021693
§ 371 (c)(1),
(2), (4) Date: Jul. 21, 2011

(87) PCT Pub. No.: WO2010/085581
PCT Pub. Date: Jul. 29, 2010

(65) Prior Publication Data
US 2011/0300165 A1    Dec. 8, 2011

Related U.S. Application Data

(60) Provisional application No. 61/146,827, filed on Jan. 23, 2009.

(51) Int. Cl.
*A61K 31/4245*    (2006.01)
*C07D 413/14*    (2006.01)
(52) U.S. Cl. .................. 514/210.18; 548/131
(58) Field of Classification Search ............. 514/210.18; 548/131
See application file for complete search history.

(56) References Cited

U.S. PATENT DOCUMENTS

| | | |
|---|---|---|
| 7,199,142 B2 | 4/2007 | Chen |
| 7,220,734 B2 | 5/2007 | Doherty |
| 7,309,721 B2 | 12/2007 | Budhu |
| 2005/0033055 A1 | 2/2005 | Bugianesi et al. |
| 2005/0070506 A1 | 3/2005 | Doherty et al. |
| 2006/0173000 A1 | 8/2006 | Kesteleyn et al. |
| 2007/0203100 A1 | 8/2007 | Pan et al. |
| 2008/0200535 A1 | 8/2008 | Ohmori et al. |
| 2008/0249093 A1 | 10/2008 | Colandrea et al. |
| 2008/0280876 A1 | 11/2008 | Hobson et al. |
| 2010/0160369 A1 | 6/2010 | Canne et al. |

FOREIGN PATENT DOCUMENTS

| | | |
|---|---|---|
| WO | WO 03/062248 | 7/2003 |
| WO | WO 03/062252 | 7/2003 |
| WO | WO 03/105771 | 12/2003 |
| WO | WO 2004/046143 | 6/2004 |
| WO | WO 2005/000833 | 1/2005 |
| WO | WO 2006/047195 | 5/2006 |
| WO | WO 2006/088944 | 8/2006 |
| WO | WO 2006/100631 | 9/2006 |
| WO | WO 2006/100633 | 9/2006 |
| WO | WO 2006/115188 | 11/2006 |
| WO | WO 2006/131336 | 12/2006 |
| WO | WO 2007/024922 | 3/2007 |
| WO | WO 2007/061458 | 5/2007 |
| WO | WO 2007/085451 | 8/2007 |
| WO | WO 2007/109334 | 9/2007 |
| WO | WO 2007/116866 | 10/2007 |
| WO | WO 2008/029306 | 3/2008 |
| WO | WO 2008/029371 | 3/2008 |
| WO | WO 2008/035239 | 3/2008 |
| WO | WO 2008/074820 | 6/2008 |
| WO | WO 2008/079382 | 7/2008 |
| WO | WO 2008/141731 | 11/2008 |
| WO | WO 2009/011850 | 1/2009 |
| WO | WO 2009/043889 | 4/2009 |
| WO | WO 2009/043890 | 4/2009 |
| WO | WO 2009/057079 | 5/2009 |
| WO | WO 2009/131090 | 10/2009 |
| WO | WO 2009/151529 | 12/2009 |
| WO | WO 2010/039237 | 4/2010 |
| WO | WO 2010/039238 | 4/2010 |
| WO | WO 2010/085582 | 7/2010 |
| WO | WO 2010/085584 | 7/2010 |

OTHER PUBLICATIONS

U.S. Appl. No. 13/145,721, filed Jul. 21, 2011, William J. Pitts.

(Continued)

*Primary Examiner* — Rebecca Anderson
*Assistant Examiner* — Matthew Coughlin
(74) *Attorney, Agent, or Firm* — Gary D. Greenblatt

(57) ABSTRACT

Disclosed are compounds of Formula (I)

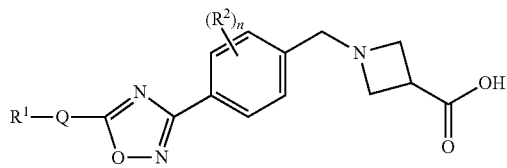

(I)

or pharmaceutically acceptable salts thereof, wherein Q is

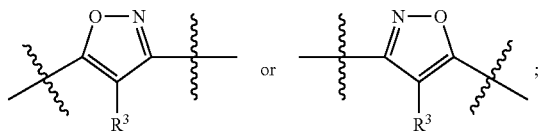

$R^1$ is alkyl or aryl, said aryl optionally substituted with one to five substituents independently selected from $C_1$ to $C_6$ alkyl, $C_1$ to $C_4$ haloalkyl, —$OR^4$, and/or halogen; and $R^2$, $R^3$, $R^4$, and n are defined herein.

Also disclosed are methods of using such compounds as selective agonists for G protein-coupled receptor $S1P_1$, and pharmaceutical compositions comprising such compounds. These compounds are useful in treating, preventing, or slowing the progression of diseases or disorders in a variety of therapeutic areas, such as autoimmune diseases and vascular disease.

12 Claims, No Drawings

OTHER PUBLICATIONS

U.S. Appl. No. 13/145,728, filed Jul. 21, 2011, Alaric J. Dyckman.
IPER/Search report for PCT/US2010/021693 issued Jul. 26, 2011.
Anliker et al., J. Biol. Chem., 279:20555 (2004).
Brinkman et al., Am. J. Transplant., 4:1019 (2004).
Brinkman et al., J. Biol. Chem., 277:21453 (2002).
Kenji Chiba, Pharmacology & Therapeutics, 108:308 (2005).
Fujino et al., J. Pharmacol. and Exp. Ther., 305:70 (2003).
Hale et al., J. Med. Chem. 47:6662 (2004).
Hale et al., Bioorg. Med. Chem. Lett., 14:3501 (2004).
Kahan et al., Transplantation, 76:1079 (2003).
Kappos et al., N. Engl. J. Med., 355:1124 (2006).
Koyrakh et al., Am. J. Transplant., 5:529 (2005).
Forrest et al., J. Pharmacol. Exp. Ther., 309:758 (2004).
Mandala et al., Science, 296:346 (2002).
Morris et al., Eur. J. Immunol., 35:3570 (2005).
Sanna et al., J. Biol. Chem., 279:13839 (2004).
Webb et al., J. Neuroimmunol., 153:108 (2004).

SUBSTITUTED ISOXAZOLE COMPOUNDS

The present invention generally relates to substituted isoxazole compounds useful as $S1P_1$ agonists. Provided herein are substituted isoxazole compounds, compositions comprising such compounds, and methods of their use. The invention further pertains to pharmaceutical compositions comprising at least one compound according to the invention that are useful for the treatment of conditions related to $S1P_1$ agonism, such as autoimmune diseases and vascular disease.

Sphingosine-1-phosphate (S1P) has been demonstrated to induce many cellular effects, including those that result in platelet aggregation, cell proliferation, cell morphology, tumor cell invasion, endothelial cell and leukocyte chemotaxis, endothelial cell in vitro angiogenesis, and lymphocyte trafficking. S1P receptors are therefore good targets for a wide variety of therapeutic applications such as tumor growth inhibition, vascular disease, and autoimmune diseases. S1P signals cells in part via a set of G protein-coupled receptors named $S1P_1$ or S1P1, $S1P_2$ or S1P2, $S1P_3$ or S1P3, $S1P_4$ or S1P4, and $S1P_5$ or S1P5 (formerly called EDG-1, EDG-5, EDG-3, EDG-6, and EDG-8, respectively).

S1P is important in the entire human body as it is also a major regulator of the vascular and immune systems. In the vascular system, S1P regulates angiogenesis, vascular stability, and permeability. In the immune system, S1P is recognized as a major regulator of trafficking of T- and B-cells. S1P interaction with its receptor $S1P_1$ is needed for the egress of immune cells from the lymphoid organs (such as thymus and lymph nodes) into the lymphatic vessels. Therefore, modulation of S1P receptors was shown to be critical for immunomodulation, and S1P receptor modulators are novel immunosuppressive agents.

The $S1P_1$ receptor is expressed in a number of tissues. It is the predominant family member expressed on lymphocytes and plays an important role in lymphocyte trafficking. Down-regulation of the $S1P_1$ receptor disrupts lymphocyte migration and homing to various tissues. This results in sequestration of the lymphocytes in lymph organs thereby decreasing the number of circulating lymphocytes that are capable of migration to the affected tissues. Thus, development of an $S1P_1$ receptor agent that suppresses lymphocyte migration to the target sites associated with autoimmune and aberrant inflammatory processes could be efficacious in a number of autoimmune and inflammatory disease states.

Among the five S1P receptors, $S1P_1$ has a widespread distribution and is highly abundant on endothelial cells where it works in concert with $S1P_3$ to regulate cell migration, differentiation, and barrier function. Inhibition of lymphocyte recirculation by non-selective S1P receptor modulation produces clinical immunosuppression preventing transplant rejection, but such modulation also results in transient bradycardia. Studies have shown that $S1P_1$ activity is significantly correlated with depletion of circulating lymphocytes. In contrast, $S1P_3$ receptor agonism is not required for efficacy. Instead, $S1P_3$ activity plays a significant role in the observed acute toxicity of nonselective S1P receptor agonists, resulting in the undesirable cardiovascular effects, such as bradycardia and hypertension. (See, e.g., Hale et al., Bioorg. Med. Chem. Lett., 14:3501 (2004); Sanna et al., J. Biol. Chem., 279:13839 (2004); Anliker et al., J. Biol. Chem., 279:20555 (2004); Mandala et al., J. Pharmacol. Exp. Ther., 309:758 (2004).)

An example of an $S1P_1$ agonist is FTY720. This immunosuppressive compound FTY720 (JPI 1080026-A) has been shown to reduce circulating lymphocytes in animals and humans, and to have disease modulating activity in animal models of organ rejection and immune disorders. The use of FTY720 in humans has been effective in reducing the rate of organ rejection in human renal transplantation and increasing the remission rates in relapsing remitting multiple sclerosis (see Brinkman et al., J. Biol. Chem., 277:21453 (2002); Mandala et al., Science, 296:346 (2002); Fujino et al., J. Pharmacol. and Exp. Ther., 305:45658 (2003); Brinkman et al., Am. J. Transplant., 4:1019 (2004); Webb et al., J. Neuroimmunol., 153:108 (2004); Morris et al., Eur. J. Immunol., 35:3570 (2005); Chiba, Pharmacology & Therapeutics, 108:308 (2005); Kahan et al., Transplantation, 76:1079 (2003); and Kappos et al., N. Engl. J. Med., 335:1124 (2006)). Subsequent to its discovery, it has been established that FTY720 is a prodrug, which is phosphorylated in vivo by sphingosine kinases to a more biologically active agent that has agonist activity at the $S1P_1$, $S1P_3$, $S1P_4$, and $S1P_5$ receptors. It is this activity on the S1P family of receptors that is largely responsible for the pharmacological effects of FTY720 in animals and humans.

Clinical studies have demonstrated that treatment with FTY720 results in bradycardia in the first 24 hours of treatment (Kappos et al., N. Engl. J. Med., 335:1124 (2006)). The observed bradycardia is commonly thought to be due to agonism at the $S1P_3$ receptor. This conclusion is based on a number of cell based and animal experiments. These include the use of $S1P_3$ knockout animals which, unlike wild type mice, do not demonstrate bradycardia following FTY720 administration and the use of $S1P_1$ selective compounds. (Hale et al., Bioorg. Med. Chem. Lett., 14:3501 (2004); Sanna et al., J. Biol. Chem., 279:13839 (2004); and Koyrakh et al., Am. J. Transplant., 5:529 (2005)).

The following applications have described compounds as $S1P_1$ agonists: WO 03/061567 (U.S. Publication No. 2005/0070506), WO 03/062248 (U.S. Pat. No. 7,351,725), WO 03/062252 (U.S. Publication No. 2005/0033055), WO 03/073986 (U.S. Pat. No. 7,309,721), WO 03/105771, WO 05/058848, WO 06/047195, WO 06/100633, WO 06/115188, WO 06/131336, WO 2007/024922, WO 07/116,866, WO 08/023,783 (U.S. Publication No. 2008/0200535), and WO 08/074,820. Also see Hale et al., J. Med. Chem., 47:6662 (2004).

There still remains a need for compounds useful as $S1P_1$ agonists and yet having selectivity over $S1P_3$.

Applicants have found potent compounds that have activity as $S1P_1$ agonists. Further, applicants have found compounds that have activity as $S1P_1$ agonists and are selective over $S1P_3$. These compounds are provided to be useful as pharmaceuticals with desirable stability, bioavailability, therapeutic index, and toxicity values that are important to their drugability.

SUMMARY OF THE INVENTION

The present invention fills the foregoing need by providing compounds of Formula (I):

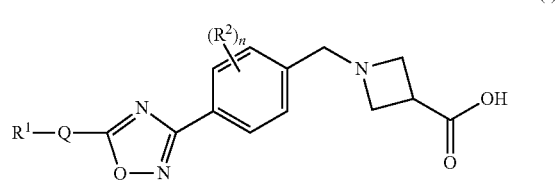

or pharmaceutically acceptable salts thereof, wherein:
Q is

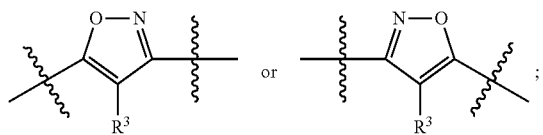

n is zero or an integer selected from 1 through 4;
R$^1$ is alkyl or aryl, said aryl optionally substituted with one to five substituents independently selected from C$_1$ to C$_6$ alkyl, C$_1$ to C$_4$ haloalkyl, —OR$^4$, and/or halogen;
each R$^2$ is independently selected from C$_1$ to C$_6$ alkyl, C$_1$ to C$_4$ haloalkyl, —OR$^4$, and/or halogen;
R$^3$ is hydrogen, alkyl, cycloalkyl, haloalkyl, —C(O)OR$^5$, —C(O)NR$_a$R$_b$, or aryl, said aryl optionally substituted with one to five substituents independently selected from C$_1$ to C$_6$ alkyl, C$_1$ to C$_4$ haloalkyl, —OR$^4$, and/or halogen;
each R$^4$ is independently selected from C$_1$ to C$_6$ alkyl, C$_1$ to C$_4$ haloalkyl, and/or benzyl;
R$^5$ is hydrogen, alkyl, or benzyl; and
R$_a$ and R$_b$ are independently selected from hydrogen, alkyl, haloalkyl, and/or benzyl.

Also described are pharmaceutical compositions comprising a compound of Formula (I), or a pharmaceutically acceptable salt thereof; and a pharmaceutically acceptable carrier.

Further described is a method of treating a disease or disorder associated with the activity of G protein-coupled receptor S1P$_1$, the method comprising administering to a mammalian patient a compound of Formula (I) or a pharmaceutically acceptable salt thereof.

The compounds of Formula (I) and compositions comprising the compounds are S1P$_1$ agonists, which are selective for S1P$_1$ activity over S1P$_3$ activity. The compounds of Formula (I) and compositions comprising said compounds may be used in treating, preventing or curing various S1P$_1$ receptor-related conditions while reducing or minimizing the side effects due to S1P$_3$ activity. Pharmaceutical compositions comprising these compounds are useful in treating, preventing, or slowing the progression of diseases or disorders in a variety of therapeutic areas, such as autoimmune and vascular diseases.

DETAILED DESCRIPTION

One embodiment provides a compound of Formula (I), (I)

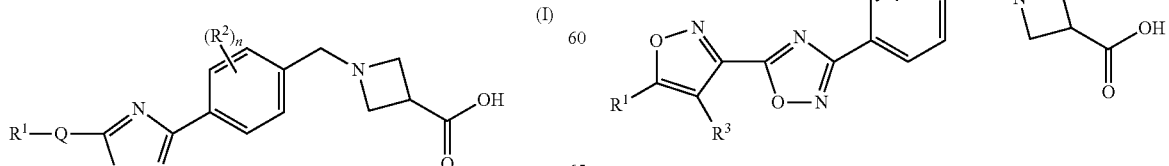

or a pharmaceutically acceptable salt thereof, wherein:
Q is

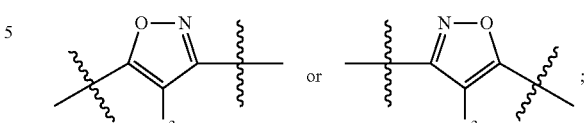

n is zero or an integer selected from 1 through 4;
R$^1$ is alkyl or aryl, said aryl optionally substituted with one to five substituents independently selected from C$_1$ to C$_6$ alkyl, C$_1$ to C$_4$ haloalkyl, —OR$^4$, and/or halogen;
each R$^2$ is independently selected from C$_1$ to C$_6$ alkyl, C$_1$ to C$_4$ haloalkyl, —OR$^4$, and/or halogen;
R$^3$ is hydrogen, alkyl, cycloalkyl, haloalkyl, —C(O)OR$^5$, —C(O)NR$_a$R$_b$, or aryl, said aryl optionally substituted with one to five substituents independently selected from C$_1$ to C$_6$ alkyl, C$_1$ to C$_4$ haloalkyl, —OR$^4$, and/or halogen;
each R$^4$ is independently selected from C$_1$ to C$_6$ alkyl, C$_1$ to C$_4$ haloalkyl, and/or benzyl;
R$^5$ is hydrogen, alkyl, or benzyl; and
R$_a$ and R$_b$ are independently selected from hydrogen, alkyl, haloalkyl, and/or benzyl.

One embodiment provides a compound of Formula (I) or a pharmaceutically acceptable salt thereof, wherein:
Q is

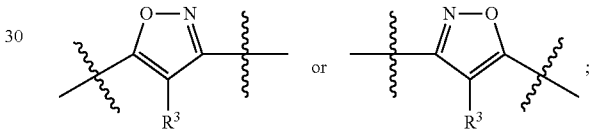

n is zero or 1;
R$^1$ is propyl, butyl, or phenyl;
R$^2$ is F, Cl, Br, —CH$_3$, or —CF$_3$; and
R$^3$ is C$_2$-C$_4$alkyl, —C$_1$-C$_3$fluoroalkyl, cyclopropyl, —C(O)OH, —C(O)OCH$_3$, —C(O)NHCH$_3$, —C(O)NH(CH$_2$CF$_3$), or phenyl.

One embodiment provides a compound of Formula (I) or a pharmaceutically acceptable salt thereof, wherein:
Q is

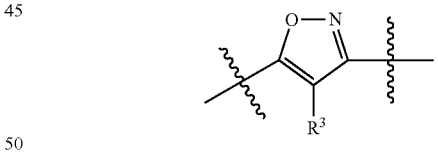.

A compound of this embodiment has the structure represented by Formula (Ia):

(Ia)

or a pharmaceutically acceptable salt thereof, wherein R$^1$, R$^2$, R$^3$, and n are as defined hereinabove.

One embodiment provides a compound of Formula (I) or a pharmaceutically acceptable salt thereof, wherein:
Q is

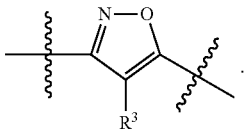

A compound of this embodiment has the structure represented by Formula (Ia):

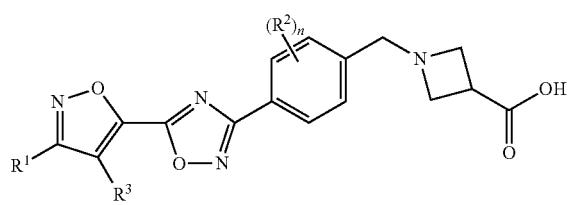

(Ib)

or a pharmaceutically acceptable salt thereof, wherein $R^1$, $R^2$, $R^3$, and n are as defined hereinabove.

One embodiment provides a compound of Formula (I) or a pharmaceutically acceptable salt thereof, wherein:
$R^3$ is alkyl, cycloalkyl, haloalkyl, —C(O)OR$^5$, —C(O)NR$_a$R$_b$, or aryl, said aryl optionally substituted with one to five substituents independently selected from $C_1$ to $C_6$ alkyl, $C_1$ to $C_4$ haloalkyl, —OR$^4$, and/or halogen.
Preferably, $R^3$ is $C_1$ to $C_6$ alkyl, $C_3$ to $C_6$ cycloalkyl, $C_1$ to $C_4$ haloalkyl, —C(O)OR$^5$, —C(O)NR$_a$R$_b$, or aryl, said aryl optionally substituted with one to five substituents independently selected from $C_1$ to $C_6$ alkyl, $C_1$ to $C_4$ haloalkyl, —OR$^4$, and/or halogen.

One embodiment provides a compound of Formula (I) or a pharmaceutically acceptable salt thereof, wherein:
$R^1$ is $C_1$ to $C_6$ alkyl or aryl, said aryl optionally substituted with one to five substituents independently selected from $C_1$ to $C_6$ alkyl, $C_1$ to $C_4$ haloalkyl, —OR$^4$, and/or halogen;
$R^3$ is $C_1$ to $C_6$ alkyl, $C_3$ to $C_8$ cycloalkyl, $C_1$ to $C_6$ haloalkyl, —C(O)OR$^5$, —C(O)NR$_a$R$_b$, or aryl, said aryl optionally substituted with one to five substituents independently selected from $C_1$ to $C_6$ alkyl, $C_1$ to $C_4$ haloalkyl, —OR$^4$, and/or halogen;
each $R^4$ is independently selected from $C_1$ to $C_6$ alkyl, $C_1$ to $C_4$ haloalkyl, and/or benzyl; $R^5$ is hydrogen, $C_1$ to $C_6$ alkyl, or benzyl;
$R_a$ and $R_b$ are independently selected from hydrogen, $C_1$ to $C_6$ alkyl, $C_1$ to $C_6$ haloalkyl, and/or benzyl; and
$R^2$, Q, and n are defined hereinabove.
Compounds of this embodiment include the compounds of Formula (Ia). Other compounds of this embodiment include the compounds of Formula (Ib).

One embodiment provides a compound of Formula (I) or a pharmaceutically acceptable salt thereof, wherein:
$R^1$ is $C_1$ to $C_6$ alkyl or aryl, said aryl optionally substituted with one to five substituents independently selected from $C_1$ to $C_6$ alkyl, $C_1$ to $C_4$ haloalkyl, —OR$^4$, and/or halogen;
$R^3$ is $C_1$ to $C_6$ alkyl, $C_3$ to $C_8$ cycloalkyl, $C_1$ to $C_6$ haloalkyl, —C(O)OR$^5$, —C(O)NR$_a$R$_b$, or aryl, said aryl optionally substituted with one to five substituents independently selected from $C_1$ to $C_6$ alkyl, $C_1$ to $C_4$ haloalkyl, —OR$^4$, and/or halogen;
each $R^4$ is independently selected from $C_1$ to $C_6$ alkyl, $C_1$ to $C_4$ haloalkyl, and/or benzyl;
$R^5$ is hydrogen, $C_1$ to $C_6$ alkyl, or benzyl;
$R_a$ and $R_b$ are independently selected from hydrogen, $C_1$ to $C_6$ alkyl, $C_1$ to $C_6$ haloalkyl, and/or benzyl; and
$R^2$, Q, and n are defined hereinabove.
Compounds of this embodiment include the compounds of Formula (Ia). Other compounds of this embodiment include the compounds of Formula (Ib).

One embodiment provides a compound of Formula (I) or a pharmaceutically acceptable salt thereof, wherein:
$R^1$ is $C_1$ to $C_4$ alkyl or phenyl, said phenyl optionally substituted with one to two substituents independently selected from $C_1$ to $C_4$ alkyl, $C_1$ to $C_2$ haloalkyl, —OR$^4$, and/or halogen;
$R^3$ is $C_1$ to $C_4$ alkyl, $C_3$ to $C_6$ cycloalkyl, $C_1$ to $C_3$ haloalkyl, —C(O)OR$^5$, —C(O)NHR$_b$, or phenyl, said phenyl optionally substituted with one to two substituents independently selected from $C_1$ to $C_4$ alkyl, $C_1$ to $C_2$ haloalkyl, —OR$^4$, and/or halogen;
each $R^4$ is independently selected from $C_1$ to $C_4$ alkyl, $C_1$ to $C_3$ haloalkyl, and/or benzyl; $R^5$ is hydrogen, $C_1$ to $C_4$ alkyl, or benzyl;
$R_b$ is selected from hydrogen, $C_1$ to $C_4$ alkyl, $C_1$ to $C_3$ haloalkyl, and benzyl;
n is zero or 1; and
$R^2$ and Q are defined hereinabove.
Compounds of this embodiment include the compounds of Formula (Ia). Other compounds of this embodiment include the compounds of Formula (Ib).

One embodiment provides a compound of Formula (I) or a pharmaceutically acceptable salt thereof, wherein:
Q is

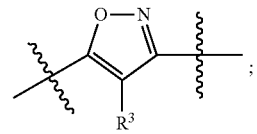

;

$R^3$ is alkyl, cycloalkyl, haloalkyl, —C(O)OR$^5$, —C(O)NR$_a$R$_b$, or aryl, said aryl optionally substituted with one to five substituents independently selected from $C_1$ to $C_6$ alkyl, $C_1$ to $C_4$ haloalkyl, —OR$^4$, and/or halogen;
each $R^4$ is independently selected from $C_1$ to $C_6$ alkyl, $C_1$ to $C_4$ haloalkyl, and/or benzyl; and
$R^5$ is hydrogen, alkyl, or benzyl; and $R_a$ and $R_b$ are independently selected from hydrogen, alkyl, haloalkyl, and/or benzyl.
Preferably, $R^3$ is $C_1$ to $C_6$ alkyl, $C_3$ to $C_8$ cycloalkyl, $C_1$ to $C_4$ haloalkyl, —C(O)OR$^5$, —C(O)NR$_a$R$_b$, or aryl, said aryl optionally substituted with one to three substituents independently selected from $C_1$ to $C_4$ alkyl, $C_1$ to $C_2$ haloalkyl, —OR$^4$, and/or halogen. More preferably, $R^3$ is $C_1$ to $C_4$ alkyl, $C_3$ to $C_6$ cycloalkyl, $C_1$ to $C_2$ haloalkyl, —C(O)OR$^5$, —C(O)NHR$_b$, or phenyl, said phenyl optionally substituted with one to two substituents independently selected from $C_1$ to $C_4$ alkyl, $C_1$ to $C_2$ haloalkyl, —OR$^4$, and/or halogen.

One embodiment provides a compound of Formula (I) or a pharmaceutically acceptable salt thereof, wherein:

Q is

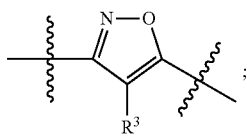

R³ is alkyl, cycloalkyl, haloalkyl, —C(O)OR⁵, —C(O)NR$_a$R$_b$, or aryl, said aryl optionally substituted with one to five substituents independently selected from $C_1$ to $C_6$ alkyl, $C_1$ to $C_4$ haloalkyl, —OR⁴, and/or halogen;

each R⁴ is independently selected from $C_1$ to $C_6$ alkyl, $C_1$ to $C_4$ haloalkyl, and/or benzyl; R⁵ is hydrogen, alkyl, or benzyl; and R$_a$ and R$_b$ are independently selected from hydrogen, alkyl, haloalkyl, and/or benzyl.

Preferably, R³ is $C_1$ to $C_6$ alkyl, $C_3$ to $C_8$ cycloalkyl, $C_1$ to $C_4$ haloalkyl, —C(O)OR⁵, —C(O)NR$_a$R$_b$, or aryl, said aryl optionally substituted with one to three substituents independently selected from $C_1$ to $C_4$ alkyl, $C_1$ to $C_2$ haloalkyl, —OR⁴, and/or halogen. More preferably, R³ is $C_1$ to $C_4$ alkyl, $C_3$ to $C_6$ cycloalkyl, $C_1$ to $C_2$ haloalkyl, —C(O)OR⁵, —C(O)NHR$_b$, or phenyl, said phenyl optionally substituted with one to two substituents independently selected from $C_1$ to $C_4$ alkyl, $C_1$ to $C_2$ haloalkyl, —OR⁴, and/or halogen.

One embodiment provides a compound of Formula (I) or a pharmaceutically acceptable salt thereof, wherein:
Q is

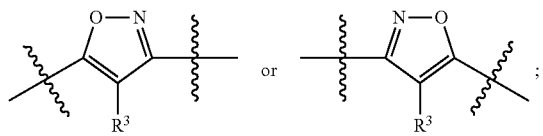

R¹ is phenyl optionally substituted with one to five substituents independently selected from $C_1$ to $C_6$ alkyl, $C_1$ to $C_4$ haloalkyl, —OR⁴, and/or halogen;

R³ is $C_1$ to $C_6$ alkyl, $C_1$ to $C_4$ haloalkyl, $C_3$ to $C_6$ cycloalkyl, —C(O)OR⁵, —C(O)NR$^a$R$^b$, or phenyl optionally substituted with one to five substituents independently selected from $C_1$ to $C_6$ alkyl, $C_1$ to $C_4$ haloalkyl, —OR⁴, and/or halogen;

each R⁴ is independently selected from $C_1$ to $C_6$ alkyl, $C_1$ to $C_4$ haloalkyl, and/or benzyl;

R⁵ is hydrogen or $C_1$ to $C_6$ alkyl; and

R$^a$ and R$^b$ are independently selected from hydrogen, $C_1$ to $C_6$ alkyl, and/or $C_1$ to $C_4$ haloalkyl.

Preferably, R¹ is phenyl optionally substituted with one to two substituents independently selected from $C_1$ to $C_4$ alkyl, $C_1$ to $C_3$ haloalkyl, —OR⁴, and/or halogen; R³ is $C_1$ to $C_4$ alkyl, $C_1$ to $C_3$ haloalkyl, $C_3$ to $C_6$ cycloalkyl, —C(O)OR⁵, —C(O)NHR$^b$, or phenyl optionally substituted with one to two substituents independently selected from $C_1$ to $C_4$ alkyl, $C_1$ to $C_3$ haloalkyl, —OR⁴, and/or halogen; each R⁴ is independently selected from $C_1$ to $C_4$ alkyl, $C_1$ to $C_3$ haloalkyl, and/or benzyl; R⁵ is hydrogen or $C_1$ to $C_4$ alkyl; and R$^b$ is selected from hydrogen, $C_1$ to $C_6$ alkyl, and $C_1$ to $C_4$ haloalkyl.

One embodiment provides a compound of Formula (I) or a pharmaceutically acceptable salt thereof, wherein: R¹ is aryl optionally substituted with one to five substituents independently selected from $C_1$ to $C_6$ alkyl, $C_1$ to $C_4$ haloalkyl, —OR⁴, and/or halogen. Preferably, R¹ is phenyl optionally substituted with one to five substituents independently selected from $C_1$ to $C_6$ alkyl, $C_1$ to $C_4$ haloalkyl, —OR⁴, and/or halogen. Preferably, n is zero, 1, or 2; and more preferably, n is zero or 1.

One embodiment provides a compound of Formula (I) or a pharmaceutically acceptable salt thereof, wherein n is zero or 1.

One embodiment provides a compound of Formula (I) or a pharmaceutically acceptable salt thereof, wherein n is zero.

One embodiment provides a compound of Formula (I) or a pharmaceutically acceptable salt thereof, wherein:
Q is

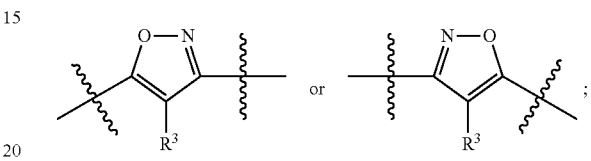

n is zero or 1;

R¹ is phenyl; R² is halogen; R³ is $C_1$ to $C_4$ alkyl, cyclopropyl, phenyl, —CF₃, —CF₂H, —(CH₂)₂CF₃, —CF₂CH₃, —CF₂CH₂CH₃, —C(O)NHR$^a$, or —C(O)OR⁵;

R⁵ is hydrogen or methyl; and

R$^a$ is methyl or 2,2,2-trifluoroethyl.

One embodiment provides a compound of Formula (I) or a pharmaceutically acceptable salt thereof, wherein:
Q is

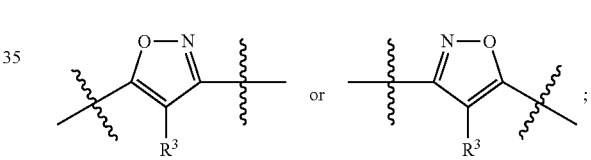

n is zero;

R¹ is phenyl; and

R³ is —CF₃.

The compounds of this embodiment may be provided as trifluoroacetic acid salts.

One embodiment provides 1-(4-(5-(3-phenyl-4-(trifluoromethyl)isoxazol-5-yl)-1,2,4-oxadiazol-3-yl)benzyl)azetidine-3-carboxylic acid or a pharmaceutically acceptable salt thereof, which has the structure:

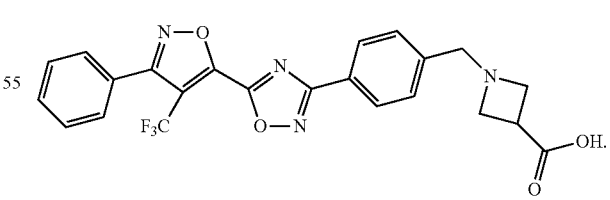

The compound of this embodiment may be provided as a trifluoroacetic acid salt.

One embodiment provides 1-(4-(5-(5-phenyl-4-(trifluoromethyl)isoxazol-3-yl)-1,2,4-oxadiazol-3-yl)benzyl)azetidine-3-carboxylic acid or a pharmaceutically acceptable salt thereof, which has the structure:

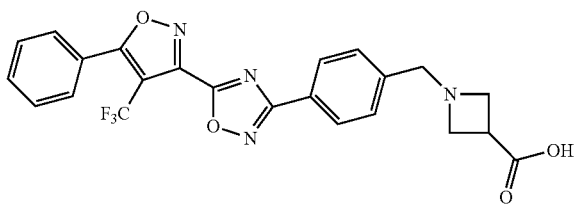 [SMILES: O=C(O)C1CN(Cc2ccc(-c3noc(-c4noc(-c5ccccc5)c4C(F)(F)F)n3)cc2)C1]

The compound of this embodiment may be provided as a trifluoroacetic acid salt.

One embodiment provides a compound of Formula (I) or a pharmaceutically acceptable salt thereof, wherein: $R^1$ is alkyl. Preferably, $R^1$ is $C_1$ to $C_6$ alkyl. More preferably, $R^1$ is $C_1$ to $C_4$ alkyl.

One embodiment provides a compound of Formula (I) or a pharmaceutically acceptable salt thereof, wherein:
Q is

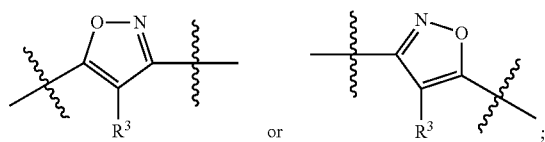

n is zero;
$R^1$ is $C_1$ to $C_6$ alkyl; and
$R^3$ is $C_1$ to $C_6$ alkyl.

One embodiment provides a compound of Formula (I) or a pharmaceutically acceptable salt thereof, selected from the group consisting of:
1-(4-(5-(3-phenyl-4-(trifluoromethyl)isoxazol-5-yl)-1,2,4-oxadiazol-3-yl)benzyl)azetidine-3-carboxylic acid;
1-(4-(5-(5-phenyl-4-(trifluoromethyl)isoxazol-3-yl)-1,2,4-oxadiazol-3-yl)benzyl)azetidine-3-carboxylic acid;
1-(4-(5-(4-butyl-5-phenylisoxazol-3-yl)-1,2,4-oxadiazol-3-yl)benzyl)azetidine-3-carboxylic acid;
1-(4-(5-(4-isobutyl-5-phenylisoxazol-3-yl)-1,2,4-oxadiazol-3-yl)benzyl)azetidine-3-carboxylic acid;
1-(4-(5-(4-ethyl-5-phenylisoxazol-3-yl)-1,2,4-oxadiazol-3-yl)benzyl)azetidine-3-carboxylic acid;
1-(4-(5-(4-cyclopropyl-5-phenylisoxazol-3-yl)-1,2,4-oxadiazol-3-yl)benzyl)-azetidine-3-carboxylic acid, 2,2,2-trifluoroacetic acid salt;
1-(4-(5-(4-tert-butyl-5-phenylisoxazol-3-yl)-1,2,4-oxadiazol-3-yl)benzyl)-azetidine-3-carboxylic acid;
1-(4-(5-(5-phenyl-4-(3,3,3-trifluoropropyl)isoxazol-3-yl)-1,2,4-oxadiazol-3-yl)benzyl)azetidine-3-carboxylic acid;
1-(4-(5-(4-(1,1-difluoroethyl)-5-phenylisoxazol-3-yl)-1,2,4-oxadiazol-3-yl)benzyl)azetidine-3-carboxylic acid;
1-(4-(5-(4-(1,1-difluoropropyl)-5-phenylisoxazol-3-yl)-1,2,4-oxadiazol-3-yl)benzyl)azetidine-3-carboxylic acid;
1-(4-(5-(3-phenyl-4-propylisoxazol-5-yl)-1,2,4-oxadiazol-3-yl)benzyl)azetidine-3-carboxylic acid;
1-(4-(5-(4-(difluoromethyl)-3-phenylisoxazol-5-yl)-1,2,4-oxadiazol-3-yl)benzyl)azetidine-3-carboxylic acid;
1-(4-(5-(4-(methoxycarbonyl)-3-phenylisoxazol-5-yl)-1,2,4-oxadiazol-3-yl)benzyl)azetidine-3-carboxylic acid;
1-(4-(5-(4-(methylcarbamoyl)-3-phenylisoxazol-5-yl)-1,2,4-oxadiazol-3-yl)benzyl)azetidine-3-carboxylic acid;
1-(4-(5-(3-phenyl-4-(2,2,2-trifluoroethylcarbamoyl)isoxazol-5-yl)-1,2,4-oxadiazol-3-yl)benzyl)azetidine-3-carboxylic acid;
5-(3-(4-((3-carboxyazetidin-1-yl)methyl)phenyl)-1,2,4-oxadiazol-5-yl)-3-phenylisoxazole-4-carboxylic acid;
1-(4-(5-(4,5-diphenylisoxazol-3-yl)-1,2,4-oxadiazol-3-yl)benzyl)azetidine-3-carboxylic acid;
1-(4-(5-(5-isobutyl-4-propylisoxazol-3-yl)-1,2,4-oxadiazol-3-yl)benzyl)azetidine-3-carboxylic acid;
1-(4-(5-(4-isobutyl-5-propylisoxazol-3-yl)-1,2,4-oxadiazol-3-yl)benzyl)azetidine-3-carboxylic acid;
1-(4-(5-(5-isobutyl-4-(trifluoromethyl)isoxazol-3-yl)-1,2,4-oxadiazol-3-yl)benzyl)-azetidine-3-carboxylic acid;
1-(2-fluoro-4-(5-(3-phenyl-4-(trifluoromethyl)isoxazol-5-yl)-1,2,4-oxadiazol-3-yl)benzyl)azetidine-3-carboxylic acid;
1-(2-methyl-4-(5-(3-phenyl-4-(trifluoromethyl)isoxazol-5-yl)-1,2,4-oxadiazol-3-yl)benzyl)azetidine-3-carboxylic acid;
1-(3-chloro-4-(5-(3-phenyl-4-(trifluoromethyl)isoxazol-5-yl)-1,2,4-oxadiazol-3-yl)benzyl)azetidine-3-carboxylic acid;
1-(4-(5-(3-phenyl-4-(trifluoromethyl)isoxazol-5-yl)-1,2,4-oxadiazol-3-yl)-3-(trifluoromethyl)benzyl)azetidine-3-carboxylic acid; and
1-(4-(5-(4,5-diphenylisoxazol-3-yl)-1,2,4-oxadiazol-3-yl)-3-(trifluoromethyl)benzyl)azetidine-3-carboxylic acid, 2,2,2-trifluoroacetic acid salt.

One embodiment provides a 2,2,2-trifluoroacetic acid salt of a compound according to Formula (I), wherein:
Q is

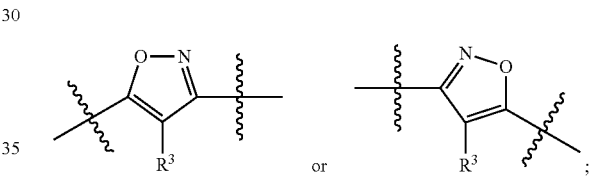

n is zero or an integer selected from 1 through 4;
$R^1$ is alkyl or aryl, said aryl optionally substituted with one to five substituents independently selected from $C_1$ to $C_6$ alkyl, $C_1$ to $C_4$ haloalkyl, $-OR^4$, and/or halogen;
each $R^2$ is independently selected from $C_1$ to $C_6$ alkyl, $C_1$ to $C_4$ haloalkyl, $-OR^4$, and/or halogen;
$R^3$ is alkyl, cycloalkyl, haloalkyl, $-C(O)OR^5$, $-C(O)NR_aR_b$, or aryl, said aryl optionally substituted with one to five substituents independently selected from $C_1$ to $C_6$ alkyl, $C_1$ to $C_4$ haloalkyl, $-OR^4$, and/or halogen;
each $R^4$ is independently selected from $C_1$ to $C_6$ alkyl, $C_1$ to $C_4$ haloalkyl, and/or benzyl;
$R^5$ is hydrogen, alkyl, or benzyl; and
$R_a$ and $R_b$ are independently selected from hydrogen, alkyl, haloalkyl, and/or benzyl.

One embodiment provides a composition comprising a compound according to Formula (I) or a pharmaceutically acceptable salt thereof; and a pharmaceutically acceptable carrier; wherein
Q is

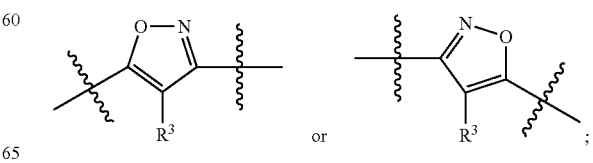

n is zero or an integer selected from 1 through 4;

R[1] is alkyl or aryl, said aryl optionally substituted with one to five substituents independently selected from $C_1$ to $C_6$ alkyl, $C_1$ to $C_4$ haloalkyl, —OR[4], and/or halogen;

each R[2] is independently selected from $C_1$ to $C_6$ alkyl, $C_1$ to $C_4$ haloalkyl, —OR[4], and/or halogen;

R[3] is alkyl, cycloalkyl, haloalkyl, —C(O)OR[5], —C(O)NR$_a$R$_b$, or aryl, said aryl optionally substituted with one to five substituents independently selected from $C_1$ to $C_6$ alkyl, $C_1$ to $C_4$ haloalkyl, —OR[4], and/or halogen;

each R[4] is independently selected from $C_1$ to $C_6$ alkyl, $C_1$ to $C_4$ haloalkyl, and/or benzyl;

R[5] is hydrogen, alkyl, or benzyl; and

R$_a$ and R$_b$ are independently selected from hydrogen, alkyl, haloalkyl, and/or benzyl.

One embodiment provides a composition comprising 1-(4-(5-(3-phenyl-4-(trifluoromethyl)isoxazol-5-yl)-1,2,4-oxadiazol-3-yl)benzyl)azetidine-3-carboxylic acid or a pharmaceutically acceptable salt thereof; and a pharmaceutically acceptable carrier. The compound of this embodiment may be provided as a trifluoroacetic acid salt.

One embodiment provides a composition comprising 1-(4-(5-(5-phenyl-4-(trifluoromethyl)isoxazol-3-yl)-1,2,4-oxadiazol-3-yl)benzyl)azetidine-3-carboxylic acid or a pharmaceutically acceptable salt thereof; and a pharmaceutically acceptable carrier. The compound of this embodiment may be provided as a trifluoroacetic acid salt.

One embodiment provides a method of treating a disease or disorder associated with the activity of G protein-coupled receptor $S1P_1$, the method comprising administering to a mammalian patient of a compound of Formula (I) or a pharmaceutically acceptable salt thereof, wherein:

Q is

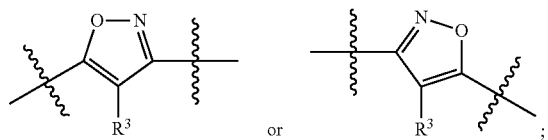

n is zero or an integer selected from 1 through 4;

R[1] is alkyl or aryl, said aryl optionally substituted with one to five substituents independently selected from $C_1$ to $C_6$ alkyl, $C_1$ to $C_4$ haloalkyl, —OR[4], and/or halogen;

each R[2] is independently selected from $C_1$ to $C_6$ alkyl, $C_1$ to $C_4$ haloalkyl, —OR[4], and/or halogen;

R[3] is alkyl, cycloalkyl, haloalkyl, —C(O)OR[5], —C(O)NR$_a$R$_b$, or aryl, said aryl optionally substituted with one to five substituents independently selected from $C_1$ to $C_6$ alkyl, $C_1$ to $C_4$ haloalkyl, —OR[4], and/or halogen;

each R[4] is independently selected from $C_1$ to $C_6$ alkyl, $C_1$ to $C_4$ haloalkyl, and/or benzyl;

R[5] is hydrogen, alkyl, or benzyl; and

R$_a$ and R$_b$ are independently selected from hydrogen, alkyl, haloalkyl, and/or benzyl.

One embodiment provides a method of treating a disease or disorder associated with the activity of G protein-coupled receptor $S1P_1$, the method comprising administering to a mammalian patient of a compound of Formula (I) or a pharmaceutically acceptable salt thereof, wherein:

Q is

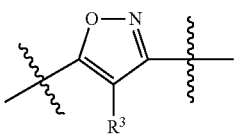 or 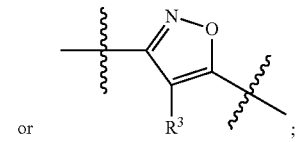;

n is zero;
R[1] is phenyl; and
R[3] is —CF$_3$.

The compounds of this embodiment may be provided as trifluoroacetic acid salts.

One embodiment provides a method of treating a disease or disorder associated with the activity of G protein-coupled receptor $S1P_1$, the method comprising administering to a mammalian patient of 1-(4-(5-(3-phenyl-4-(trifluoromethyl)isoxazol-5-yl)-1,2,4-oxadiazol-3-yl)benzyl)azetidine-3-carboxylic acid or a pharmaceutically acceptable salt thereof.

One embodiment provides a method of treating a disease or disorder associated with the activity of G protein-coupled receptor $S1P_1$, the method comprising administering to a mammalian patient of 1-(4-(5-(5-phenyl-4-(trifluoromethyl)isoxazol-3-yl)-1,2,4-oxadiazol-3-yl)benzyl)azetidine-3-carboxylic acid or a pharmaceutically acceptable salt thereof.

Definitions

The features and advantages of the invention may be more readily understood by those of ordinary skill in the art upon reading the following detailed description. It is to be appreciated that certain features of the invention that are, for clarity reasons, described above and below in the context of separate embodiments, may also be combined to form a single embodiment. Conversely, various features of the invention that are, for brevity reasons, described in the context of a single embodiment, may also be combined so as to form sub-combinations thereof. Embodiments identified herein as exemplary or preferred are intended to be illustrative and not limiting.

Unless specifically stated otherwise herein, references made in the singular may also include the plural. For example, "a" and "an" may refer to either one, or one or more.

Unless otherwise indicated, any heteroatom with unsatisfied valences is assumed to have hydrogen atoms sufficient to satisfy the valences.

The definitions set forth herein take precedence over definitions set forth in any patent, patent application, and/or patent application publication incorporated herein by reference.

Listed below are definitions of various terms used to describe the present invention. These definitions apply to the terms as they are used throughout the specification (unless they are otherwise limited in specific instances) either individually or as part of a larger group.

Throughout the specification, groups and substituents thereof may be chosen by one skilled in the field to provide stable moieties and compounds.

In accordance with a convention used in the art,

is used in structural formulas herein to depict the bond that is the point of attachment of the moiety or substituent to the core or backbone structure.

The terms "halo" and "halogen," as used herein, refer to F, Cl, Br, or I.

The term "alkyl" as used herein, refers to both branched and straight-chain saturated aliphatic hydrocarbon groups containing, for example, from 1 to 12 carbon atoms, from 1 to 6 carbon atoms, and from 1 to 4 carbon atoms. Examples of alkyl groups include, but are not limited to, methyl (Me), ethyl (Et), propyl (e.g., n-propyl and i-propyl), butyl (e.g., n-butyl, i-butyl, sec-butyl, and t-butyl), and pentyl (e.g., n-pentyl, isopentyl, neopentyl), n-hexyl, 2-methylpentyl, 2-ethylbutyl, 3-methylpentyl, and 4-methylpentyl. When numbers appear in a subscript after the symbol "C", the subscript defines with more specificity the number of carbon atoms that a particular group may contain. For example, "$C_1$-$C_6$ alkyl" denotes straight and branched chain alkyl groups with one to six carbon atoms.

The term "haloalkyl," as used herein, refers to an alkyl group in which one or more hydrogen atoms are replaced by halogen atom(s), the number of which can range from one up to the total number of hydrogen atoms that could otherwise exist in the parent alkyl group. Representative examples of haloalkyl groups include, but are not limited to, chloromethyl (—$CH_2Cl$), trifluoromethyl (—$CF_3$—, and 2,2,2-trifluoroethyl (—$CH_2CF_3$). When numbers appear in a subscript after the symbol "C", the subscript defines with more specificity the number of carbon atoms that a particular haloalkyl group may contain. For example, "$C_1$-$C_4$ haloalkyl" denotes straight and branched chain haloalkyl groups with one to four carbon atoms.

The term "cycloalkyl," as used herein, refers to a group derived from a non-aromatic monocyclic or polycyclic hydrocarbon molecule by removal of one hydrogen atom from a saturated ring carbon atom. Representative examples of cycloalkyl groups include, but are not limited to, cyclopropyl, cyclopentyl, and cyclohexyl. When numbers appear in a subscript after the symbol "C", the subscript defines with more specificity the number of carbon atoms that a particular cycloalkyl group may contain. For example, "$C_3$-$C_6$ cycloalkyl" denotes cycloalkyl groups with three to six carbon atoms.

The term "alkoxy," as used herein, refers to an alkyl group attached to the parent molecular moiety through an oxygen atom, for example, methoxy group (—$OCH_3$).

The term "aryl," as used herein, refers to a group of atoms derived from a molecule containing aromatic ring(s) by removing one hydrogen that is bonded to the aromatic ring(s). Representative examples of aryl groups include, but are not limited to, phenyl, naphthyl, indanyl, indenyl, and 1,2,3,4-tetrahydronaphth-5-yl.

The term "benzyl," as used herein, refers to a methyl group in which one of the hydrogen atoms is replaced by a phenyl group.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; and alkali or organic salts of acidic residues such as carboxylic acids. The pharmaceutically acceptable salts include the conventional non-toxic salts or the quaternary ammonium salts of the parent compound formed, for example, from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences*, 17th Ed., Mack Publishing Company, Easton, Pa., p. 1418 (1985), the disclosure of which is hereby incorporated by reference.

Salt(s) of the Formula (I) compounds can be formed by, for example, reacting a Formula (I) compound with, for example, an equivalent amount of acid or base in a medium that allows the newly formed salt to, for example, either be precipitated out, or be isolated via lyophilization. Exemplary acidic salt(s) that the compounds of Formula (I) can form with inorganic and/or organic acids include, but are not limited to, for example, include acetate, ascorbate, benzoate, benzenesulfonate, bisulfate, bitartrate, acid citrate, citrate, ethanesulfonate, formate, fumarate, gentisinate, gluconate, glucaronate, glutamate, hydrochloride, hydrobromide, hydroiodide, isonicotinate, maleate, mesylate, methanesulfonate, nitrate, pantothenate, phosphate, acid phosphate, saccharate, salicylate, succinate, sulfate, tartrate, p-toluenesulfonate, trifluoroacetate, lactate, and pamoate [i.e., 1,1'-methylene-bis-(2-hydroxy-3-naphthoate)] salts. Such salts can be formed in accordance with methods known to a person of ordinary skill in the art.

Exemplary basic salt(s) that the compounds of Formula (I) can form with inorganic and/or organic bases include, but are not limited to, for example, ammonium salts; alkali metal salts, such as, for example, sodium, lithium and potassium salts: alkaline earth metal salts, such as, for example, calcium and magnesium salts; salts formed with organic bases, such as, for example, benzathines, dicyclohexylamines, 2-amino-2-(hydroxymethyl)propane-1,3-diol (trisamine or tris), hydrabamines (such as, for example, N,N-bis(dehydroabietyl)ethylenediamine), N-methyl-D-glucamines, N-methyl-D-glycamides, and t-butyl amines; salts formed with amino acids, such as, for example, arginine and lysine; and salts formed by using agents, such as, for example, lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myristyl and stearyl chlorides, bromides and iodides), and aralkyl halides (e.g., benzyl and phenethyl bromides) to quaternize basic nitrogen-containing groups. Such salts can be formed in accordance with methods known to a person of ordinary skill in the art.

In addition, compounds of Formula (I) are, subsequent to their preparation, preferably isolated and purified to obtain a composition containing an amount by weight equal to or greater than 99% of a compound of Formula (I) ("substantially pure"), which is then used or formulated as described herein. Such "substantially pure" compounds of Formula (I) are also contemplated herein as part of the present invention.

Any compound that can be converted in vivo to provide the bioactive agent (i.e., the compound of Formula (I)) is a prodrug within the scope and spirit of the invention.

The term "prodrugs" as employed herein includes esters and carbonates formed by reacting one or more hydroxyls of compounds of Formula (I) with alkyl, alkoxy, or aryl substituted acylating agents employing procedures known to those skilled in the art to generate acetates, pivalates, methylcarbonates, benzoates, and the like.

Various forms of prodrugs are well known in the art and are described in:

a) Wermuth, C. G. et al., *The Practice of Medicinal Chemistry*, Chapter 31, Academic Press (1996);

b) *Design of Prodrugs*, Bundgaard, H. ed., Elsevier (1985);

c) Bundgaard, H., Chapter 5, "Design and Application of Prodrugs," *A Textbook of Drug Design and Development*, pp. 113-191, Krosgaard-Larsen, P. et al., eds., Harwood Academic Publishers (1991); and d) Testa, B. et al., *Hydrolysis in Drug and Prodrug Metabolism*, Wiley-VCH (2003).

In addition, compounds of the Formula (I) are, subsequent to their preparation, preferably isolated and purified to obtain a composition containing an amount by weight equal to or greater than 99% Formula (I) compound ("substantially pure" compound I), which is then used or formulated as described herein. Such "substantially pure" compounds of the Formula (I) are also contemplated herein as part of the present invention.

"Stable compound" and "stable structure" are meant to indicate a compound that is sufficiently robust to survive isolation to a useful degree of purity from a reaction mixture, and formulation into an efficacious therapeutic agent. The present invention is intended to embody stable compounds.

"Therapeutically effective amount" is intended to include an amount of a compound of the present invention alone or an amount of the combination of compounds claimed or an amount of a compound of the present invention in combination with other active ingredients effective to act as an agonist to $S1P_1$, or effective to treat or prevent vascular disease or autoimmune diseases.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting it development; and/or (c) relieving the disease-state, i.e., causing regression of the disease state.

Compounds of the present invention may contain one or more additional asymmetric carbon atoms and therefore exist in two or more stereoisomeric forms. The present invention includes all of the possible individual stereoisomers, the individual tautomeric forms thereof, together with mixtures thereof. Separation of diastereoisomers may be achieved by conventional techniques, e.g., by fractional crystallization, chromatography or HPLC of a stereoisomeric mixture of a compound of the present invention, or a suitable salt or derivative thereof. An individual enantiomer of the compound may also be prepared from a corresponding optically pure intermediate or by resolution, such as by HPLC of the corresponding racemate using a suitable chiral support or by fractional crystallization of the diastereoisomeric salts formed by reaction of the corresponding racemate with a suitable optically active acid or base, as appropriate. All stereoisomers of the compounds of the instant invention are contemplated, either in admixture or in pure or substantially pure form.

The compounds of the present invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed.

Also embraced within this invention is a class of pharmaceutical compositions comprising the compound of Formula (I) or a pharmaceutically acceptable salt thereof in association with one or more non-toxic, pharmaceutically-acceptable carriers and/or diluents and/or adjuvants (collectively referred to herein as "carrier" materials) and, if desired, other active ingredients. The compounds of Formula (I) may be administered by any suitable route, preferably in the form of a pharmaceutical composition adapted to such a route, and in a dose effective for the treatment intended. The compounds and compositions of the present invention may, for example, be administered orally, mucosally, or parentally including intravascularly, intravenously, intraperitoneally, subcutaneously, intramuscularly intrasternally and infusion techniques, in dosage unit formulations containing conventional pharmaceutically acceptable carriers, adjuvants, and vehicles. For example, the pharmaceutical carrier may contain a mixture of mannitol or lactose and microcrystalline cellulose. The mixture may contain additional components such as a lubricating agent, e.g., magnesium stearate and a disintegrating agent such as crospovidone. The carrier mixture may be filled into a gelatin capsule or compressed as a tablet.

The pharmaceutically active compounds of this invention can be processed in accordance with conventional methods of pharmacy to produce medicinal agents for administration to patients, including humans and other mammals.

For oral administration, the pharmaceutical composition may be in the form of, for example, a tablet, capsule, suspension, or liquid. The pharmaceutical composition is preferably made in the form of a dosage unit containing a particular amount of the active ingredient. Examples of such dosage units are tablets or capsules. For example, these may contain an amount of active ingredient from about 1 to 2000 mg, preferably from about 1 to 500 mg, more preferably from about 5 to 150 mg. A suitable daily dose for a human or other mammal may vary widely depending on the condition of the patient and other factors, but, once again, can be determined using routine methods.

The amounts of compounds that are administered and the dosage regimen for treating a disease condition with the compounds and/or compositions of this invention depends on a variety of factors, including the age, weight, sex, the medical condition of the subject, the type of disease, the severity of the disease, the route and frequency of administration, and the particular compound employed. Thus, the dosage regimen may vary widely, but can be determined routinely using standard methods. A daily dose of about 0.01 to 1500 mg/kg body weight, preferably between about 0.5 and about 50 mg/kg body weight and most preferably between about 0.1 to 20 mg/kg body weight, may be appropriate. The daily dose can be administered in one to four doses per day.

For therapeutic purposes, the active compounds of this invention are ordinarily combined with one or more adjuvants appropriate to the indicated route of administration. If administered orally, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose.

The oily phase of the emulsions comprising compounds of Formula (I) may be constituted from known ingredients in a known manner. While the phase may comprise merely an emulsifier, it may comprise a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base which forms the oily dispersed phase of the cream formulations. Emulsifiers and emulsion stabilizers suitable for use in the formulation of the present invention include Tween 60, Span 80, cetostearyl alcohol, myristyl alcohol, glyceryl monostearate, sodium lauryl sulfate, glyceryl distearate alone or with a wax, or other materials well known in the art.

The choice of suitable oils or fats for the formulation is based on achieving the desired cosmetic properties, since the solubility of the active compound in most oils likely to be used in pharmaceutical emulsion formulations is very low. Thus, the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters may be used. These may be used alone or in combination depending on the properties required. Alternatively, high melting point lipids such as white soft paraffin and/or liquid paraffin or other mineral oils can be used.

Formulations for parenteral administration may be in the form of aqueous or non-aqueous isotonic sterile injection solutions or suspensions. These solutions and suspensions may be prepared from sterile powders or granules using one or more of the carriers or diluents mentioned for use in the formulations for oral administration or by using other suitable dispersing or wetting agents and suspending agents. The compounds may be dissolved in water, polyethylene glycol, propylene glycol, ethanol, corn oil, cottonseed oil, peanut oil, sesame oil, benzyl alcohol, sodium chloride, tragacanth gum, and/or various buffers. Other adjuvants and modes of administration are well and widely known in the pharmaceutical art. The active ingredient may also be administered by injection as a composition with suitable carriers including saline, dextrose, or water, or with cyclodextrin (i.e., CAPTISOL®), cosolvent solubilization (i.e., propylene glycol) or micellar solubilization (i.e., Tween 80).

The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

The pharmaceutical compositions may be subjected to conventional pharmaceutical operations such as sterilization and/or may contain conventional adjuvants, such as preservatives, stabilizers, wetting agents, emulsifiers, and buffers. Tablets and pills can additionally be prepared with enteric coatings. Such compositions may also comprise adjuvants, such as wetting, sweetening, flavoring, and perfuming agents.

Pharmaceutical compositions of this invention comprise the compound of Formula (I), or a pharmaceutically acceptable salt thereof, and optionally an additional agent selected from any pharmaceutically acceptable carrier, adjuvant, and vehicle. Alternate compositions of this invention comprise a compound of the Formula (I) described herein, or a pharmaceutically acceptable salt thereof, and a pharmaceutically acceptable carrier, adjuvant, or vehicle.

Pharmaceutically acceptable carriers, adjuvants, and vehicles that may be used in the pharmaceutical compositions of this invention include, but are not limited to, ion exchangers, alumina, aluminum stearate, lecithin, self-emulsifying drug delivery systems (SEDDS) such as d-alpha-tocopherol polyethyleneglycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as alpha-, beta-, and gamma-cyclodextrin, or chemically modified derivatives such as hydroxyalkylcyclodextrins, including 2- and 3-hydroxypropyl-cyclodextrins, or other solubilized derivatives may also be advantageously used to enhance delivery of compounds of the formulae described herein.

Utility

The human immune system has evolved to defend the body from micro-organisms, viruses, and parasites that can cause infection, disease or death. Complex regulatory mechanisms ensure that the various cellular components of the immune system target the foreign substances or organisms, while not causing permanent or significant damage to the individual. While the initiating events are not well understood at this time, in autoimmune disease states the immune system directs its inflammatory response to target organs in the afflicted individual. Different autoimmune diseases are typically characterized by the predominate or initial target organ or tissues affected; such as the joint in the case of rheumatoid arthritis, the thyroid gland in the case of Hashimoto's thyroiditis, the central nervous system in the case of multiple sclerosis, the pancreas in the case of type I diabetes, and the bowel in the case of inflammatory bowel disease. Thus it has been observed that therapeutic agents which act on the immune system or certain cell types of the immune system (such as B-lymphocytes, and T lymphocytes, T cells) may have utility in more than one autoimmune disease.

It is well recognized in the art, including the literature references cited herein, that S1P receptors are good targets for a wide variety of therapeutic applications, including autoimmune diseases. S1P receptors make good drug targets, because individual receptors are both tissue- and response-specific. Tissue specificity of the S1P receptors is important, because development of an agonist or antagonist selective for one receptor localizes the cellular response to tissues containing that receptor, limiting unwanted side effects. Response specificity of the S1P receptors is also important because it allows for development of agonists or antagonists that initiate or suppress certain cellular responses without affecting other processes. Therefore, compounds which act on some S1P receptor family members while having diminished or no activity at other family members are desirable and are expected to provide a therapeutic effect with an improved side effect profile (i.e., reduction or elimination of unwanted side effects).

As used herein, the term "agonist" in reference to $S1P_1$ refers to an agent which exerts pharmacological effects such as decreased motility of T cells, decreased trafficking of T cells, or decreased egress of T cells from lymphoid tissues. (Rosen et al., *Trends in Immunology*, 28:102 (2007)).

By virtue of their $S1P_1$ activity as agonists, the compounds of the present invention are immunoregulatory agents useful for treating or preventing autoimmune or chronic inflammatory diseases. The compounds of the present invention are useful to suppress the immune system in instances where immuno-suppression is in order, such as in bone marrow, organ or transplant rejection, autoimmune and chronic inflammatory diseases, including systemic lupus erythematosis, chronic rheumatoid arthritis, type I diabetes mellitus, inflammatory bowel disease, biliary cirrhosis, uveitis, multiple sclerosis, Crohn's disease, ulcerative colitis, bullous pemphigoid, sarcoidosis, psoriasis, autoimmune myositis, Wegener's granulomatosis, ichthyosis, Graves' ophthalmopathy, and asthma.

More particularly, the compounds of the present invention are useful to treat or prevent a disease or disorder selected from the group consisting of: transplantation of organs or tissue, graft-versus-host diseases brought about by transplantation, autoimmune syndromes including rheumatoid arthritis, systemic lupus erythematosus, Hashimoto's thyroiditis, multiple sclerosis, myasthenia gravis, type I diabetes, uveitis, posterior uveitis, allergic encephalomyelitis, glomerulonephritis, post-infectious autoimmune diseases including rheumatic fever and post-infectious glomerulonephritis, inflammatory and hyperproliferative skin diseases, psoriasis, atopic dermatitis, contact dermatitis, eczematous dermatitis, seborrhoeic dermatitis, lichen planus, pemphigus, bullous pemphigoid, epidermolysis bullosa, urticaria, angioedemas, vasculitis, erythema, cutaneous eosinophilia, lupus erythematosus, acne, alopecia greata, keratoconjunctivitis, vernal conjunctivitis, uveitis associated with Behcet's disease, keratitis, herpetic keratitis, conical cornea, dystrophia epithelialis corneae, corneal leukoma, ocular pemphigus, Mooren's ulcer, scleritis, Graves' ophthalmopathy, Vogt-Koyanagi-Harada syndrome, sarcoidosis, pollen allergies, reversible obstructive airway disease, bronchial asthma, allergic asthma, intrinsic asthma, extrinsic asthma, dust asthma, chronic or inveterate asthma, late asthma and airway hyperresponsiveness, bronchitis, gastric ulcers, vascular damage caused by ischemic diseases and thrombosis, ischemic bowel diseases, inflammatory bowel diseases, necrotizing enterocolitis, intestinal lesions associated with thermal burns, coeliac diseases, proctitis, eosinophilic gastroenteritis, mastocytosis, Crohn's disease, ulcerative colitis, migraine, rhinitis, eczema, interstitial nephritis, Goodpasture's syndrome, hemolytic-uremic syndrome, diabetic nephropathy, multiple myositis, Guillain-Barre syndrome, Meniere's disease, polyneuritis, multiple neuritis, mononeuritis, radiculopathy, hyperthyroidism, Basedow's disease, pure red cell aplasia, aplastic anemia, hypoplastic anemia, idiopathic thrombocytopenic purpura, autoimmune hemolytic anemia, agranulocytosis, pernicious anemia, megaloblastic anemia, anerythroplasia, osteoporosis, sarcoidosis, fibroid lung, idiopathic interstitial pneumonia, dermatomyositis, leukoderma vulgaris, ichthyosis vulgaris, photoallergic sensitivity, cutaneous T cell lymphoma, arteriosclerosis, atherosclerosis, aortitis syndrome, polyarteritis nodosa, myocardosis, scleroderma, Wegener's granuloma, Sjögren's syndrome, adiposis, eosinophilic fascitis, lesions of gingiva, periodontium, alveolar bone, substantia ossea dentis, glomerulonephritis, male pattern alopecia or alopecia senilis by preventing epilation or providing hair germination and/or promoting hair generation and hair growth, muscular dystrophy, pyoderma and Sezary's syndrome, Addison's disease, ischemia-reperfusion injury of organs which occurs upon preservation, transplantation or ischemic disease, endotoxin-shock, pseudomembranous colitis, colitis caused by drug or radiation, ischemic acute renal insufficiency, chronic renal insufficiency, toxinosis caused by lung-oxygen or drugs, lung cancer, pulmonary emphysema, cataracta, siderosis, retinitis pigmentosa, senile macular degeneration, vitreal scarring, corneal alkali burn, dermatitis erythema multiforme, linear IgA ballous dermatitis and cement dermatitis, gingivitis, periodontitis, sepsis, pancreatitis, diseases caused by environmental pollution, aging, carcinogenesis, metastasis of carcinoma and hypobaropathy, disease caused by histamine or leukotriene-$C_4$ release, Behcet's disease, autoimmune hepatitis, primary biliary cirrhosis, sclerosing cholangitis, partial liver resection, acute liver necrosis, necrosis caused by toxin, viral hepatitis, shock, or anoxia, B-virus hepatitis, non-A/non-B hepatitis, cirrhosis, alcoholic cirrhosis, hepatic failure, fulminant hepatic failure, late-onset hepatic failure, "acute-on-chronic" liver failure, augmentation of chemotherapeutic effect, cytomegalovirus infection, HCMV infection, AIDS, cancer, senile dementia, trauma, and chronic bacterial infection.

Also embodied within the present invention is a method of preventing or treating resistance to transplantation or transplantation rejection of organs or tissues in a mammalian patient in need thereof, which comprises administering a compound of Formula (I) or a pharmaceutically acceptable salt thereof. A therapeutically effective amount for preventing or treating resistance to transplantation or transplantation rejection may be administered.

A method of suppressing the immune system in a mammalian patient in need thereof, which comprises administering to the patient a compound of Formula (I) or a pharmaceutically acceptable salt thereof, is yet another embodiment. A therapeutically effective amount for suppressing the immune system may be administered.

Most particularly, the method described herein encompasses a method of treating or preventing bone marrow or organ transplant rejection which is comprised of administering to a mammalian patient in need of such treatment or prevention a compound of Formula (I) or a pharmaceutically acceptable salt thereof. A therapeutically effective amount for treating or preventing bone marrow or organ transplant rejection may be administered.

One embodiment provides a method for treating autoimmune and/or inflammatory diseases, comprising administering to a mammal in need thereof at least one compound of Formula (I) or a pharmaceutically acceptable salt thereof. Another embodiment provides the compounds of Formula (I) or pharmaceutically acceptable salts thereof, for use in therapy for the treatment of autoimmune and/or inflammatory diseases. In another embodiment, provided is the use of the compounds of Formula (I) or pharmaceutically acceptable salts thereof, for the manufacture of a medicament for the treatment or prophylaxis of autoimmune and/or inflammatory disease. A therapeutically effective amount may be employed in these embodiments. Preferably, in these embodiments, the autoimmune and inflammatory diseases are selected from multiple sclerosis, rheumatoid arthritis, inflammatory bowel disease (including Crohn's disease and ulcerative colitis), psoriasis, and as an agent to prevent the rejection of transplanted organs. Examples of compounds suitable for use in the method of this embodiment include compounds of Formula (I) or pharmaceutically acceptable salts thereof, wherein:

Q is

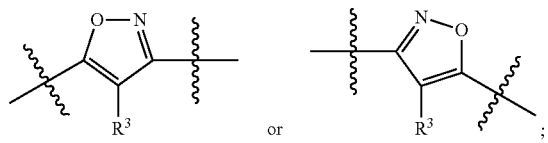

n is zero; $R^1$ is phenyl; and
$R^3$ is —$CF_3$, which may be provided as trifluoroacetic acid salts.
Examples of suitable compounds of Formula (I) are 1-(4-(5-(3-phenyl-4-(trifluoromethyl)isoxazol-5-yl)-1,2,4-oxadiazol-3-yl)benzyl)azetidine-3-carboxylic acid, 1-(4-(5-(5-phenyl-4-(trifluoromethyl)isoxazol-3-yl)-1,2,4-oxadiazol-3-yl)benzyl)azetidine-3-carboxylic acid, or pharmaceutically acceptable salts thereof. The method of the present embodiment includes administration of a therapeutically effect amount of a compound of Formula (I) or a pharmaceutically effective salt thereof.

In another embodiment, a method for treating vascular disease is provided comprising administering to a mammal in need thereof at least one compound of Formula (I) or a pharmaceutically acceptable salt thereof. Another embodiment provides the compounds of Formula (I) or pharmaceutically acceptable salts thereof, for use in therapy for the treatment of vascular disease. In another embodiment, provided is the use of the compounds of Formula (I) or pharmaceutically acceptable salts thereof, for the manufacture of a medicament for treatment of vascular disease. A therapeutically effective amount may be employed in these embodiments. Preferably, in these embodiments, the vascular disease is selected from atherosclerosis and ischemia reperfusion injury.

One embodiment provides a method of treating a disease or disorder associated with the activity of G protein-coupled receptor $S1P_1$, the method comprising administering to a mammalian patient of a compound of Formula (I) or a pharmaceutically acceptable salt thereof, wherein:

Q is

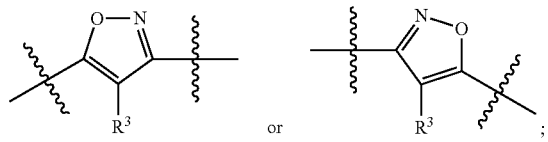

n is zero;
$R^1$ is phenyl; and
$R^3$ is —$CF_3$, which may be provided as trifluoroacetic acid salts. Examples of suitable compounds of Formula (I) are 1-(4-(5-(3-phenyl-4-(trifluoromethyl)isoxazol-5-yl)-1,2,4-oxadiazol-3-yl)benzyl)azetidine-3-carboxylic acid, 1-(4-(5-(5-phenyl-4-(trifluoromethyl)isoxazol-3-yl)-1,2,4-oxadiazol-3-yl)benzyl)azetidine-3-carboxylic acid, or pharmaceutically acceptable salts thereof. The method of the present embodiment includes administration of a therapeutically effect amount of a compound of Formula (I) or a pharmaceutically effective salt thereof.

The methods of treating $S1P_1$-associated conditions may comprise administering compounds of Formula (I) alone or in combination with each other and/or other suitable therapeutic agents useful in treating such conditions. Accordingly, "therapeutically effective amount" is also intended to include an amount of the combination of compounds claimed that is effective to act as an agonist at the $S1P_1$ receptor. The combination of compounds is preferably a synergistic combination. Synergy, as described, for example, by Chou et al., *Adv. Enzyme Regul.* 22:27-55 (1984), occurs when the effect of the compounds when administered in combination is greater than the additive effect of the compounds when administered alone as a single agent. In general, a synergistic effect is most clearly demonstrated at sub-optimal concentrations of the compounds. Synergy can be in terms of lower cytotoxicity, increased efficacy, or some other beneficial effect of the combination compared with the individual components.

Exemplary of such other therapeutic agents include corticosteroids or glucocorticoids such as dexamethasone, methylprednisolone, prednisolone, and prednisone; PDE4 inhibitors such as rolipram, cilomilast, roflumilast, and oglemilast; cytokine-suppressive anti-inflammatory drugs (CSAIDs) and inhibitors of p38 kinase, 4-substituted imidazo [1,2-A]quinoxalines as disclosed in U.S. Pat. No. 4,200,750; antibodies or fusion proteins directed to cell surface molecules such as CD2, CD3, CD4, CD8, CD20 such as RITUXAN®, CD25, CD30, CD40, CD69, CD80 (B7.1), CD86 (B7.2), CD90, CTLA, for example abatacept (ORENCIA®), or their ligands including CD154 (GP39, or CD40L); antibodies to, fusion proteins, or soluble receptors of human cytokines or growth factors, for example, TNF such as, infliximab (REMICADE®), etanercept (ENBREL®), adalimumab (HUMIRA®), LT, I1-1 such as anakinra (KINERET®) (an IL-1 receptor antagonist), IL-2, IL-4, IL-5, I1-6, such as CNTO 328 (a chimeric anti-IL-6 antibody), I1-7, I1-8, I1-12, I1-15, I1-16, I1-17, I1-21, I1-23 such as Ustekinumab (a human anti-IL-12/23 monoclonal antibody), and interferons such as interferon beta 1a (AVONEX®, REBIF®), interferon beta 1b (BETASERON®); integrin receptor antagonists such as TYSABRI®; polymeric agents such as glatiramer acetate (COPAXONE®); sulfasalazine, mesalamine, hydroxychloroquine, non-steroidal antiinflammatory drugs (NSAIDs) such as salicylates including aspirin, salsalate, and magnesium salicylate, and non-salicylates such as, ibuprofen, naproxen, meloxicam, celecoxib and rofecoxib; antiviral agents such as abacavir; antiproliferative agents such as methotrexate, mercaptopurine, leflunomide, cyclosporine, mycophenololate, FK506 (tacrolimus, PROGRAF®); cytotoxic drugs such as azathioprine and cyclophosphamide; nuclear translocation inhibitors, such as deoxyspergualin (DSG); gold containing products such as auronofin; penicllamine, and rapamycin (sirolimus or RAPAMUNE®) or derivatives thereof.

The above other therapeutic agents, when employed in combination with the compounds of the present invention, may be used, for example, in those amounts indicated in the Physicians' Desk Reference (PDR) or as otherwise determined by one of ordinary skill in the art. In the methods of the present invention, such other therapeutic agent(s) may be administered prior to, simultaneously with, or following the administration of the inventive compounds.

Methods of Preparation

The compounds of the present invention can be prepared in a number of ways well known to one skilled in the art of organic synthesis. The compounds of the present invention can be synthesized using the methods described below, together with synthetic methods known in the art of synthetic organic chemistry, or variations thereon as appreciated by those skilled in the art. Preferred methods include, but are not limited to, those described below. All references cited herein are hereby incorporated in their entirety by reference.

The compounds of this invention may be prepared using the reactions and techniques described in this section. The reactions are performed in solvents appropriate to the reagents and materials employed and are suitable for the transformations being effected. Also, in the description of the synthetic methods described below, it is to be understood that all proposed reaction conditions, including choice of solvent, reaction atmosphere, reaction temperature, duration of the experiment and work up procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents that are compatible with the reaction conditions will be readily apparent to one skilled in the art and alternate methods must then be used. This will sometimes require a judgment to modify the order of the synthetic steps or to select one particular process scheme over another in order to obtain a desired compound of the invention. It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene et al. (*Protective Groups In Organic Synthesis*, Third Edition, Wiley and Sons (1999)).

Compounds of Formula (I) may be prepared by reference to the methods illustrated in the following Schemes. As shown therein the end product is a compound having the same structural formula as Formula (I). It will be understood that any compound of Formula (I) may be produced by the schemes by the suitable selection of reagents with appropriate substitution. Solvents, temperatures, pressures, and other reaction conditions may readily be selected by one of ordinary skill in the art. Starting materials are commercially available or readily prepared by one of ordinary skill in the art. Constituents of compounds are as defined herein or elsewhere in the specification.

As shown in Scheme 1, the oxadiazole compounds of the present invention (1.4) may be prepared through the reaction of carboxylic acids (1.1) with N'-hydroxybenzimidamides (1.2) with a variety of coupling reagents (e.g., EDC, HOBt, BOP, BOP-Cl). Alternatively, the N'-hydroxybenzimidamides may be reacted with acid fluoride (1.5) or acid chloride compounds (1.6). In each case, the initially formed N'-acyloxybenzimidamides (1.3) may spontaneously convert to the oxadiazoles under the reaction conditions. In cases where the N'-acyloxybenzimidamide (1.3) does not cyclize spontaneously, it may be isolated and subjected to reaction conditions to effect the cyclodehydration to 1.4. Such conditions include heating (either conventional or microwave), or treatment with fluoride source (such as tetrabutyl ammonium fluoride).

Scheme 1

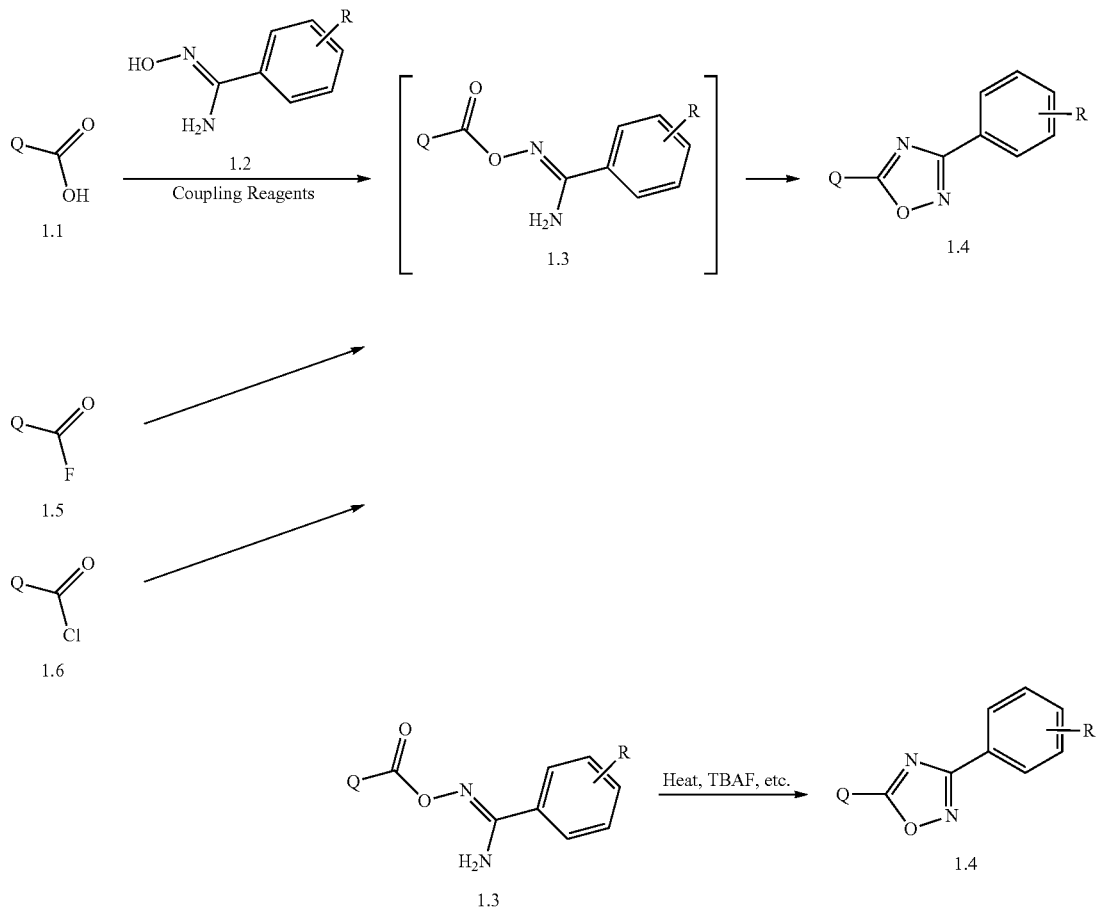

Compounds of formula (I) may be prepared through the reaction of acids (1.1), acid fluorides (1.5) or acid chlorides (1.6) with (Z)-tert-butyl 1-(4-(N'-hydroxycarbamimidoyl)benzyl)azetidine-3-carboxylate (2.1) via means described above to produce compounds of structure 2.2. Deprotection of tert-butyl ester derivatives (2.2) by treatment with an acid (for example trifluoroacetic acid) provides compounds of Formula (I).

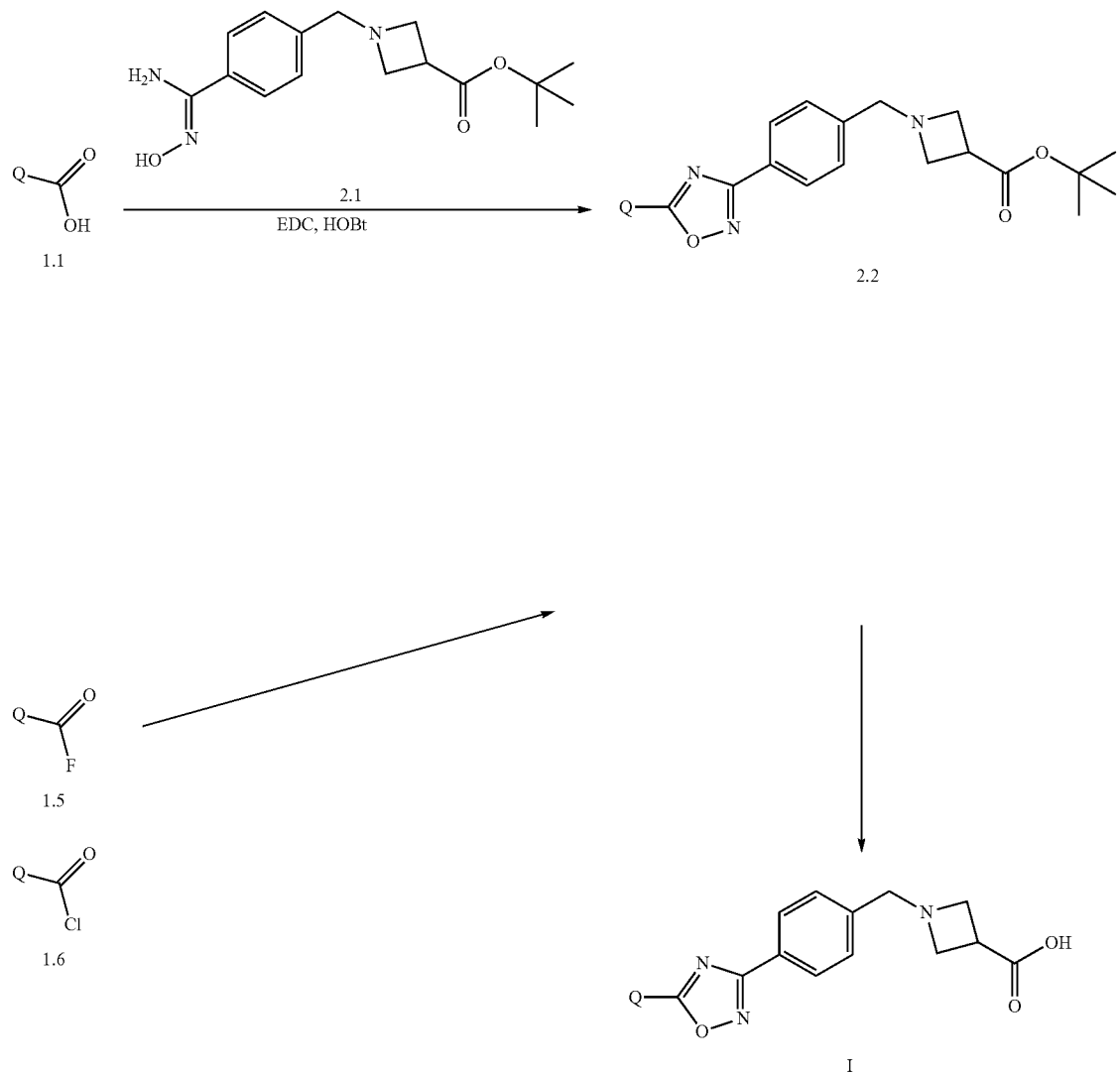

Scheme 2

Alternatively, compounds of Formula (I) may also be produced as described in Scheme 3. The reaction of acids (1.1) acid fluorides (1.5) or acid chlorides (1.6) with (Z)-N'-hydroxy-4-(hydroxymethyl)benzimidamide (3.2)) via means described above can produce compounds of structure 3.3 which, after oxidation to the corresponding aldehyde (3.4), can undergo reductive amination with azetidine-3-carboxylic acid (3.5) or tert-butyl azetidine-3-carboxylate (3.6) to provide compounds of Formula (I) or 2.2 respectively. Compound 2.2 may be converted to compounds of Formula (I) as described above.

Scheme 3

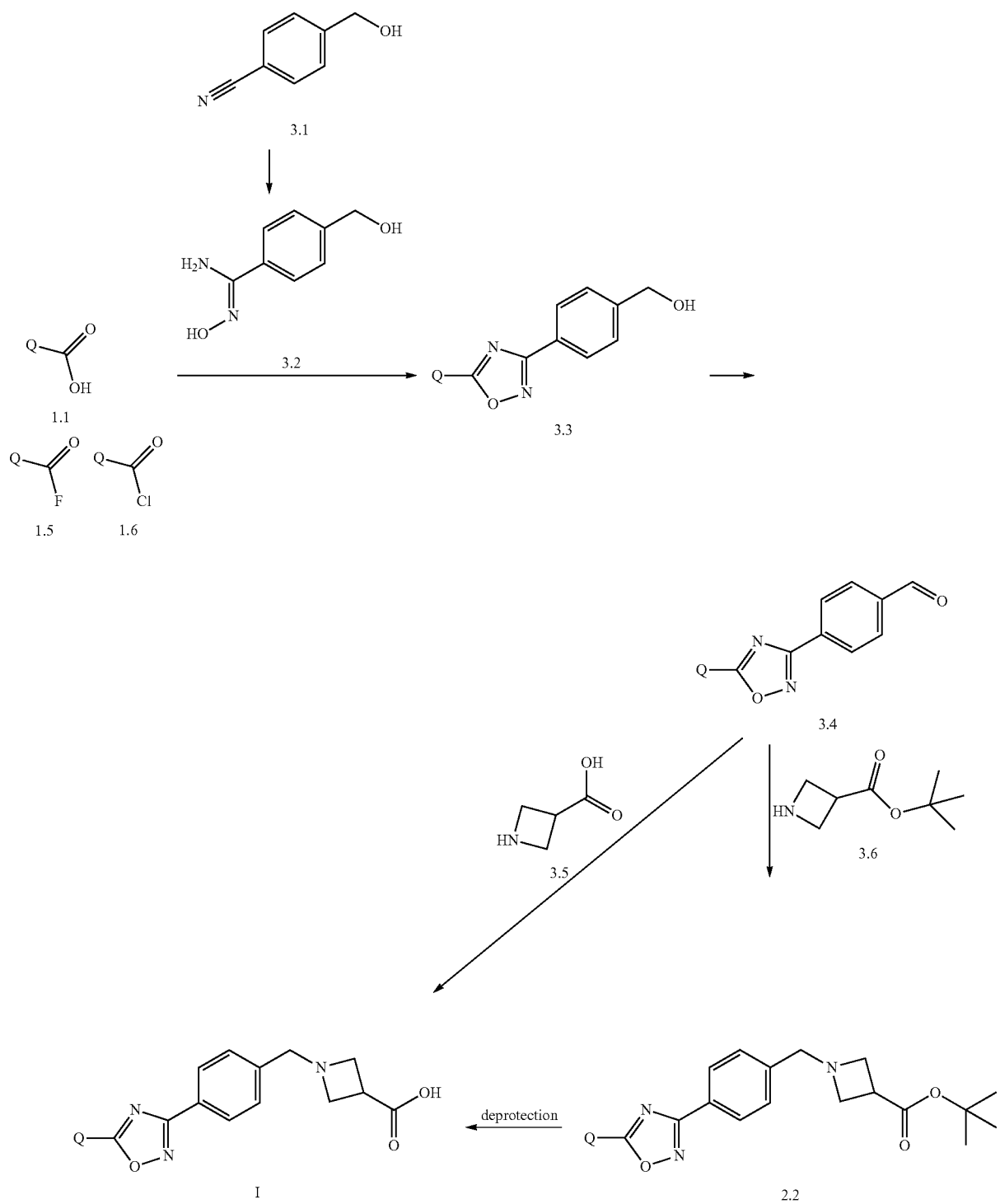

tert-Butyl azetidine-3-carboxylate (3.6) may be prepared from azetidine-3-carboxylic acid (3.5) via protection of the amine (for example with the CBZ group) followed by esterification of the acid with tert-butyl alcohol in the presence of a coupling reagent (for example CDI) and then removal of the amine protecting group. (Z)-tert-butyl 1-(4-(N'-hydroxycarbamimidoyl)benzyl)azetidine-3-carboxylate (2.1) is available from the reaction of tert-butyl azetidine-3-carboxylate (3.6) with 4-formylbenzonitrile (4.2) under reducing conditions to give 4.3, which is then reacted with hydroxylamine. Alternatively, compound 4.3 may be prepared by esterification of 4.5, which is obtained from the reaction of azetidine-3-carboxylic acid (3.5) with 4-formylbenzonitrile (4.2) under reducing conditions.

Scheme 4

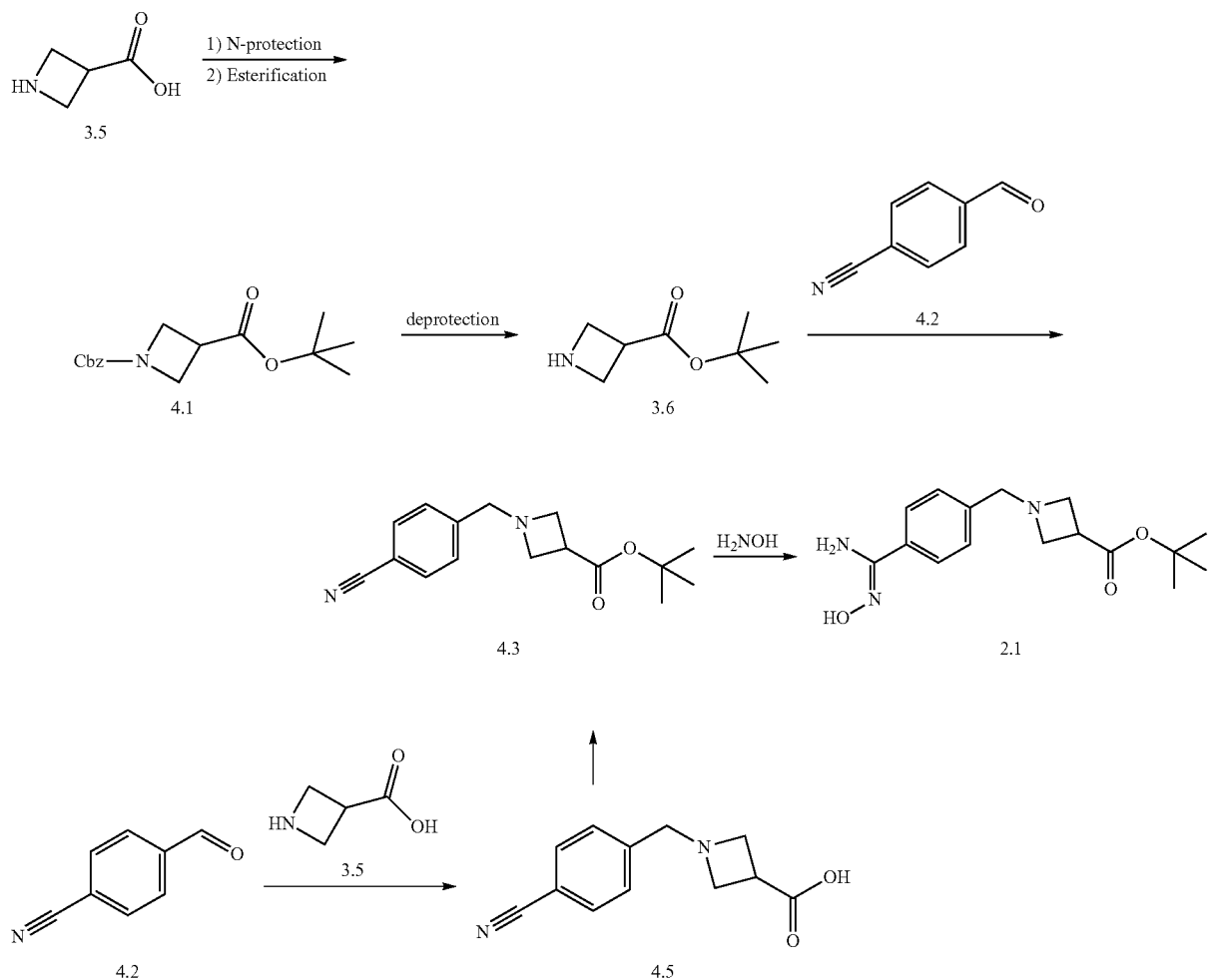

The carboxylic acid fragments (1.1) of the present invention may be prepared by a variety of methods, including those illustrated in Scheme 5 for the isoxazoles bearing the carboxylic acid group at the 5-position. Reaction of chloro-oxime 5.1 with substituted propiolates (5.2) under basic conditions provides a mixture of isoxazole carboxylates (5.3/5.4) generally in favor of isomer 5.3. After separation of the isomers (such as by silica gel chromatography or reverse phase preparative HPLC), 5.4 may be hydrolyzed to give the required isoxazole carboxylic acid (5.5). Reaction of chloro-oxime 5.1 with substituted propargylic alcohols (5.6) under basic conditions provides a mixture of isoxazole carboxylates (5.7/5.8) generally in favor of isomer 5.8. After separation of the isomers (such as by silica gel chromatography or reverse phase preparative HPLC), 5.8 may be oxidized to give acid 5.5. Esters 5.4 may also be obtained regioselectively through the reaction of 5.1 with substituted 2-bromo-acrylates (5.9). When chloro-oximes 5.1 are reacted with unsubstituted propiolates (5.10), isoxazoles 5.11 are produced regioselectively. The unsubstituted isoxazole position may then be converted to a halogenated derivative (5.12) which may then be used for further transformations including but not limited to transition metal cross coupling reactions or insertion reaction.

Scheme 5

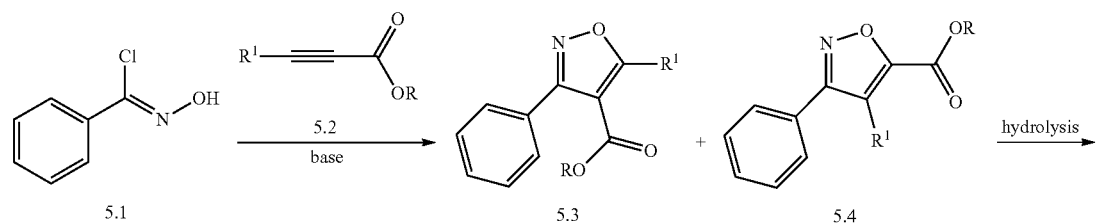

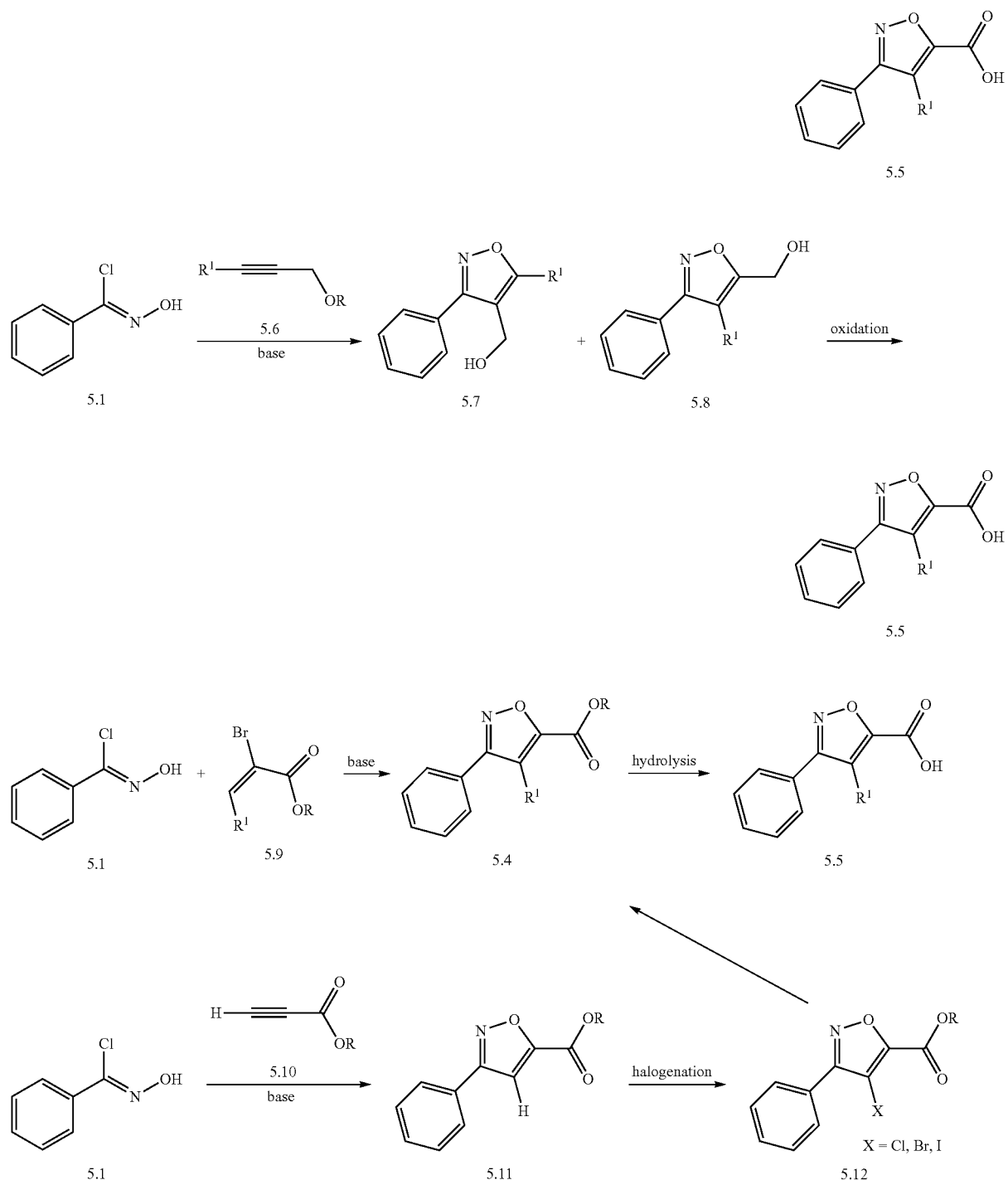

Illustrated in Scheme 6 are approaches for the isoxazoles bearing the carboxylic acid group at the 3-position. Isoxazole-3-carboxylic esters (6.3) may be prepared from the reaction of internal alkynes (6.1) with dimethyl 2-nitromalonate (6.2) under thermal decomposition conditions (heating in an inert solvent or neat) or reaction with chloro-oximes 6.5 under basic conditions. Hydrolysis of the esters (6.3) then provides the acids (6.4). The reaction of terminal alkynes (6.8) with chloro-oximes 6.5 leads to isoxazole esters lacking substitution at the 4-position. The unsubstituted isoxazole position may then be converted to a halogenated derivative (6.7) which may then be used for further transformations including but not limited to transition metal cross coupling reactions or insertion reactions.

Scheme 6

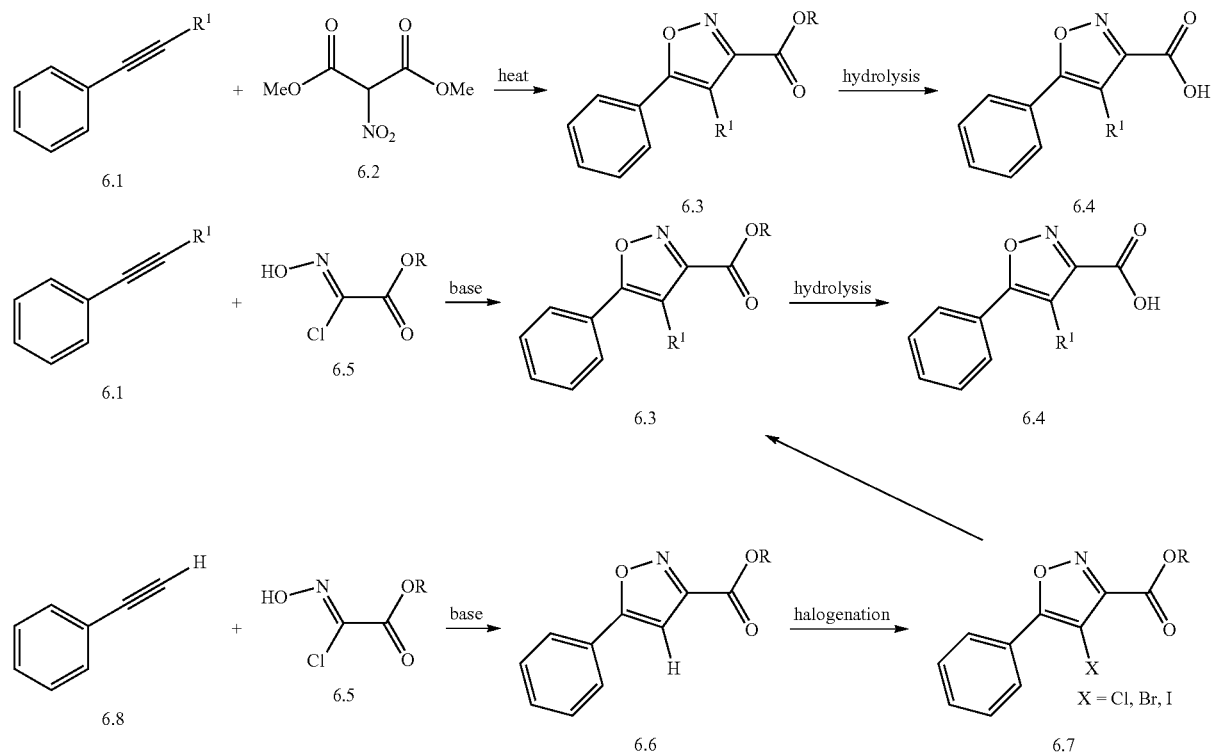

ABBREVIATIONS

Ac acetyl
AcOH acetic acid
aq. aqueous
CDI carbonyldiimidazole
Bn benzyl
Bu butyl
Boc tert-butoxycarbonyl
BOP-Cl bis-(2-oxo-3-oxazolidinyl)phosphinic chloride
DMA N,N-dimethylacetamide
DMAP dimethylaminopyridine
DMF dimethylformamide
DMSO dimethylsulfoxide
EDC 1-(3-Dimethylaminopropyl)-3-ethylcarbodiimide hydrochloride
EtOAc ethyl acetate
Et ethyl
EtOH ethanol
H hydrogen
h hour(s)
i iso
HMPA hexamethylphosphorus triamide
HOBt hydroxybenzotriazole
HPLC high pressure liquid chromatography
HOAc acetic acid
LC liquid chromatography
Me methyl
MeOH methanol
min. minute(s)
$M^{+1}$ $(M+H)^+$
MS mass spectrometry
n normal
PhCONCS benzyolyisothiocyanate
Pd/C palladium on carbon
Ph phenyl
Pr propyl
PSI pounds per square inch
Ret Time retention time
rt or RT room temperature
sat. saturated
t tertiary
TFA trifluoroacetic acid
THF tetrahydrofuran
Phenomenex Phenomenex, Macclesfield, Cheshire, UK
YMC YMC, Inc, Wilmington, N.C. 20403

EXAMPLES

The following Examples illustrate the particular and preferred embodiments of the present invention and do not limit the scope of the present invention. Chemical abbreviations and symbols as well as scientific abbreviations and symbols have their usual and customary meanings unless otherwise specified. Additional abbreviations employed in the Examples and elsewhere in this application are defined above. Common intermediates are generally useful for the preparation of more than one Example and are identified sequentially (e.g., Intermediate 1, Intermediate 2, etc. and are abbreviated as Int.1, Int.2, etc. In some instances the preparation of common intermediates may require multiple steps to be prepared. Each step is identified by the common intermediate and the step (e.g., Int.1-A, Int.1-B, and so forth. Compounds of the Examples are identified by the example and step in which they were prepared (e.g., "1-A" denotes the Example 1, step A), or by the example only where the compound is the title compound of the example (for example, "1" denotes the title compound of Example 1). In some instances alternate preparations of intermediates or Examples are described. Frequently chemists skilled in the art of synthesis may devise alternative preparations which may be desirable based on one or more considerations such as shorter reaction time, less expensive starting materials, ease of operation, amenable to catalysis, avoidance of toxic reagents, accessibility of specialized instrumentation, and decreased number of linear steps, etc. The intent of describing alternative preparations is to further enable the preparation of the Examples of this invention.

Those experiments specifying that they were performed in a microwave oven were conducted in a SmithSynthesizer oven manufactured by Personal Chemistry or a Discover microwave oven manufactured by CEM corporation. The microwave ovens generate a temperature which can be selected to be between 60-250° C. The microwave ovens automatically monitor the pressure which is between 0-300 PSI. Reaction hold times and temperature set points are reported.

Preparation of Intermediate 1 (Int.1)

tert-Butyl 1-(4-(N'-hydroxycarbamimidoyl)-benzyl) azetidine-3-carboxylate

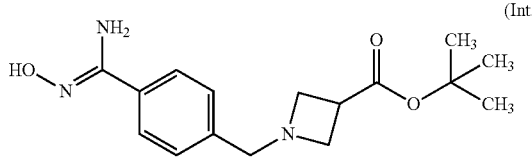

(Int.1)

Int.1-A.
1-(Benzyloxycarbonyl)azetidine-3-carboxylic acid

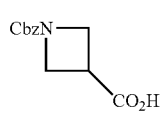

(Int.1-A)

To a solution of azetidine-3-carboxylic acid (88 g, 0.871 mol) and sodium bicarbonate (161 g, 1.92 mol) in water (1.75 L) at room temperature was added a solution of benzyl 2,5-dioxopyrrolidin-1-ylcarbonate (239 g, 0.959 mol) in tetrahydrofuran (3.5 L). The reaction mixture was stirred at room temperature overnight. The solvent was removed under reduced pressure, and the aqueous layer was washed with ethyl acetate (2×500 mL). The aqueous layer was acidified with a 1.0 N aqueous hydrochloric acid solution and was then extracted with ethyl acetate (3×750 mL). The organic layer was washed with water, followed by brine, and dried over anhydrous sodium sulfate. Concentration under reduced pressure afforded 1-(benzyloxycarbonyl) azetidine-3-carboxylic acid as colorless oil (202 g, 99% yield). The compound had an HPLC retention time=2.27 min.–Column: YMC COMBISCREEN® ODS-A 4.6×50 mm (4 min.); Solvent A=10% MeOH, 90% $H_2O$, 0.1% TFA; Solvent B=90% MeOH, 10% $H_2O$, 0.1% TFA. LC/MS $M^{+1}$=236.15. $^1$H NMR (400 MHz, $CDCl_3$) δ ppm 3.39-3.49 (m, 1H), 4.22 (d, J=7.28 Hz, 4H), 5.11 (s, 2H), and 7.29-7.39 (m, 5H).

Int.1-B. 1-Benzyl 3-tert-butyl azetidine-1,3-dicarboxylate

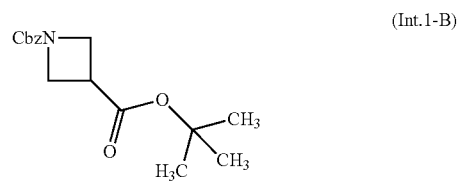 [SMILES: CC(C)(C)OC(=O)C1CN(C(=O)OCc2ccccc2)C1]

(Int.1-B)

To a solution of 1-(benzyloxycarbonyl)azetidine-3-carboxylic acid (200 g, 0.851 mol) in dichloromethane (6.0 L) at 0° C. was added t-butanol (158 g, 2.13 mol), DMAP (52.0 g, 0.425 mol), and EDCI (163 g, 0.853 mol). The reaction mixture was stirred at room temperature overnight. Next, the reaction mixture was concentrated and the residue was dissolved in ethyl acetate. The organic layer washed with 10% aqueous citric acid, 10% aqueous sodium bicarbonate solution, and brine. Drying over anhydrous sodium sulfate and concentration under reduced pressure afforded 1-benzyl-3-tert butyl-azetidine-1,3-dicarboxylate (200 g, 81% yield) as a colorless oil. The compound had an HPLC retention time=3.27 min.–Column: YMC COMBISCREEN® ODS-A 4.6×50 mm (4 min.); Solvent A=10% MeOH, 90% $H_2O$, 0.1% TFA; Solvent B=90% MeOH, 10% $H_2O$, 0.1% TFA. LC/MS $M^{+1}$=292.15. $^1$H NMR (400 MHz, $CDCl_3$) δ ppm 1.46 (s, 9H), 3.24-3.33 (m, 1H), 4.14 (d, J=7.53 Hz, 4H), 5.10 (s, 2H), and 7.30-7.39 (m, 5H).

Int.1-C. tert-Butyl azetidine-3-carboxylate

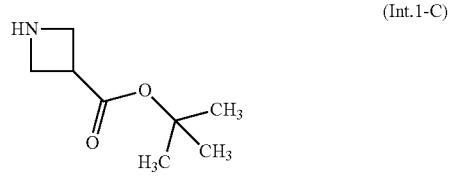

(Int.1-C)

A mixture of 1-benzyl-3-tert-butyl-azetidine-1,3-dicarboxylate (140 g, 0.480 mol) and 10% palladium on carbon (28.0 g) in ethyl acetate (1.40 L) was placed in an autoclave under 3.0 kg/cm² of hydrogen pressure overnight. The reaction mixture was filtered through CELITE®, and the CELITE® bed was washed with ethyl acetate. Acetic acid (28.9 g, 0.480 mol) was added to the filtrate and it was concentrated under reduced pressure maintaining the temperature below 50° C. to give tert-butyl azetidine-3-carboxylate acetic acid salt (96 g, 92% yield) as a colorless oil.

$^1$H NMR (400 MHz, $CDCl_3$) δ ppm 1.47 (s, 9H), 2.02 (s, 3H), 3.52-3.63 (m, 1H), and 4.00-4.10 (m, 4H).

Int.1-D. tert-Butyl 1-(4-cyanobenzyl)azetidine-3-carboxylate

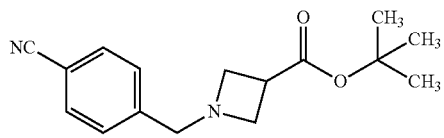
(Int.1-D)

To a solution of tert-butyl azetidine-3-carboxylate acetic acid salt (92.0 g, 0.423 mol) in methanol (1.0 L) at room temperature was added 4-formylbenzonitrile (50.8 g, 0.381 mol). The reaction mixture was cooled to 0° C., and sodium cyanoborohydride (28.8 g, 0.458 mol) was added portionwise. The reaction mixture was allowed to warm to room temperature and stirring continued overnight. After the reaction mixture was concentrated under reduced pressure the residue was diluted with 10% aqueous sodium bicarbonate solution and extracted with ethyl acetate. The organic layer was collected, washed with brine, and dried over anhydrous sodium sulfate. Concentration under reduced pressure followed by purification by silica gel chromatography using 20% ethyl acetate in petroleum ether afforded tert-butyl 1-(4-cyanobenzyl)azetidine-3-carboxylate (89%) (After chromatography, Int.1-D contained a small amount of 4-hydroxymethylbenzonitrile. This material was taken forward to the next step without further purification). LC/MS $M^{+1}$=273.18. $^1$H NMR (400 MHz, CDCl$_3$) δ ppm 1.46 (s, 9H), 3.22-3.31 (m, 3H), 3.48-3.56 (m, 2H), 3.66 (s, 2H), 7.39 (d, J=8.28 Hz, 2H), and 7.60 (d, J=8.28 Hz, 2H).

Int.1. Preparation of tert-butyl 1-(4-(N'-hydroxycarbamimidoyl)benzyl)azetidine-3-carboxylate

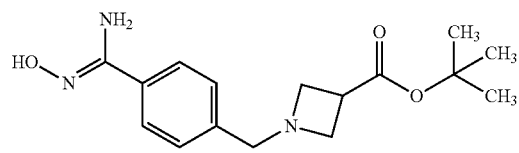
(Int.1)

To tert-butyl-1-(4-cynaobenzyl)azetidine-3-carboxylate (89.0 g, 0.326 mol) in tert-butanol (1.30 L) was added sodium bicarbonate (109.8 g, 1.31 mol) and hydroxylamine hydrochloride (45.5 g, 0.654 mol). The reaction was heated at reflux for 7 h and then cooled to room temperature and stirred overnight. The reaction mixture was diluted with water and extracted with ethyl acetate. The organic layer was collected, washed with water, washed with brine, then dried over anhydrous sodium sulfate. Concentration followed by purification by silica gel chromatography using 2.5% methanol in chloroform containing 0.2% triethylamine as eluent afforded (Z)-tert-butyl 1-(4-(N'-hydroxycarbamimidoyl)benzyl)azetidine-3-carboxylate (64 g, 0.210 mol, 55% yield over 2 steps). The compound had an HPLC retention time=7.03 min.–Column. XBridge Phenyl 150×4.6 mm 3.5 u, SC/749. 1 mL/min. Solvent A=5% MeCN, 95% H$_2$O, 0.05% TFA; Solvent B=95% MeCN, 5% H$_2$O, 0.05% TFA. Time/% B: 0 min/0%, 15 min/50%, 18 min/100%, 20 min/100%. LC/MS $M^{+1}$=306.2. $^1$H NMR (400 MHz, CDCl$_3$) δ ppm 1.45 (s, 9H), 3.23-3.30 (m, 3H), 3.49-3.57 (m, 2H), 3.63 (s, 2H), 4.85 (s, 2H), 7.31 (d, J=8.28 Hz, 2H), and 7.57 (d, J=8.28 Hz, 2H).

Alternative Preparation of Int.1-D: tert-Butyl 1-(4-cyanobenzyl)azetidine-3-carboxylate

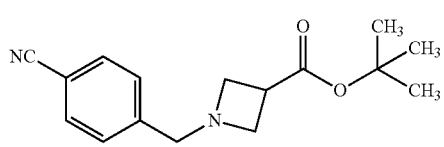
(Int. 1-D)

Int.1-E. 1-(4-Cyanobenzyl)azetidine-3-carboxylic acid

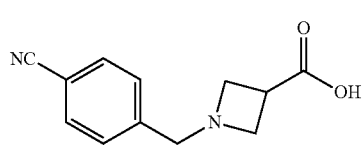
(Int. 1-E)

A mixture of 4-formylbenzonitrile (2.88 g, 22.0 mmol), azetidine-3-carboxylic acid (2.02 g, 20 mmol), and acetic acid (1.15 mL, 20.0 mmol) in dichloromethane (20 mL) and methanol (80 mL) was stirred at room temperature for 1 h. Sodium triacetoxyborohydride (6.78 g, 32.0 mmol) was added and stirring was continued at room temperature for 18 hr. The volatiles were removed under reduced pressure, and the residue was partitioned between water (50 mL) and diethyl ether (50 mL). The aqueous layer was collected, washed with diethyl ether (50 mL), and concentrated. The residue was dissolved in water (20 mL) and loaded onto a 2.5×20 cm HP-20 column. Preparation of HP-20 Gel: approximately 400 ml of dry, unused MCI CHP-20 Gel (75-150 micron) was swelled in methanol for 24 hrs. The gel was filtered and rinsed with 1 liter of methanol. It was then transferred to a bottle for storage under methanol. Immediately before use, the desired amount of gel was rinsed thoroughly with 20 volumes of water]. The column was eluted with 240 mL of water and 400 mL of methanol. The product containing fractions were concentrated and co-evaporated from ethanol and ethyl acetate/heptane to afford 1-(4-cyanobenzyl)azetidine-3-carboxylic acid (3.25 g, 15.0 mmol, 75% yield) as a white solid. MS: (M+H)=217.18. $^1$H NMR (400 MHz, MeOD) δ ppm 3.39 (m, 1H), 4.08 (m, 4H), 4.32 (s, 2H), 7.63 (d, J=8.3 Hz, 2H), and 7.82 (d, J=8.3 Hz, 2H).

Int.1-Alt.1-D. tert-Butyl 1-(4-cyanobenzyl)azetidine-3-carboxylate

(Int. 1-D)

To a mixture of 1-(4-cyanobenzyl)azetidine-3-carboxylic acid (3.25 g, 15.0 mmol), DMAP (1.84 g, 15.0 mmol), and tert-butanol (14.1 mL, 150 mmol) in dichloroethane (150 mL) was added EDCI (4.32 g, 22.5 mmol), and the reaction mixture was allowed to stir over the weekend. The volatiles were removed under reduced pressure, and the residue was partitioned between ethyl acetate (250 mL) and a saturated aqueous solution of sodium bicarbonate (250 mL). The organic layer was washed with water (250 mL), washed with brine (100 mL), and dried over anhydrous magnesium sulfate. Concentration under reduced pressure afforded a light yellow oil which was chromatographed on a 5×15 cm silica gel column, eluting with a 0-40% ethyl acetate/hexane gradient to give tert-butyl 1-(4-cyanobenzyl)azetidine-3-carboxylate (3.5 g, 12.9 mmol, 86% yield) as a colorless liquid. HPLC retention time=1.38 minutes–Column: YMC-Combi 4.6×50 mm S-5 ODS column) eluting with 10-90% aqueous methanol+0.2% phosphoric acid over a 4 minute gradient. MS: (M+H)=273.18. $^1$H NMR (400 MHz, CDCl$_3$) δ ppm 1.46 (s, 9H), 3.26 (m, 3H), 3.52 (m, 2H), 3.66 (s, 2H), 7.39 (d, J=8.3 Hz, 2H), and 7.60 (d, J=8.3 Hz, 2H).

Example 1

1-(4-(5-(3-Phenyl-4-(trifluoromethyl)isoxazol-5-yl)-1,2,4-oxadiazol-3-yl)benzyl)azetidine-3-carboxylic acid

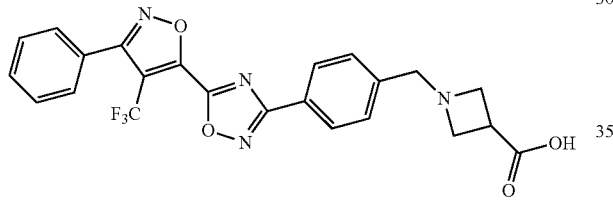

(1)

1-A. 4,4,4-Trifluorobut-2-yn-1-ol

(1-A)

To a solution of diisopropylamine (24.7 mL, 176 mmol) in ether (100 mL) at −78° C. was added a 10M solution of butyllithium in ether (17.6 mL, 176 mmol) over 5 min. After 10 min. at −78° C., 2-bromo-3,3,3-trifluoroprop-1-ene (14.0 g, 80 mmol) was added to the pale yellow solution. After an additional 10 min., paraformaldehyde (2.40 g, 80 mmol) was added, the dry-ice bath was removed, and the reaction mixture was stirred at room temperature overnight. As the reaction mixture approached room temperature, it became dark in color. The reaction was quenched with a 1N aqueous solution of hydrochloric acid (100 mL), diluted with ether (500 mL), washed with a 1N aqueous solution of hydrochloric acid (2×100 mL), washed with brine 100 mL, and dried over anhydrous sodium sulfate. Concentration under reduced pressure afforded a dark liquid which was distilled under low-vacuum (~50 Torr, ~50° C.) to give 4,4,4-trifluorobut-2-yn-1-ol (7.1 g, 57.2 mmol, 72% yield) as a pale yellow liquid. $^1$H NMR (500 MHz, CDCl$_3$) δ ppm 2.31 (br. s., 1H) and 4.38-4.42 (m, 2H).

An Alternative Preparation of 1-A:
4,4,4-Trifluorobut-2-yn-1-ol

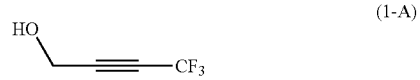

(1-A)

To an ether (pre-dried over magnesium sulfate) solution of phenanthroline (2.16 mg, 0.012 mmol) (indicator) at −78° C. under nitrogen was added a 2M solution of n-butyl lithium in pentane. An orange color immediately appeared. Trifluoromethylacetylene gas was bubbled through the solution at −78° C. After ~4 min. of gas introduction, the orange color almost completely disappeared, the reaction solution became cloudy (due to some precipitation), and a pale light orange color persisted. Paraformaldehyde was added, and the dry ice/isopropanol bath was removed after 5 min. and replaced with a 0° C. ice-bath. Stirring was continued for 45 min., the ice bath was removed, and stirring was continued for an additional 1.25 h. The reaction flask was immersed in a 0° C. ice bath, and a saturated aqueous solution of ammonium chloride (20.0 mL) was added. The layers were separated, and the organic layer was washed with water (2×), washed with brine, and dried over anhydrous sodium sulfate. Concentration under low-vacuum (~50 Torr) without heat afforded a dark brown liquid which was purified by vacuum distillation (~50 Torr, ~50° C.) to give 4,4,4-trifluorobut-2-yn-1-ol (7.1 g, 57.2 mmol, 72% yield) as a colorless liquid.

1-B. N-Hydroxybenzimidoyl chloride

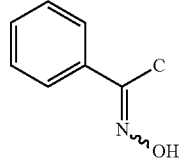

(1-B)

This compound was prepared according to the method of Liu, K. C. et al., *J. Org. Chem.*, 45:3916-1918 (1980).

To a colorless, homogeneous solution of (E)-benzaldehyde oxime (24.4 g, 201 mmol) in N,N-dimethylformamide (60 mL) at room temperature was added N-chlorosuccinimide (26.9 g, 201 mmol) portion-wise over 30 min. During each addition, the reaction mixture would turn yellow and then gradually return to near colorlessness. Additionally, an exotherm was noted with each portion added to ensure that the reaction initiated after the addition of N-chlorosuccinimide. An ice bath was available, if required, to cool the exotherm. After the addition was complete, the homogeneous reaction mixture was stirred overnight at room temperature. The reaction mixture was diluted with 250 mL of water and extracted with ether (3×100 mL). The organic layers were combined, washed with water (2×100 mL), washed with a 10% aqueous solution of lithium chloride (2×100 mL), and washed with brine (100 mL). The aqueous layers were back extracted with ether (100 mL), and the combined organic layers (400 mL) were dried over anhydrous sodium sulfate. Concentration under reduced pressure afforded (Z)-N-hydroxybenzimidoyl chloride (30.84 g, 198 mmol, 98% yield) as a fluffy, pale yellow solid. The product had an HPLC ret. time=1.57 min.−

Column. CHROMOLITH® SpeedROD 4.6×50 mm (4 min.); Solvent A=10% MeOH, 90% H$_2$O, 0.1% TFA; Solvent B=90% MeOH, 10% H$_2$O, 0.1% TFA. LC/MS M$^{+1}$=155.8. $^1$H NMR (500 MHz, DMSO-d$_6$) δ ppm 7.30-7.64 (m, 3H), 7.73-7.87 (m, 2H), and 12.42 (s, 1H).

1-C.
3-Phenyl-4-(trifluoromethyl)isoxazol-5-yl)methanol

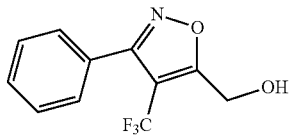

(1-C)

To a pale yellow, homogeneous mixture of N-hydroxybenzimidoyl chloride (5.50 g, 35.4 mmol) and 4,4,4-trifluorobut-2-yn-1-ol (5.46 g, 39.6 mmol) in dichloroethane (85 mL) in a 250 mL round bottom flask at 70° C. was added triethylamine (9.85 mL, 70.7 mmol) in 22 mL of dichloroethane over 2.5 h via an addition funnel (the first ~50% over 2 h and the remaining 50% over 0.5 h). After the addition was complete, the reaction mixture was complete by HPLC (total time at 70° C. was 3 h). The reaction mixture was stirred at room temperature overnight.

The reaction mixture was diluted with dichloromethane (100 mL), washed with water (100 mL), and the organic layer was collected. The aqueous layer was extracted with dichloromethane (2×50 mL), and the combined organic layers were dried over anhydrous sodium sulfate. The solvent was removed under reduced pressure. Analysis indicated that the product mixture was composed of a 86:14 mixture of the desired regioisomer (1-C), (3-phenyl-4-(trifluoromethyl)isoxazol-5-yl)methanol, and the undesired regioisomer, (3-phenyl-5-(trifluoromethyl)isoxazol-4-yl)methanol. The mixture was purified by silica gel chromatography using a mixture of ethyl acetate and hexane (1% to pack and load—5%-9%-12%) to afford (3-phenyl-4-(trifluoromethyl)isoxazol-5-yl)methanol (5.34 g, 21.96 mmol, 62.1% yield) as a pale yellow oil. The compound had an HPLC ret. time=1.91 min.–Column: CHROMOLITH® SpeedROD 4.6×50 mm (4 min.); Solvent A=10% MeOH, 90% H$_2$O, 0.1% TFA; Solvent B=90% MeOH, 10% H$_2$O, 0.1% TFA. LC/MS M$^{+1}$=244.2. $^1$H NMR (500 MHz, CDCl$_3$) δ ppm 2.21 (br. s., 1H), 4.97 (s, 2H), 7.47-7.56 (m, 3H), and 7.65 (d, J=6.60 Hz, 2H).

1-D. 3-Phenyl-4-(trifluoromethyl)isoxazole-5-carboxylic acid

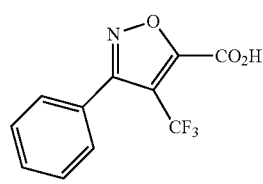

(1-D)

Preparation of Jones' Reagent

To an orange, homogeneous solution of chromium trioxide (12.4 g, 0.123 mol) in water (88.4 mL) at 0° C. was added sulfuric acid (10.8 mL) dropwise via addition funnel over 30 min. with stirring. The addition funnel was rinsed with water (1 mL) to give 1.23 M solution of Jones' Reagent (0.123 mol of reagent in 100 mL of solvent).

To a solution of (3-phenyl-4-(trifluoromethyl)isoxazol-5-yl)methanol (5.24 g, 21.6 mmol) in acetone (75 mL) at room temperature (immersed in a water bath) was added Jones' Reagent (43.8 mL, 53.9 mmol) via addition funnel slowly over 1.5 h. The dark reaction mixture was stirred at room temperature overnight. By HPLC, the reaction was 93% complete. An additional 0.5 equivalents (9 mL) of the Jones' Reagent was added. After 1 h, the reaction was 95% complete. After an additional 3 h, the reaction was 96% complete. An additional 0.5 equivalents (9 mL) of the Jones' Reagent was added. The reaction mixture was stirred for an additional 2.5 h. By HPLC, the reaction was 97% complete. Isopropyl alcohol (6 mL) was added, and the mixture was stirred for 90 min, resulting in a dark green precipitate. The mixture was diluted with ether (600 mL), washed with a 2% aqueous solution of sodium hydrogen sulfite (5×100 mL), and the organic layer was collected. The aqueous layer was back-extracted with ether (2×100 mL). By HPLC, there was no additional product in the aqueous layer. The combined organic layers were washed with water (100 mL), washed with a saturated aqueous solution of brine (100 mL), and dried over anhydrous sodium sulfate. The aqueous layer was back-extracted with ether (100 mL), and the organic layer was added to the previous organic layers. The solution was concentration under reduced pressure to give 3-phenyl-4-(trifluoromethyl)isoxazole-5-carboxylic acid as an off-white solid. The solid was diluted with dichloromethane (200 mL), washed with a 2% aqueous solution of sodium hydrogen sulfite, washed with brine, and dried over anhydrous sodium sulfate. Concentration under reduced pressure afforded 3-phenyl-4-(trifluoromethyl)isoxazole-5-carboxylic acid (3.84 g, 14.93 mmol, 69.3% yield) as a pale yellow solid. The product was 96% pure by HPLC with a ret. time=1.60 min.–Column. CHROMOLITH® SpeedROD 4.6×50 mm (4 min.); Solvent A=10% MeOH, 90% H$_2$O, 0.1% TFA; Solvent B=90% MeOH, 10% H$_2$O, 0.1% TFA. LC/MS M$^{+1}$=258.2.

The sodium hydrogen sulfite aqueous layer still contained a significant amount of product. The brine layer contained no additional product and was discarded. The aqueous layer was saturated with sodium chloride, the pH was adjusted to ~3.5, and the solution was extracted with ether (3×100 mL). The organic layer was dried over anhydrous sodium sulfate and concentrated to afford additional 3-phenyl-4-(trifluoromethyl)isoxazole-5-carboxylic acid (1.12 g, 4.36 mmol, 20.21% yield) as a white solid. The product was >99% pure by HPLC with a ret. time=1.60 min.–Column. CHROMOLITH® SpeedROD 4.6×50 mm (4 min.); Solvent A=10% MeOH, 90% H$_2$O, 0.1% TFA; Solvent B=90% MeOH, 10% H$_2$O, 0.1% TFA. LC/MS M$^{+1}$=258.1. $^1$H NMR (500 MHz, DMSO-d$_6$) δ ppm 7.55-7.63 (m, 5H).

The products were combined to give 4.96 g (90% yield) of 3-phenyl-4-(trifluoromethyl)isoxazole-5-carboxylic acid.

An Alternative Preparation of 1-D: 3-Phenyl-4-(trifluoromethyl)isoxazole-5-carboxylic acid starting with (3-phenyl-4-(trifluoromethyl)isoxazol-5-yl)methanol

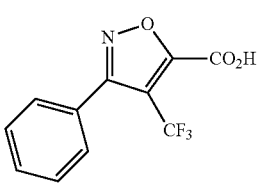

(1-D)

A mixture of (3-phenyl-4-(trifluoromethyl)isoxazol-5-yl)methanol (2.1 g, 8.64 mmol), TEMPO (0.094 g, 0.604 mmol), and a sodium phosphate buffer (0.67M) (32.2 mL, 21.59 mmol) was heated to 35° C. A solution of sodium phosphate buffer (40 mL, pH ~6.5) consisting of a 1:1 solution of NaH$_2$PO$_4$ (20 mL, 0.67M) and Na$_2$HPO$_4$ (20 mL, 0.67M) was prepared in acetonitrile (30 mL) was prepared prior to use. Solutions of sodium chlorite (3.91 g, 34.5 mmol) in water (4.5 mL) and bleach (4.3 mL, 6% wt.) were added simultaneously over 40 min. The reaction was monitored by HPLC, and after 2 h, ~30% of the starting material remained. After 6 h, 10% remained. Additional bleach (100 µL) was added, and the reaction mixture was left at room temperature overnight.

Additional bleach (100 µL) was added. The resulting mixture was allowed to stir at 35° C. for additional 2 h. HPLC indicated complete conversion. The reaction was quenched by the slow addition of a solution of sodium sulfite (2.07 mL, 43.2 mmol) in water (90 mL) at 0° C., resulting in the disappearance of the brown reaction color. The solvent was removed under reduced pressure, and the remaining aqueous residue was extracted with ethyl acetate (3×40 mL). The organic layers were combined, washed with water (8 mL), washed with brine (8 mL), and dried over anhydrous sodium sulfate. Concentration under reduced pressure afforded 3-phenyl-4-(trifluoromethyl)isoxazole-5-carboxylic acid (2.2 g, 8.55 mmol, 99% yield) as a pale yellow solid.

An alternative procedure for the for the preparation of 3-phenyl-4-(trifluoromethyl) isoxazole-5-carboxylic acid starting with 4,4,4-trifluorobut-2ynoate (1-D)

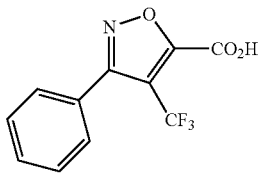

(1-D)

Alt.1-D-1. Ethyl 3-phenyl-4-(trifluoromethyl)isoxazole-5-carboxylate

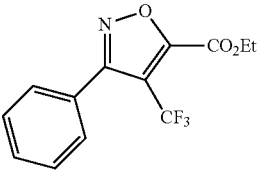

(1-D-1)

To a pale yellow mixture of (Z)-N-hydroxybenzimidoyl chloride (1.04 g, 6.68 mmol) and ethyl 4,4,4-trifluorobut-2-ynoate (1.238 g, 7.45 mmol) in diethyl ether (20 mL) at room temperature was added triethylamine (1.86 mL, 13.4 mmol) over 15 min., resulting in a precipitant. After the addition was complete, the pale yellow slurry was stirred at room temperature over a weekend. The heterogeneous reaction mixture was filtered under reduced pressure to remove the triethylamine hydrochloride salt, and the filtrate was concentrated to give the product mixture as a dark yellow, viscous oil (2.03 g). By HPLC, the reaction mixture was composed of a mixture of the desired regioisomer, ethyl 3-phenyl-4-(trifluoromethyl)isoxazole-5-carboxylate, and the undesired regioisomer, ethyl 3-phenyl-5-(trifluoromethyl)isoxazole-4-carboxylate, in an approximately 15:85 ratio. The compound mixture was dissolved in hexane and sonicated for 5 min. The hexane was decanted off, and the dark red, oily residue was found to have only trace product by HPLC. The hexane was removed under reduced pressure, and the residue (1.89 g) was purified by preparative HPLC. The desired fractions containing ethyl 3-phenyl-4-(trifluoromethyl)isoxazole-5-carboxylate were concentrated, and the residue was diluted with dichloromethane, washed with a saturated aqueous solution of sodium bicarbonate, and dried over anhydrous sodium sulfate. Concentration under reduced pressure afforded ethyl 3-phenyl-4-(trifluoromethyl) isoxazole-5-carboxylate (0.087 g, 0.305 mmol, 4.6% yield) as a pale yellow solid. The compound had an HPLC ret. time=2.88 min.–Column: CHROMOLITH® SpeedROD 4.6×50 mm (4 min.); Solvent A=10% MeOH, 90% H$_2$O, 0.1% TFA; Solvent B=90% MeOH, 10% H$_2$O, 0.1% TFA. $^1$H NMR (400 MHz, CDCl$_3$) δ ppm 1.46 (t, J=7.15 Hz, 3H), 4.53 (q, J=7.03 Hz, 2H), 7.48-7.55 (m, 3H), and 7.58 (d, J=7.53 Hz, 2H).

An Alternative Preparation of 1-D-1: Ethyl 3-phenyl-4-(trifluoromethyl)isoxazole-5-carboxylic acid starting with ethyl 4,4,4-trifluorobut-2-enoate 1-D-1. Ethyl 2,3-dibromo-4,4,4-trifluorobutanoate

(1-D-1)

Bromine (18.4 mL, 357 mmol) was added dropwise over 30 minutes to a solution of (E)-ethyl 4,4,4-trifluorobut-2-enoate (50 g, 297 mmol) in carbon tetrachloride (50 mL) at room temperature under nitrogen. The resulting dark red solution was refluxed for 4 hours. Additional bromine (2 ml) was added and heating was continued until the HPLC analysis showed that the starting material had been consumed. The reaction mixture was concentrated under reduced pressure to give light brown oil which used in the next step without purification. HPLC(XBridge 5µ C18 4.6×50 mm, 4 mL/min, Solvent A: 10% MeOH/water with 0.2% H$_3$PO$_4$, Solvent B: 90% MeOH/water with 0.2% H$_3$PO$_4$, gradient with 0-100% B over 4 minutes): 2.96 and 3.19 minutes.

1-D-2. (Z/E)-Ethyl 2-bromo-4,4,4-trifluorobut-2-enoate

(1-D-2)

To a solution of ethyl 2,3-dibromo-4,4,4-trifluorobutanoate (1-B-1) in hexane (200 mL) cooled to 0° C. was added triethylamine (49.7 ml, 357 mmol) drop-wise over 35 minutes, during which time a white precipitate formed. The reaction mixture was stirred for an additional 2 hours until LC indicated complete conversion. The solid was filtered and rinsed with hexane (3×50 mL), and the filtrate was concentrated and passed through a short silica gel pad eluting with 10% ethyl acetate/hexane to give (Z/E)-ethyl 2-bromo-4,4,4-trifluorobut-2-enoate (65.5 g, 265 mmol, 89% yield for two steps) as a colorless oil. Alternatively, the crude product can be purified by distillation (85° C./~60 mmHg). $^1$H NMR (CDCl$_3$, 400 MHz) δ 7.41 (q, 1H, J=7.28 Hz), 4.35 (q, 2H, J=7.11 Hz), 1.38 (t, 3H, J=7.15 Hz); HPLC(XBridge 5µ C18 4.6×50 mm, 4 mL/min, Solvent A: 10% MeOH/water with 0.2% H$_3$PO$_4$, Solvent B: 90% MeOH/water with 0.2% H$_3$PO$_4$, gradient with 0-100% B over 4 minutes): 3.09 minutes.

1-D-1. Ethyl 3-phenyl-4-(trifluoromethyl)isoxazole-5-carboxylate

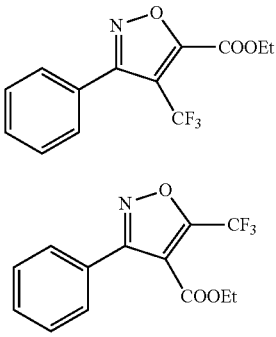

(Z/E)-Ethyl 2-bromo-4,4,4-trifluorobut-2-enoate, 1-D-3, (39.7 g, 161 mmol) and N-hydroxybenzimidoyl chloride (30 g, 193 mmol) were dissolved in ethyl acetate (150 mL). Indium (III) chloride (8.89 g, 40.2 mmol) was added and the resulting mixture stirred for 60 minutes at RT under N$_2$. Potassium hydrogen carbonate (32.2 g, 321 mmol) was added to the reaction mixture which was allowed to stir overnight for 14 hours at RT. The solvent was removed in vacuo. The residue was re-suspended in 300 mL hexane and stirred for 10 minutes then filtered. The filter cake was washed with hexane (3×30 mL) and the combined filtrate was concentrated in vacuo to give crude product, which was further purified with flash chromatography to generate 33 g product (72%) as light yellowish oil as a mixture of the desired isomer 1-D-1 and undesired isomer 1-D-1a in a ratio of ~30/1. MS m/e 286.06 (M+H$^+$); $^1$H NMR (CDCl$_3$, 400 MHz) δ 7.56 (m, 5H), 4.53 (q, 2H, J=7.3 Hz), 1.46 (t, 3H, J=7.2 Hz); HPLC(XBridge 5µ C18 4.6×50 mm, 4 mL/min, Solvent A: 10% MeOH/water with 0.2% H$_3$PO$_4$, Solvent B: 90% MeOH/water with 0.2% H$_3$PO$_4$, gradient with 0-100% B over 4 minutes): 3.57 minutes.

Alt.1-D. 3-Phenyl-4-(trifluoromethyl)isoxazole-5-carboxylic acid, lithium salt

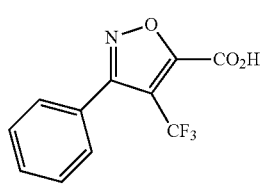

A mixture of ethyl 3-phenyl-4-(trifluoromethyl)isoxazole-5-carboxylate, 1-D-1, (0.085 g, 0.298 mmol) and lithium hydroxide hydrate (0.013 g, 0.298 mmol) in methanol (2.0 mL) and water (1.0 mL) was stirred at room temperature overnight. The reaction mixture was concentrated to dryness to give 3-phenyl-4-(trifluoromethyl)isoxazole-5-carboxylic acid, lithium salt (0.079 g, 0.299 mmol, 100% yield) as a pale yellow solid. The compound had an HPLC ret. time=1.72 min.–Column. CHROMOLITH® SpeedROD 4.6×50 mm (4 min.); Solvent A=10% MeOH, 90% H$_2$O, 0.1% TFA; Solvent B=90% MeOH, 10% H$_2$O, 0.1% TFA. LC/MS M$^{+1}$=258.0. $^1$H NMR (400 MHz, CDCl$_3$) δ ppm 7.49-7.57 (m, 3H) and 7.58-7.62 (m, 2H).

1-E. 3-Phenyl-4-(trifluoromethyl)isoxazole-5-carbonyl fluoride

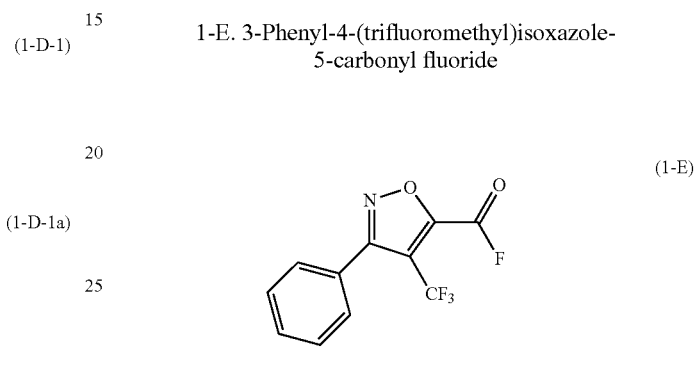

To a mixture of 3-phenyl-4-(trifluoromethyl)isoxazole-5-carboxylic acid (3.00 g, 11.7 mmol) and pyridine (1.132 mL, 14.0 mmol) in dichloromethane (100 mL) at room temperature was added 2,4,6-trifluoro-1,3,5-triazine (cyanuric fluoride) (1.18 mL, 14.0 mmol). The reaction mixture was stirred at room temperature overnight, diluted with dichloromethane (300 mL), washed with an ice-cold solution of 0.5N aqueous hydrochloric acid (2×100 mL), and the organic layer was collected. The aqueous layer was back-extracted with dichloromethane (200 mL), and the combined organic layers were dried anhydrous sodium sulfate and concentrated to afford 3-phenyl-4-(trifluoromethyl)isoxazole-5-carbonyl fluoride (2.91 g, 11.2 mmol, 96% yield) as a yellow, viscous oil. The product was found to react readily with methanol and on analysis was characterized as the methyl ester, which had an HPLC ret. time=2.56 min.–Column. CHROMOLITH® SpeedROD 4.6×50 mm (4 min.); Solvent A=10% MeOH, 90% H$_2$O, 0.1% TFA; Solvent B=90% MeOH, 10% H$_2$O, 0.1% TFA. LC/MS M$^{+1}$=272.3 (methyl ester).

1-F. tert-Butyl 1-(4-(5-(3-phenyl-4-(trifluoromethyl)isoxazol-5-yl)-1,2,4-oxadiazol-3-yl)-benzyl)azetidine-3-carboxylate

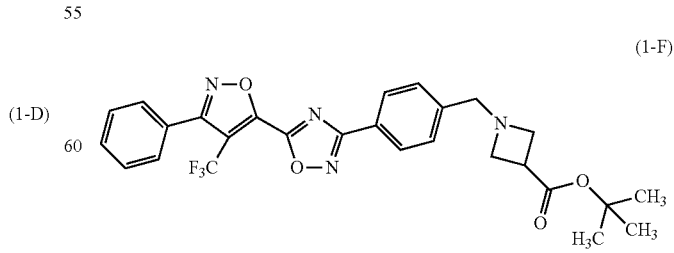

A suspension of 3-phenyl-4-(trifluoromethyl)isoxazole-5-carbonyl fluoride (2.91 g, 11.2 mmol), (Z)-tert-butyl 1-(4-

(N'-hydroxycarbamimidoyl)benzyl)azetidine-3-carboxylate (Int.1, 3.43 g, 11.2 mmol), and Hunig's Base (2.55 mL, 14.6 mmol) in acetonitrile (20 mL) was stirred at room temperature over the weekend. The reaction mixture had completely solidified (pinkish-tan in color), but was judged complete by HPLC and LCMS. The reaction mixture was partitioned between a saturated aqueous of sodium bicarbonate (150 mL) and dichloromethane (150 mL). The aqueous layer was extracted with dichloromethane (2×100 mL), and the combined organic layers were dried over anhydrous sodium sulfate. Concentration under reduced pressure afforded a tan solid which was purified by flash silica gel chromatography using a mixture of ethyl acetate in hexane (0-50%) to afford tert-butyl 1-(4-(5-(3-phenyl-4-(trifluoromethyl) isoxazol-5-yl)-1,2,4-oxadiazol-3-yl)benzyl)azetidine-3-carboxylate (4.60 g; 78%) as a white, crystalline solid. The material was suspended in methanol (~75 mL) and was sonicated for 5 minutes. The MeOH was removed under reduce pressure, and the residue was re-suspended in methanol (~50 mL) with sonication. Vacuum filtration and drying afforded tert-butyl 1-(4-(5-(3-phenyl-4-(trifluoromethyl)isoxazol-5-yl)-1,2,4-oxadiazol-3-yl)benzyl)azetidine-3-carboxylate (4.04 g, 7.67 mmol, 68% yield) as a white, crystalline solid. The methanol filtrate was concentrated to afford additional tert-butyl 1-(4-(5-(3-phenyl-4-(trifluoromethyl)isoxazol-5-yl)-1,2,4-oxadiazol-3-yl)benzyl)azetidine-3-carboxylate (570 mg; 10%) as a slightly off-white solid. The compound had an HPLC retention time=3.12 min.–Column. CHROMOLITH® SpeedROD 4.6×50 mm (4 min.); Solvent A=10% MeOH, 90% $H_2O$, 0.1% TFA; Solvent B=90% MeOH, 10% $H_2O$, 0.1% TFA. LC/MS $M^{+1}$=527.1. $^1H$ NMR (500 MHz, $CDCl_3$) δ ppm 1.47 (s, 9H) 3.28-3.37 (m, 3H), 3.60 (br. s., 2H), 3.74 (br. s., 2H), 7.49 (d, J=7.70 Hz, 2H), 7.53-7.62 (m, 3H), 7.69 (d, J=7.15 Hz, 2H), and 8.16 (d, J=7.70 Hz, 2H).

1. Preparation of 1-(4-(5-(3-phenyl-4-(trifluoromethyl)isoxazol-5-yl)-1,2,4-oxadiazol-3-yl)benzyl)azetidine-3-carboxylic acid A mixture of tert-butyl 1-(4-(5-(3-phenyl-4-(trifluoromethyl)isoxazol-5-yl)-1,2,4-oxadiazol-3-yl)benzyl)azetidine-3-carboxylate (6.12 g, 11.6 mmol) and trifluoroacetic acid (50.1 mL, 651 mmol) was stirred at room temperature for 1.5 h. By HPLC, the deprotection appeared to be complete after 1 h. The TFA was removed under reduced pressure, and the oily residue was diluted with water (100 mL) and sonicated for 5 min. The resulting suspension was stirred for an additional 10 min until a consistent white suspension was observed. A 1N aqueous solution of sodium hydroxide was added portion-wise until the pH was ~4.5 (42 mL of 1N NaOH). Over time, the pH drifted back down to 3-4, and additional 1N aqueous sodium hydroxide had to be added. The suspension was stirred overnight at room temperature. Several drops of 1N aqueous sodium hydroxide were added to re-adjust the pH to 4.5, and after 60 min., the pH appeared to be stable. The solid was collected by vacuum filtration, washed with water several times, and dried under reduced pressure for 5 h. The solid was then suspended in methanol (110 mL) in a 150 mL round bottom flask and sonicated for 15 min. During the sonication, the solution became very thick. An additional 25 mL of methanol was added, and the suspension was stirred overnight.

The product was collected by vacuum filtration, washed with methanol (~50 mL), and dried under reduced pressure. The solid was transferred to a 250 mL round bottom flask, re-suspended in methanol (115 mL), sonicated for 5 min., and stirred for 60 min. The solid was collected by vacuum filtration, washed with methanol (~50 mL), and dried over well under reduced pressure to give 1-(4-(5-(3-phenyl-4-(trifluoromethyl)isoxazol-5-yl)-1,2,4-oxadiazol-3-yl)benzyl)azetidine-3-carboxylic acid (5.06 g, 10.7 mmol, 92% yield) as a crystalline, white solid. The product had an HPLC ret. time=2.79 min.–Column: CHROMOLITH® SpeedROD 4.6×50 mm (4 min.); Solvent A=10% MeOH, 90% $H_2O$, 0.1% TFA; Solvent B=90% MeOH, 10% $H_2O$, 0.1% TFA. LC/MS $M^{+1}$=471.3. $^1HNMR$ (500 MHz, DMSO-$d_6$) δ ppm 3.20-3.46 (m, 5H), 3.66 (s, 2H), 7.53 (d, J=8.25 Hz, 2H), 7.60-7.70 (m, 5H), and 8.06 (d, J=7.70 Hz, 2H).

HPLC purity 100/99.8%, ret. time=7.62 min. (A linear gradient using 5% acetonitrile, 95% water, and 0.05% TFA (Solvent A) and 95% acetonitrile, 5% water, and 0.05% TFA (Solvent B); t=0 min., 10% B, t=12 min., 100% B (15 min.) was employed on a SunFire C18 3.5 u 4.6×150 mm column. Flow rate was 2 ml/min and UV detection was set to 220/254 nm.).

HPLC purity 100/99.9%, ret. time=8.45 min. (A linear gradient using 5% acetonitrile, 95% water, and 0.05% TFA (Solvent A) and 95% acetonitrile, 5% water, and 0.05% TFA (Solvent B); t=0 min., 10% B, t=12 min., 100% B (15 min.) was employed on a XBridge Ph 3.5 u 4.6×150 mm column. Flow rate was 2 ml/min and UV detection was set to 220/254 nm.).

Example 2

1-(4-(5-(5-Phenyl-4-(trifluoromethyl)isoxazol-3-yl)-1,2,4-oxadiazol-3-yl)benzyl)azetidine-3-carboxylic acid (2)

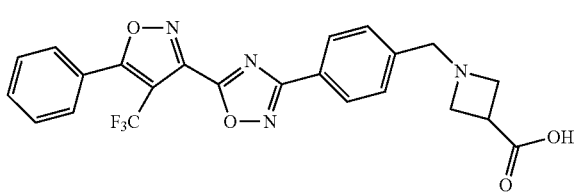

2-A. Ethyl 5-phenylisoxazole-3-carboxylate (2-A)

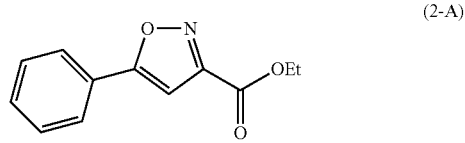 [SMILES: CCOC(=O)c1cc(-c2ccccc2)on1]

To a mixture of (Z)-ethyl 2-chloro-2-(hydroxyimino)acetate (3.03 g, 20 mmol) and ethynylbenzene (4.39 mL, 40 mmol) in ether (80 mL) at room temperature was added a solution of triethylamine (5.58 mL, 40.0 mmol) in ether (20 mL) dropwise over 60 minutes. The reaction mixture was stirred for 2 h at room temperature. The reaction mixture was filtered, and the filtrate was concentrated to a yellow oil which was purified by flash silica gel chromatography using a mixture of ethyl acetate in hexane (0-12%) to afford ethyl 5-phenylisoxazole-3-carboxylate (3.06 g, 14.09 mmol, 70% yield) as a white solid. The compound had an HPLC retention time=2.99 minutes (YMC-Combi 4.6×50 mm S-5 ODS column) eluting with 10-90% aqueous methanol+0.2% phosphoric acid over a 4 minute gradient. MS: (M+H)=218.12. $^1$H NMR (400 MHz, CDCl$_3$) δ ppm 1.45 (t, J=7.3 Hz, 3H), 4.48 (q, J=7.3, 2H), 6.93 (s, 1H), 7.45-7.53 (m, 3H), and 7.77-7.85 (m, 2H).

2-B. Ethyl 4-iodo-5-phenylisoxazole-3-carboxylate

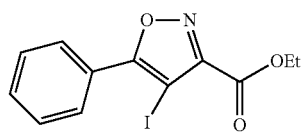

(2-B)

A mixture of ethyl 5-phenylisoxazole-3-carboxylate (406 mg, 1.87 mmol) and N-iodosuccinimide (505 mg, 2.24 mmol) in trifluoroacetic acid (10 mL) was stirred at room temperature for 1.5 h. The volatiles were removed under reduced pressure, and the residue was partitioned between ethyl acetate (50 mL) and water (50 mL). The organic layer was washed with a 1N aqueous solution of sodium hydroxide (50 mL), washed with a 2.5% aqueous solution of sodium bisulfite (50 mL), washed with brine (50 mL), and dried over anhydrous magnesium sulfate. Concentration under reduced pressure afforded ethyl 4-iodo-5-phenylisoxazole-3-carboxylate (641 mg, 1.87 mmol, 100% yield) as a light yellow oil. The compound had an HPLC retention time=3.36 minutes (YMC-Combi 4.6×50 mm S-5 ODS column) eluting with 10-90% aqueous methanol+0.2% phosphoric acid over a 4 minute gradient. MS: (M+H)=343.97. $^1$H NMR (400 MHz, CDCl$_3$) δ ppm 1.47 (t, J=7.1 Hz, 3H), 4.50 (q, J=7.0 Hz, 2H), 7.52-7.56 (m, 3H), and 8.05 (m, 2H).

Large Scale: A mixture of ethyl 5-phenylisoxazole-3-carboxylate (3.05 g, 14.0 mmol) and N-iodosuccinimide (3.79 g, 16.9 mmol) in trifluoroacetic acid (78 mL) was stirred at room temperature for 3.5 h. The volatiles were removed under reduced pressure, and the residue was partitioned between ethyl acetate (150 mL) and water (150 mL). The organic layer was washed with a 1N aqueous solution of sodium hydroxide (150 mL), washed with a 3% aqueous solution of sodium bisulfite (2×150 mL), washed with brine (150 mL), and dried over anhydrous magnesium sulfate. Concentration under reduced pressure afforded ethyl 4-iodo-5-phenylisoxazole-3-carboxylate (4.69 g, 13.7 mmol, 97% yield) as a light yellow oil.

2-C. Ethyl 5-phenyl-4-(trifluoromethyl)isoxazole-3-carboxylate

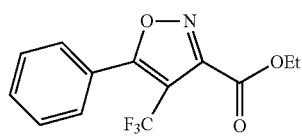

(2-C)

To a solution of ethyl 4-iodo-5-phenylisoxazole-3-carboxylate (638 mg, 1.86 mmol) and copper(I) iodide (70.8 mg, 0.372 mmol) in N,N-dimethylformamide (9 mL) and HMPA (1.2 mL) at room temperature was added methyl 2,2-difluoro-2-(fluorosulfonyl)acetate (0.947 mL, 7.44 mmol) in one portion. The reaction mixture was immediately immersed in an oil bath at 75-80° C. and was stirred for 6 hrs. The reaction mixture was then allowed to cool to room temperature and was stirred overnight. The reaction mixture was partitioned between ethyl ether (125 mL) and a saturated aqueous solution of ammonium chloride (125 mL). The organic layer was washed with a saturated aqueous solution of ammonium chloride (125 mL), washed with water (2×125 mL), washed with brine (50 mL), and dried over anhydrous magnesium sulfate. Concentration under reduced pressure followed by purification by silica gel chromatography using a mixture of ethyl acetate in hexane (0-10%) afforded ethyl 5-phenyl-4-(trifluoromethyl)isoxazole-3-carboxylate (454 mg, 1.59 mmol, 86% yield) as a colorless oil. The compound had an HPLC retention time=3.44 minutes (YMC-Combi 4.6×50 mm S-5 ODS column) eluting with 10-90% aqueous methanol+0.2% phosphoric acid over a 4 minute gradient. MS: (M+H)=286.01. $^1$H NMR (400 MHz, CDCl$_3$) δ ppm 1.45 (t, J=7.2 Hz, 3H), 4.51 (q, J=7.3 Hz, 2H), 7.52-7.62 (m, 3H), and 7.69 (d, J=7.5 Hz, 2H).

Large Scale: To a solution of ethyl 4-iodo-5-phenylisoxazole-3-carboxylate (4.62 g, 13.5 mmol) and copper(I) iodide (0.513 g, 2.69 mmol) in N,N-dimethylformamide (59.8 mL) and HMPA (7.48 mL) at room temperature was added methyl 2,2-difluoro-2-(fluorosulfonyl)acetate (6.86 mL, 53.9 mmol) at once. The reaction mixture was immediately immersed in an oil bath at 75-80° C. Stirring was continued at this temperature for 3.5 h. After cooling to room temperature, the reaction mixture was cooled in an ice bath. A saturated aqueous solution of ammonium chloride (~50 mL) was added slowly to quench the reaction. The mixture was partitioned between ethyl ether (400 mL) and a saturated aqueous solution of ammonium chloride (400 mL). The organic layer was washed with a saturated aqueous solution of ammonium chloride (200 mL), washed with water (2×200 mL), washed with brine (50 mL), and dried over anhydrous magnesium sulfate. Concentration under reduced pressure followed by purification by silica gel chromatography using a mixture of ethyl acetate in hexane (0-10%) afforded ethyl 5-phenyl-4-(trifluoromethyl)isoxazole-3-carboxylate (3.6 g, 12.6 mmol, 94% yield) as a colorless oil.

2-D. 5-Phenyl-4-(trifluoromethyl)isoxazole-3-carboxylic acid

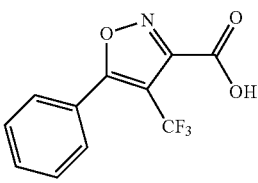

(2-D)

To a solution of ethyl 5-phenyl-4-(trifluoromethyl)isoxazole-3-carboxylate (3.6 g, 12.6 mmol) in methanol (100 mL) and water (20 mL) at room temperature was added lithium hydroxide, monohydrate (0.583 g, 13.9 mmol). The reaction mixture was stirred at room temperature for 30 minutes. The methanol was removed under reduce pressure, and the residue was diluted with water (~100 mL). Ethyl ether (200 mL) was added, and the pH of the aqueous layer was adjusted to <1 with a 1N aqueous solution of hydrochloric acid. The mixture was transferred to a separatory funnel, and after agitation, the layers were separated. The organic layer was washed with brine (100 mL), dried over anhydrous magnesium sulfate, and concentrated to afford 5-phenyl-4-(trifluoromethyl)isoxazole-3-carboxylic acid (3.12 g, 12.13 mmol, 96% yield) as a white, crystalline solid. The compound had an HPLC retention time=2.58 minutes (YMC-Combi 4.6×50 mm S-5 ODS column) eluting with 10-90% aqueous methanol+0.2% phosphoric acid over a 4 minute gradient. MS: (M+Na)=279.95. $^1$H NMR (400 MHz, CDCl$_3$) δ ppm 7.53-7.64 (m, 3H), and 7.70 (d, J=7.5 Hz, 2H).

2-E. 5-Phenyl-4-(trifluoromethyl)isoxazole-3-carbonyl fluoride

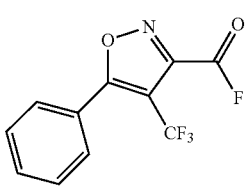

(2-E)

To a mixture of 5-phenyl-4-(trifluoromethyl)isoxazole-3-carboxylic acid (197 mg, 0.766 mmol) and pyridine (0.074 mL, 0.919 mmol) in dichloromethane (5 mL) at room temperature was added cyanuric fluoride (0.078 mL, 0.919 mmol). The reaction mixture was stirred at room temperature for 18 h. The mixture was diluted with dichloromethane (40 mL) and washed with an ice-cold 0.5N aqueous solution of hydrochloric acid (20 mL). The aqueous layer was extracted with dichloromethane (20 mL), and the combined organic layers were washed with ice-cold water (20 mL) and dried over anhydrous magnesium sulfate. Concentration under reduced pressure afforded 5-phenyl-4-(trifluoromethyl)isoxazole-3-carbonyl fluoride (199 mg, 0.768 mmol, 100% yield) as a pale yellow oil. The compound had an HPLC retention time=2.53 min. (methyl ester)—Column: CHROMOLITH® SpeedROD 4.6×50 mm (4 min.); Solvent A=10% MeOH, 90% H$_2$O, 0.1% TFA; Solvent B=90% MeOH, 10% H$_2$O, 0.1% TFA.

2-F. tert-Butyl 1-(4-(5-(5-phenyl-4-(trifluoromethyl) isoxazol-3-yl)-1,2,4-oxadiazol-3-yl)-benzyl)-azetidine-3-carboxylate

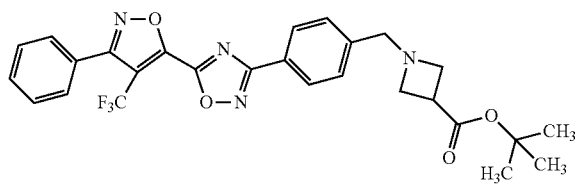

(2-F)

To a mixture of 5-phenyl-4-(trifluoromethyl)isoxazole-3-carbonyl fluoride (100 mg, 0.386 mmol) and (Z)-tert-butyl 1-(4-(N'-hydroxycarbamimidoyl)benzyl)azetidine-3-carboxylate (Int.1, 118 mg, 0.386 mmol) in acetonitrile (2 mL) at room temperature was added Hunig's Base (0.081 mL, 0.463 mmol). The reaction mixture was stirred at room temperature for 3 days. The volatiles were removed under reduced pressure, and the residue was partitioned between dichloromethane (30 mL) and a saturated aqueous solution of sodium bicarbonate (30 mL). The aqueous layer was extracted with dichloromethane (2×20 mL), and the combined organic layers were dried over anhydrous magnesium sulfate and concentrated to afford a light yellow oil. The compound was purified by flash silica gel chromatography using a mixture of ethyl acetate/hexane (0-70%) to give tert-butyl 1-(4-(5-(5-phenyl-4-(trifluoromethyl)isoxazol-3-yl)-1,2,4-oxadiazol-3-yl)benzyl)azetidine-3-carboxylate (175 mg, 0.332 mmol, 86% yield) as a white, crystalline solid. The compound had an HPLC retention time=3.34 minutes (YMC-Combi 4.6×50 mm S-5 ODS column) eluting with 10-90% aqueous methanol+0.2% phosphoric acid over a 4 minute gradient. MS: (M+H)=527.13. $^1$H NMR (400 MHz, CDCl$_3$) δ ppm 1.47 (s, 9H), 3.26-3.33 (m, 3H), 3.54-3.59 (m, 2H), 3.70 (s, 2H), 7.46 (d, J=8.28 Hz, 2H), 7.56-7.62 (m, 2H), 7.63-7.68 (m, 1H), 7.78 (d, J=7.28 Hz, 2H), and 8.16 (d, 2H).

2. Preparation of 1-(4-(5-(5-Phenyl-4-(trifluoromethyl)isoxazol-3-yl)-1,2,4-oxadiazol-3-yl)benzyl) azetidine-3-carboxylic acid A solution of tert-butyl 1-(4-(5-(5-phenyl-4-(trifluoromethyl)isoxazol-3-yl)-1,2,4-oxadiazol-3-yl)benzyl)azetidine-3-carboxylate (293 mg, 0.556 mmol) in trifluoroacetic acid (4 mL) was allowed to stand at room temperature for 1.5 h. The volatiles were removed under reduced pressure, and the residue was suspended in water (5 ml). The pH was adjusted to –4 with a 1N aqueous solution of sodium hydroxide with stirring. The resulting thick suspension was stirred at room temperature for 1 hr. The precipitate was collected by vacuum filtration and dried well under reduced pressure. The compound was suspended in methanol and stirred at room temperature for 18 hr. The product was collected by vacuum filtration, washed with methanol, and dried well under reduced pressure to afford 1-(4-(5-(5-phenyl-4-(trifluoromethyl)isoxazol-3-yl)-1,2,4-oxadiazol-3-yl)benzyl)azetidine-3-carboxylic acid (194 mg, 0.412 mmol, 74.1% yield) as a white, crystalline solid.

The compound had an HPLC retention time=3.09 minutes (YMC-Combi 4.6×50 mm S-5 ODS column) eluting with 10-90% aqueous methanol+0.2% phosphoric acid over a 4 minute gradient. MS: (M+H)=470.99. $^1$H NMR (500 MHz, DMSO-d$_6$) δ ppm 3.22-3.39 (m, 4H), 3.43 (br. s., 2H) 3.66 (br. s., 2H), 7.53 (d, J=7.70 Hz, 2H), 7.69 (d, J=7.15 Hz, 2H), 7.74 (d, J=7.15 Hz, 1H), 7.82 (d, J=7.15 Hz, 2H), 8.05 (d, J=8.25 Hz, 2H) and $^1$H NMR (400 MHz, MeOD) δ ppm 3.45 (m, 1H), 4.19-4.22 (m, 4H), 4.43 (s, 2H), 7.64-7.75 (m, 5H), 7.83 (d, J=7.5 Hz, 2H), and 8.28 (d, J=8.3 Hz, 2H).

HPLC purity 99.7/99.6%, ret. time=8.95 min. (A linear gradient using 5% acetonitrile, 95% water, and 0.05% TFA (Solvent A) and 95% acetonitrile, 5% water, and 0.05% TFA (Solvent B); t=0 min., 10% B, t=15 min., 100% B (18 min.) was employed on a SunFire C-18 3.5 micron, 4.6×150 mm Column. Flow rate was 2 ml/min and UV detection was set to 220/254 nm.).

HPLC purity 99.8/99.6%, ret. time=9.78 min. (A linear gradient using 5% acetonitrile, 95% water, and 0.05% TFA (Solvent A) and 95% acetonitrile, 5% water, and 0.05% TFA (Solvent B); t=0 min., 10% B, t=15 min., 100% B (18 min.) was employed on a XBridge Ph 3.5 u 4.6×150 mm column. Flow rate was 2 ml/min and UV detection was set to 220/254 nm.).

Example 3

1-(4-(5-(4-Butyl-5-phenylisoxazol-3-yl)-1,2,4-oxa-diazol-3-yl)benzyl)-azetidine-3-carboxylic acid (3)

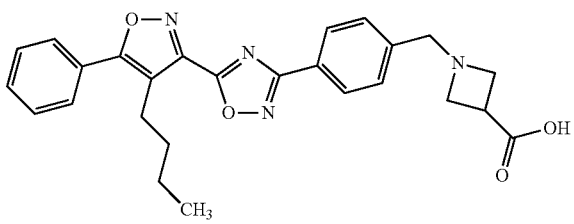

3-A. Methyl 4-butyl-5-phenylisoxazole-3-carboxylate (3-A)

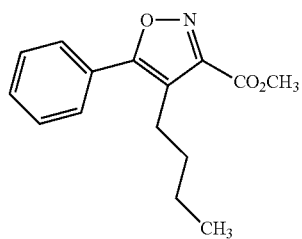

A solution of hex-1-ynylbenzene (0.274 mL, 1.56 mmol), dimethyl 2-nitromalonate (0.421 mL, 3.12 mmol), 1-butyl-3-methylimidazoliumhexafluorophosphate (0.032 mL, 0.156 mmol) in toluene (6 mL) was subjected to the microwave at 170° C. for 150 min. The reaction mixture was concentrated under reduced pressure, and the residue was purified by flash silica gel chromatography using 5% ethyl acetate in hexane to give methyl 4-butyl-5-phenylisoxazole-3-carboxylate (0.142 g, 0.531 mmol, 34.1% yield) as a clear, colorless oil. The product was 97% pure by HPLC with a ret. time=3.11 min.–Column. CHROMOLITH® SpeedROD 4.6×50 mm (4 min.); Solvent A=10% MeOH, 90% $H_2O$, 0.1% TFA; Solvent B=90% MeOH, 10% $H_2O$, 0.1% TFA. LC/MS $M^{+1}$=260.2.

3-B. 4-Butyl-5-phenylisoxazole-3-carboxylic acid (3-B)

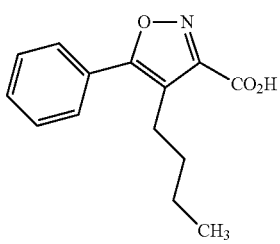

A mixture of methyl 4-butyl-5-phenylisoxazole-3-carboxylate (0.142 g, 0.548 mmol) and lithium hydroxide hydrate (0.023 g, 0.548 mmol) in methanol (3.0 mL) and water (1.5 mL) was stirred at room temperature overnight. The reaction mixture was concentrated to dryness to give 4-butyl-5-phenylisoxazole-3-carboxylic acid, lithium salt (0.134 g, 0.531 mmol, 97% yield) as a white solid. The compound had an HPLC ret. time=2.82 min.–Column. CHROMOLITH® SpeedROD 4.6×50 mm (4 min.); Solvent A=10% MeOH, 90% $H_2O$, 0.1% TFA; Solvent B=90% MeOH, 10% $H_2O$, 0.1% TFA. LC/MS $M^{+1}$=246.15. $^1$H NMR (500 MHz, DMSO-$d_6$) δ ppm 0.84 (t, J=7.42 Hz, 3H), 1.23-1.32 (m, 2H), 1.44-1.53 (m, 2H), 2.66-2.72 (m, 2H), 7.44-7.49 (m, 1H), 7.53 (t, J=7.42 Hz, 2H), and 7.64 (d, J=7.15 Hz, 2H).

3. 1-(4-(5-(4-Butyl-5-phenylisoxazol-3-yl)-1,2,4-oxadiazol-3-yl)benzyl)azetidine-3-carboxylic acid A mixture of 4-butyl-5-phenylisoxazole-3-carboxylic acid, lithium salt (0.132 g, 0.523 mmol), (Z)-tert-butyl 1-(4-(N'-hydroxycarbamimidoyl)benzyl)azetidine-3-carboxylate (Int.1, 0.160 g, 0.523 mmol), N1-((ethylimino)methylene)-N3,N3-dimethylpropane-1,3-diamine hydrochloride (0.100 g, 0.523 mmol), and HOBt (0.080 g, 0.523 mmol) in N,N-dimethylformamide (4 mL) was stirred at room temperature for 60 min and then heated at 60° C. overnight. The solvent was removed under reduced pressure. The residue was purified by flash silica gel chromatography eluting with 1% methanol in dichloromethane to give tert-butyl 1-(4-(5-(4-butyl-5-phenylisoxazol-3-yl)-1,2,4-oxadiazol-3-yl)benzyl) azetidine-3-carboxylate (0.156 g) as a pale yellow solid. The ester intermediate was >99% pure by HPLC with a ret. time=3.40 min.–Column. CHROMOLITH® SpeedROD 4.6×50 mm (4 min.); Solvent A=10% MeOH, 90% $H_2O$, 0.1% TFA; Solvent B=90% MeOH, 10% $H_2O$, 0.1% TFA. LC/MS $M^{+1}$=515.0.

The tert-butyl 1-(4-(5-(4-butyl-5-phenylisoxazol-3-yl)-1,2,4-oxadiazol-3-yl)benzyl)-azetidine-3-carboxylate intermediate (0.156 g) was stirred in trifluoroacetic acid (4.03 mL, 52.3 mmol) for 30 min. and concentrated under reduced pressure to give the desired product as a yellow, viscous oil. The oil was dissolved in dichloromethane and washed with a saturated aqueous solution of sodium bicarbonate. The organic layer, which contained the product (presumably as the sodium salt) was concentrated under reduced pressure. The white, solid residue was dissolved in water (pH ~9), and the pH was adjusted to ~4.5 with concentrated hydrochloric acid. The resulting white precipitate was collected by vacuum filtration and dried (no additional product in aqueous layer by HPLC). The solid was diluted with methanol and sonicated for 5 min. The methanol was removed under reduced pressure. The resulting solid was once again diluted with methanol, sonicated, collected by vacuum filtration, and washed with methanol. The resulting solid was dried well to give 1-(4-(5-(4-butyl-5-phenylisoxazol-3-yl)-1,2,4-oxadiazol-3-yl)benzyl)azetidine-3-carboxylic acid (0.102 g, 0.222 mmol, 42.5% yield) as a white, crystalline solid (There was some product remaining in the methanol filtrate). The compound had an HPLC with a ret. time=3.11 min.–Column. CHROMOLITH® SpeedROD 4.6×50 mm (4 min.); Solvent A=10% MeOH, 90% $H_2O$, 0.1% TFA; Solvent B=90% MeOH, 10% $H_2O$, 0.1% TFA. LC/MS $M^{+1}$=459.1. $^1$H NMR (500 MHz, DMSO-$d_6$) δ ppm 0.91 (t, J=7.42 Hz, 3H), 1.37-1.46 (m, 2H), 1.62-1.70 (m, 2H), 3.00-3.06 (m, 2H), 3.23 (br. s., 3H), 3.43 (br. s., 2H), 3.65 (s, 2H), 7.52 (d, J=8.25 Hz, 2H), 7.59-7.68 (m, 3H), 7.83 (d, J=7.15 Hz, 2H), 8.06 (d, J=8.25 Hz, 2H), and 12.27 (s, 1H).

Example 4

1-(4-(5-(4-Isobutyl-5-phenylisoxazol-3-yl)-1,2,4-oxadiazol-3-yl)benzyl)-azetidine-3-carboxylic acid (4)

4-A. Methyl 4-isobutyl-5-phenylisoxazole-3-carboxylate (4-A)

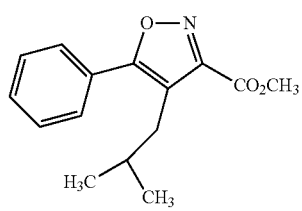

A solution of (4-methylpent-1-ynyl)benzene (0.247 g, 1.56 mmol), dimethyl 2-nitromalonate (0.421 mL, 3.12 mmol), 1-butyl-3-methylimidazoliumhexafluorophosphate (0.032 mL, 0.156 mmol) in toluene (5 mL) was subjected to the microwave at 170° C. for 150 min. By HPLC, the reaction was ~40-50% complete and resubjected to the microwave conditions for 360 min. (170° C.). The toluene was decanted off leaving a dark gum which was triturated several times with ethyl acetate. The combined organic layers were concentrated under reduced pressure. The residue was purified by flash silica gel chromatography using 5% ethyl acetate in hexane to give methyl 4-isobutyl-5-phenylisoxazole-3-carboxylate (0.122 g, 0.470 mmol, 30.2% yield) as a clear, colorless oil. The compound had an HPLC ret. time=2.96 min.–Column: CHROMOLITH® SpeedROD 4.6×50 mm (4 min.); Solvent A=10% MeOH, 90% $H_2O$, 0.1% TFA; Solvent B=90% MeOH, 10% $H_2O$, 0.1% TFA. LC/MS $M^{+1}$=259.9. $^1H$ NMR (500 MHz, chloroform-d) δ ppm 0.88 (s, 3H), 0.89 (s, 3H), 1.89 (dt, J=13.75, 6.87 Hz, 1H), 2.80 (d, J=7.15 Hz, 2H), 4.00 (s, 3H), 7.45-7.53 (m, 3H), 7.73 (d, J=6.60 Hz, 2H).

4-B. 4-Isobutyl-5-phenylisoxazole-3-carboxylic acid (4-B)

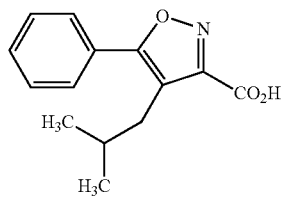

A mixture of methyl 4-isobutyl-5-phenylisoxazole-3-carboxylate (0.122 g, 0.470 mmol) and lithium hydroxide hydrate (0.020 g, 0.470 mmol) in methanol (2.5 mL) and water (1.25 mL) was stirred at room temperature overnight. The reaction mixture was concentrated to dryness to give 4-isobutyl-5-phenylisoxazole-3-carboxylic acid, lithium salt (0.119 g, 0.472 mmol, 100% yield) as a white solid. The compound had an HPLC ret. time=2.68 min.–Column: CHROMOLITH® SpeedROD 4.6×50 mm (4 min.); Solvent A=10% MeOH, 90% $H_2O$, 0.1% TFA; Solvent B=90% MeOH, 10% $H_2O$, 0.1% TFA. LC/MS $M^{+1}$=245.8.

4. 1-(4-(5-(4-Isobutyl-5-phenylisoxazol-3-yl)-1,2,4-oxadiazol-3-yl)benzyl)azetidine-3-carboxylic acid A mixture of 4-isobutyl-5-phenylisoxazole-3-carboxylic acid, lithium salt (0.119 g, 0.472 mmol), (Z)-tert-butyl 1-(4-(N'-hydroxycarbamimidoyl)benzyl)azetidine-3-carboxylate (Int.1, 0.144 g, 0.472 mmol), N1-((ethylimino)methylene)-N3,N3-dimethylpropane-1,3-diamine hydrochloride (0.090 g, 0.472 mmol), and HOBt (0.072 g, 0.472 mmol) in N,N-dimethylformamide (3.6 mL) was stirred at room temperature for 15 min and then heated at 60° C. overnight. The reaction mixture was diluted with ethyl acetate, washed with a saturated aqueous solution of sodium bicarbonate (2×), washed with a 10% aqueous solution of lithium chloride (2×), and dried over anhydrous sodium sulfate. The product mixture was concentrated under reduced pressure. The residue was purified by flash silica gel chromatography using a 1% mixture of methanol in dichloromethane to give tert-butyl 1-(4-(5-(4-isobutyl-5-phenylisoxazol-3-yl)-1,2,4-oxadiazol-3-yl)benzyl)azetidine-3-carboxylate (0.179 g) as a pale yellow solid. The ester intermediate was 98% pure by HPLC with a ret. time=3.27 min.–Column: CHROMOLITH® SpeedROD 4.6×50 mm (4 min.); Solvent A=10% MeOH, 90% $H_2O$, 0.1% TFA; Solvent B=90% MeOH, 10% $H_2O$, 0.1% TFA. LC/MS $M^{+1}$=515.4.

The tert-butyl 1-(4-(5-(4-isobutyl-5-phenylisoxazol-3-yl)-1,2,4-oxadiazol-3-yl)benzyl)-azetidine-3-carboxylate intermediate was stirred in trifluoroacetic acid (3.64 mL, 47.2 mmol) for 30 min. and concentrated under reduced pressure to give the desired product as a pale yellow solid. The solid was dispersed in water with some methanol with sonication. The pH was adjusted to ~4, and the resulting solid was collected by vacuum filtration, washed with water (3×), and dried. The white solid was triturated with methanol with sonication and filtered to give 1-(4-(5-(4-isobutyl-5-phenylisoxazol-3-yl)-1,2,4-oxadiazol-3-yl)benzyl)azetidine-3-carboxylic acid (0.074 g, 0.161 mmol, 34.2% yield) as a white, crystalline solid. The compound had an HPLC ret. time=2.99 min.–Column. CHROMOLITH® SpeedROD 4.6×50 mm (4 min.); Solvent A=10% MeOH, 90% $H_2O$, 0.1% TFA; Solvent B=90% MeOH, 10% $H_2O$, 0.1% TFA. LC/MS $M^{+1}$=459.3. $^1H$ NMR (500 MHz, DMSO-$d_6$) δ ppm 0.87 (d, J=6.60 Hz, 6H), 1.93 (ddd, J=13.61, 6.74, 6.60 Hz, 1H), 2.99 (d, J=7.15 Hz, 2H), 3.24 (br. s., 3H), 3.43 (s, 2H), 3.66 (s, 2H), 7.53 (d, J=7.70 Hz, 2H), 7.58-7.67 (m, 3H), 7.87 (d, J=6.60 Hz, 2H), and 8.06 (d, 2H). The methanol filtrate was concentrated under reduce pressure to give additional 1-(4-(5-(4-isobutyl-5-phenylisoxazol-3-yl)-1,2,4-oxadiazol-3-yl)benzyl)azetidine-3-carboxylic acid (0.034 g, 0.066 mmol, 13.99% yield) as a pale yellow solid (HPLC purity=89%).

Example 5

1-(2-Bromo-4-(5-(4-ethyl-5-phenylisoxazol-3-yl)-1,2,4-oxadiazol-3-yl)benzyl)azetidine-3-carboxylic acid (5)

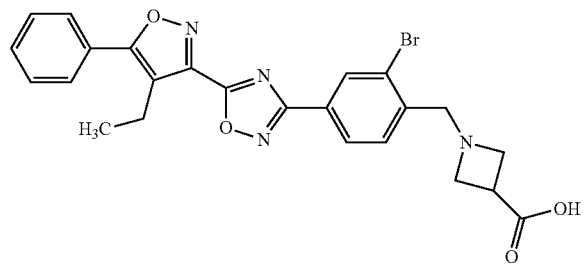

5-A. Methyl 4-ethyl-5-phenylisoxazole-3-carboxylate (5-A)

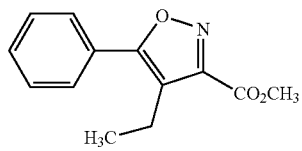

A solution of but-1-ynylbenzene (404 mg, 3.11 mmol) and dimethyl nitromalonate (0.381 mL, 2.82 mmol) in mesitylene (5 mL) was heated to 150° C. for 24 h. The reaction mixture was concentrated, and the residue purified on silica gel column with hexanes/ethyl acetate (10/1) to afford methyl 4-ethyl-5-phenylisoxazole-3-carboxylate (194 mg). The compound had an HPLC ret. time=3.25 min.–Column. YMC S5 COMBISCREEN® 4.6×50 mm; Gradient time: 4 min; Flow rate=4 ml/min; Solvent A=10% MeOH–90% Water–0.2% $H_3PO_4$; Solvent B=90% MeOH–10% water–0.2% $H_3PO$; Start % B=0; Final % B=100. LC-MS: $M^{+1}=232^+$.

5-B. 4-Ethyl-5-phenylisoxazole-3-carboxylic acid (5-B)

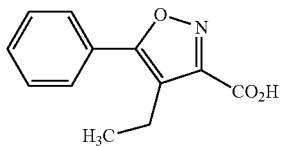

A solution of methyl 4-ethyl-5-phenylisoxazole-3-carboxylate (194 mg, 0.839 mmol) and 1N aqueous sodium hydroxide (1.26 mL, 1.258 mmol) in methanol (3 mL) was heated to 100° C. for 10 minutes under microwave. The reaction mixture was acidified with acetic acid until the pH was about 4. The mixture was concentrated, and the residue was suspended in water (2 mL) and stirred for 20 minutes. The solid was collected by vacuum filtration and dried to give 4-ethyl-5-phenylisoxazole-3-carboxylic acid (148 mg). The compound had an HPLC ret. time=2.93 min.–Column: YMC S5 COMBISCREEN® 4.6×50 mm; Gradient time: 4 min; Flow rate=4 ml/min; Solvent A=10% MeOH–90% Water–0.2% $H_3PO$; Solvent B=90% MeOH–10% water–0.2% $H_3PO_4$; Start % B=0; Final % B=100. LC-MS: $M^{+1}=218+$.

5-C. 3-Bromo-4-(bromomethyl)benzonitrile (5-C)

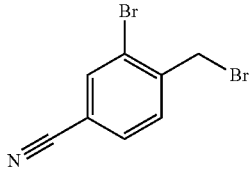

A solution of 3-bromo-4-methylbenzonitrile (1 g, 5.10 mmol) in chloroform (20 mL) was heated to 40-50° C. and N-bromosuccinimide (0.953 g, 5.36 mmol) was added in one portion followed by AIBN (8.38 mg, 0.051 mmol). After 1.5 hr. additional AIBN (20 mg) was added and the reaction was allowed to stir at 50° C. overnight. Additional AIBN (20 mg) and N-bromosuccinimide (1.1 g) were added, a reflux condenser was attached and the solution was heated to reflux. After several hours, additional AIBN (20 mg) was added and the reaction was allowed to stir at reflux overnight. The reaction was quenched by the addition of water and sat. aq. sodium bicarbonate. The organic phase was separated, concentrated in vacuo and purified by flash column chromatography (120 g silica, eluting with 0%-20% Ethyl Acetate in hexanes) to afford 3-bromo-4-(bromomethyl)benzonitrile as a pale yellow solid (800 mg, 2.88 mmol). $^1H$ NMR (500 MHz, MeOD) δ ppm 4.70 (s, 2H), 7.71 (d, J=8.0 Hz, 1H), 7.73 (d, J=8.0 Hz, 1H), 8.04 (s, 1H).

5-D. (Z)-tert-Butyl 1-(2-bromo-4-(N'-hydroxycarbamimidoyl)benzyl)azetidine-3-carboxylate (5-D)

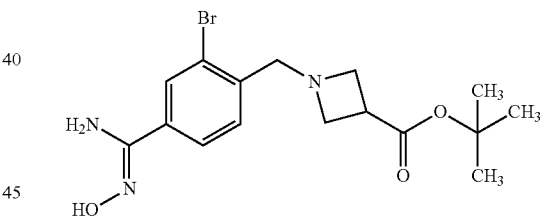

A reaction vial containing a stir bar was charged with 3-bromo-4-(bromomethyl)benzonitrile (100 mg, 0.364 mmol), tert-butyl azetidine-3-carboxylate acetic acid salt, Int.1-C (95 mg, 0.436 mmol), DMF (1 mL), and DIPEA (0.381 mL, 2.182 mmol). The vial was flushed with argon, sealed and placed on a reaction block which was heated to 65° C. After 5 hours, the reaction was cooled to RT and directly purified by preparative HPLC (methanol/water plus 0.1% TFA as eluent). To the product fractions was added a solution of sodium bicarbonate (200 mg) in water (4 mL) and then the volatiles were removed in vacuo to afford a white solid which was slurried in methanol (10 mL). Hydroxylamine hydrochloride (37.6 mg, 0.541 mmol) was added and the reaction was heated overnight in an oil bath set to 50° C. Additional hydroxylamine hydrochloride (30 mg) along with sodium bicarbonate (150 mg) were added and heating continued at 50° C. for 8 hours. The volatiles were removed in vacuo and the residue purified by preparative HPLC (methanol/water plus 0.1% TFA as eluent). The pH of the product containing fractions was adjusted to ~7 using sodium bicarbonate, the solvents were concentrated and the resulting aqueous solution was extracted with DCM. The organics were dried over anhydrous magnesium sulfate then concentrated to afford (Z)-tert-butyl 1-(2-bromo-4-(N'-hydroxycarbamimidoyl)benzyl)azetidine-3-carboxylate (12.6 mg, 0.032 mmol). The compound had an HPLC retention time=0.72 min.–Column: BEH C18 2.1×50 mm 1.7 u (gradient: 2% MeCN/water plus 0.05% to 98% MeCN/water plus 0.05% TFA over 1 min.); LC/MS M$^{+1}$=384/386.

5. 1-(2-Bromo-4-(5-(4-ethyl-5-phenylisoxazol-3-yl)-1,2,4-oxadiazol-3-yl)benzyl)azetidine-3-carboxylic acid A solution of 4-ethyl-5-phenylisoxazole-3-carboxylic acid, Int.5-D (7.83 mg, 0.036 mmol), EDCI (6.91 mg, 0.036 mmol), and HOBt (5.52 mg, 0.036 mmol) in DMF (2 mL) was stirred at RT for 5 minutes before being transferred to a flask containing (Z)-tert-butyl 1-(2-bromo-4-(N'-hydroxycarbamimidoyl)benzyl)azetidine-3-carboxylate, Int.5-B (12.60 mg, 0.033 mmol). The reaction was placed in an oil bath and heated overnight at 55° C. then the temperature was raised to 90° C. for 3 hours. The solution was cooled and the volatiles were removed under vacuum. The resulting residue was treated with TFA (2 mL) at RT for 3 hours. The TFA was evaporated and the residue was treated with triethylamine (3-4 mL) before again being evaporated to dryness. The residue was loaded onto a 4 g silica gel Isco cartridge (which had been pre-equilibrated with DCM) and purified by flash chromatography. Eluent: 0-20% MeOH in DCM (plus 5% NH$_4$OH). The product containing fractions were evaporated and placed under high vacuum to afford 1-(2-bromo-4-(5-(4-ethyl-5-phenylisoxazol-3-yl)-1,2,4-oxadiazol-3-yl)benzyl)azetidine-3-carboxylic acid as a pale yellow solid (13.1 mg, 0.024 mmol). The compound had an HPLC retention time=3.97 min.–Column: PHENOMENEX® Luna 3 u C18 4.6×30 mm (5 min. gradient; 4 mL/min); Solvent A=10% MeOH, 90% H$_2$O, 0.05% TFA; Solvent B=90% MeOH, 10% H$_2$O, 0.05% TFA. LC/MS M$^{+1}$=509/511. $^1$H NMR (500 MHz, MeOD) δ ppm 1.39 (t, J=7.5 Hz, 3H), 3.11 (q, J=7.5 Hz, 2H), 3.36-3.44 (m, 1H), 3.92 (dd, J=8.5 Hz, 8.5 Hz 2H), 4.01 (dd, J=8.8 Hz, 9.0 Hz 2H), 4.26 (s, 2H), 7.56-7.72 (m, 4H), 7.81-7.83 (m, 2H), 8.22 (dd, J=6.3, 1.8 Hz, 1H), 8.42 (d, 1.8 Hz).

Example 6

1-(4-(5-(4-Cyclopropyl-5-phenylisoxazol-3-yl)-1,2,4-oxadiazol-3-yl)benzyl)-azetidine-3-carboxylic acid, 2,2,2-trifluoroacetic acid salt

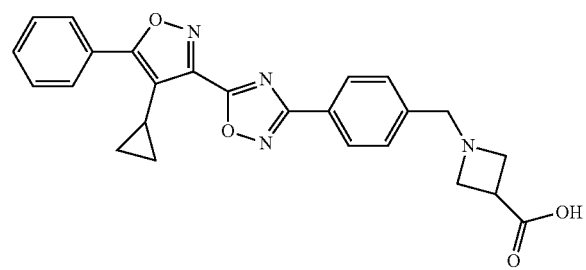

(6)

6-A. (Cyclopropylethynyl)benzene

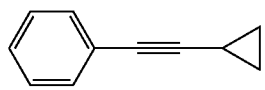

(6-A)

To a degassed solution of iodobenzene (0.549 mL, 4.90 mmol), dichlorobis(triphenylphosphine)-palladium(II) (0.206 g, 0.294 mmol), copper(I) iodide (0.047 g, 0.245 mmol) and diisopropylamine (3.49 mL, 24.5 mmol) in N,N-dimethylformamide (20 mL) was added cyclopropylacetylene (0.622 mL, 7.35 mmol). The reaction mixture was heated to 75° C. for 45 minutes. The reaction mixture was then diluted with ethyl acetate (150 mL), washed with a 10% aqueous solution of lithium chloride (2×100 mL), washed with a 2M aqueous solution of ammonium hydroxide (100 mL), washed with brine (100 mL), and dried over anhydrous sodium sulfate. Concentration afforded a crude product which was purified by silica gel chromatography with hexanes/dichloromethane (10/1) to give (cyclopropylethynyl)benzene (691 mg). The compound had an HPLC ret. time=3.40 min.–Column. YMC S5 COMBISCREEN® 4.6× 50 mm; Gradient time: 4 min; Flow rate=4 ml/min; Solvent A=10% MeOH–90% Water–0.2% H$_3$PO$_4$; Solvent B=90% MeOH–10% water–0.2% H$_3$PO$_4$; Start % B=0; Final % B=100.

6-B. Methyl 4-cyclopropyl-5-phenylisoxazole-3-carboxylate

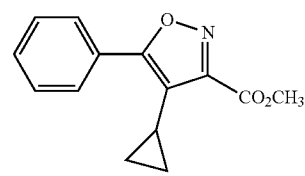

(6-B)

A solution of (cyclopropylethynyl)benzene (300 mg, 2.110 mmol) and dimethyl nitromalonate (0.854 mL, 6.33 mmol) in mesitylene (4 mL) was heated to 150° C. for 16 h. The reaction mixture was concentrated to yield a crude product which was purified by silica gel chromatography with hexanes/ethyl acetate (10/1) to yield methyl 4-cyclopropyl-5-phenylisoxazole-3-carboxylate. The compound was re-purified by preparative HPLC [Column: PHENOMENEX® S10 30×100 mm; Gradient time: 10 min; Flow rate=40 ml/min; Solvent A=10% MeOH–90% Water–0.1% TFA; Solvent B=90% MeOH–10% water–0.1% TFA; Start % B=20; Final % B=100] to yield methyl 4-cyclopropyl-5-phenylisoxazole-3-carboxylate (170 mg). The compound had an HPLC ret. time=2.77 min.–Column. YMC S5 COMBISCREEN® 4.6× 50 mm; Gradient time: 4 min; Flow rate=4 ml/min; Solvent A=10% MeOH–90% Water–0.2% H$_3$PO$_4$; Solvent B=90% MeOH–10% water–0.2% H$_3$PO$_4$; Start % B=0; Final % B=100. LC-MS: M$^{+1}$=244$^+$.

6-C. 4-Cyclopropyl-5-phenylisoxazole-3-carboxylic acid

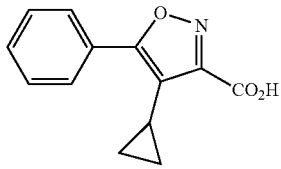

(6-C)

A solution of methyl 4-cyclopropyl-5-phenylisoxazole-3-carboxylate (170 mg, 0.699 mmol) and 1N aqueous sodium hydroxide (1 mL, 1.05 mmol) in methanol (6 mL) was heated to 80° C. in a sealed tube for 1 hr. The reaction mixture was acidified with acetic acid until the pH was ~4. The mixture was concentrated, and the residue was purified by preparative HPLC to give 4-cyclopropyl-5-phenylisoxazole-3-carboxylic acid (124 mg). The compound had an HPLC ret. time=2.81 min.–Column. YMC S5 COMBISCREEN® 4.6×50 mm; Gradient time: 4 min; Flow rate=4 ml/min; Solvent A=10% MeOH–90% Water–0.2% $H_3PO_4$; Solvent B=90% MeOH–10% water–0.2% $H_3PO_4$; Start % B=0; Final % B=100. LC-MS: $M^{+1}$=230$^+$.

6. 1-(4-(5-(4-Cyclopropyl-5-phenylisoxazol-3-yl)-1,2,4-oxadiazol-3-yl)benzyl)azetidine-3-carboxylic acid, 2,2,2-trifluoroacetic acid salt To a solution of 4-cyclopropyl-5-phenylisoxazole-3-carboxylic acid (22 mg, 0.096 mmol), HOBt (26.5 mg, 0.173 mmol), and diisopropylethylamine (0.067 mL, 0.384 mmol) in acetonitrile (1 mL) was added EDC (43.2 mg, 0.226 mmol) and (Z)-tert-butyl 1-(4-(N'-hydroxycarbamimidoyl)benzyl)azetidine-3-carboxylate (Int.1, 29.3 mg, 0.096 mmol). The reaction mixture was stirred at 80° C. for 2 h. The reaction mixture was concentrated, and the residue was purified by preparative HPLC to give tert-butyl 1-(4-(5-(4-cyclopropyl-5-phenylisoxazol-3-yl)-1,2,4-oxadiazol-3-yl)benzyl)azetidine-3-carboxylate.

A solution of tert-butyl 1-(4-(5-(4-cyclopropyl-5-phenylisoxazol-3-yl)-1,2,4-oxadiazol-3-yl)benzyl)azetidine-3-carboxylate in dichloromethane (0.5 mL) and trifluoroacetic acid (0.5 mL) was stirred at room temperature for 30 minutes. Concentration under reduced pressure afforded 1-(4-(5-(4-cyclopropyl-5-phenylisoxazol-3-yl)-1,2,4-oxadiazol-3-yl)benzyl)azetidine-carboxylic acid, 2,2,2-trifluoroacetic acid salt (26.2 mg). The compound had an HPLC ret. time=3.06 min. Column. YMC S5 COMBISCREEN® 4.6×50 mm; Gradient time: 4 min; Flow rate=4 ml/min; Solvent A=10% MeOH–90% Water–0.2% $H_3PO_4$; Solvent B=90% MeOH–10% water–0.2% $H_3PO_4$; Start % B=0; Final % B=100. LC-MS: $M^{+1}$=443$^+$. $^1$H NMR (400 MHz, MeOD) δ ppm 0.41-0.47 (m, 2H), 1.09-1.16 (m, 2H), 2.12 (tt, J=8.31, 5.36 Hz, 1H), 3.66-3.77 (m, 1H), 4.35-4.41 (m, 4H), 4.53 (s, 2H), 7.56-7.64 (m, 3H), 7.70 (d, J=8.53 Hz, 2H), 7.95-8.00 (m, 2H), and 8.32 (d, J=8.28 Hz, 2H).

Example 7

1-(4-(5-(4-tert-Butyl-5-phenylisoxazol-3-yl)-1,2,4-oxadiazol-3-yl)benzyl)-azetidine-3-carboxylic acid, 2-2-2-trifluoroacetic acid salt

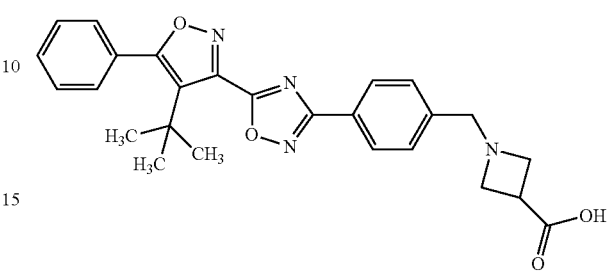

(7)

7-A. (3,3-Dimethylbut-1-ynyl)benzene

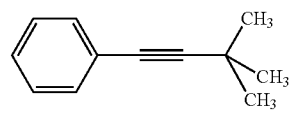

(7-A)

A degassed solution of iodobenzene (0.549 mL, 4.90 mmol), dichlorobis(triphenylphosphine)-palladium(II) (0.206 g, 0.294 mmol), copper(I) iodide (0.047 g, 0.245 mmol), and diisopropylamine (3.49 mL, 24.5 mmol) in N,N-dimethylformamide (20 mL) was added 3,3-dimethylbut-1-yne (0.896 mL, 7.35 mmol). The reaction mixture was and heated to 75° C. for 45 minutes. The reaction mixture was then diluted with ethyl acetate (150 mL), washed with 10% aqueous solution of lithium chloride (2×100 mL), washed with a 2M aqueous solution of ammonium hydroxide, washed with brine (100 mL), and dried over anhydrous sodium sulfate. Concentration followed by purification on silica gel chromatography with hexanes/dichloromethane (10/1) afforded (3,3-Dimethylbut-1-ynyl)benzene (740 mg). The compound had an HPLC ret. time=3.78 min.–Column: YMC S5 COMBISCREEN® 4.6×50 mm; Gradient time: 4 min; Flow rate=4 ml/min; Solvent A=10% MeOH–90% Water–0.2% $H_3PO_4$; Solvent B=90% MeOH–10% water–0.2% $H_3PO_4$; Start % B=0; Final % B=100.

7-B. Methyl 4-tert-butyl-5-phenylisoxazole-3-carboxylate

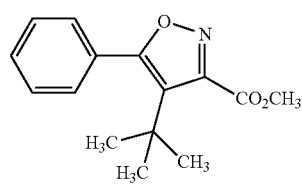

(7-B)

A solution of (3,3-Dimethylbut-1-ynyl)benzene (400 mg, 2.53 mmol) and dimethyl nitromalonate (0.853 mL, 6.32 mmol) in mesitylene (5 mL) was heated at 150° C. for 48 h. The reaction mixture was concentrated, and the residue was purified by silica gel chromatography with hexanes/ethyl acetate (10/1) to yield methyl 4-tert-butyl-5-phenylisoxazole-3-carboxylate (101 mg). The compound had an HPLC ret. time=3.39 min.–Column. YMC S5 COMBISCREEN® 4.6×50 mm; Gradient time: 4 min; Flow rate=4 ml/min; Solvent A=10% MeOH–90% Water–0.2% H$_3$PO$_4$; Solvent B=90% MeOH–10% water–0.2% H$_3$PO$_4$; Start % B=0; Final % B=100. LC-MS: M$^{+1}$=260$^+$.

7-C. 4-tert-Butyl-5-phenylisoxazole-3-carboxylic acid, sodium salt

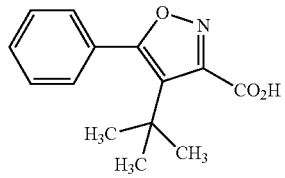

(7-C)

A solution of methyl 4-tert-butyl-5-phenylisoxazole-3-carboxylate (26 mg, 0.100 mmol) and 1N aqueous sodium hydroxide (150 µL, 0.150 mmol) in methanol (1 mL) was heated at 100° C. for 10 minutes via microwave. The reaction mixture was concentrated to yield 4-tert-butyl-5-phenylisoxazole-3-carboxylic acid, sodium salt (30 mg). The compound had an HPLC ret. time=2.97 min.–Column. YMC S5 COMBISCREEN® 4.6×50 mm; Gradient time: 4 min; Flow rate=4 ml/min; Solvent A=10% MeOH–90% Water–0.2% H$_3$PO$_4$; Solvent B=90% MeOH–10% water–0.2% H$_3$PO$_4$; Start % B=0; Final % B=100. LC-MS: M$^{+1}$=246$^+$.

7. 1-(4-(5-(4-tert-Butyl-5-phenylisoxazol-3-yl)-1,2,4-oxadiazol-3-yl)benzyl)azetidine-3-carboxylic acid, 2,2,2-trifluoroacetic acid salt A solution of 4-tert-butyl-5-phenylisoxazole-3-carboxylic acid (25 mg, 0.102 mmol), HOBt (28.1 mg, 0.183 mmol), and diisopropylethylamine (0.071 mL, 0.408 mmol) in acetonitrile (1 mL) was added EDC (45.9 mg, 0.240 mmol) and (Z)-tert-butyl 1-(4-(N'-hydroxycarbamimidoyl)benzyl)azetidine-3-carboxylate (Int.1, 31.1 mg, 0.102 mmol). The reaction mixture was stirred at 80° C. for 5 h. The reaction mixture was concentrated, and the residue was diluted with ethyl acetate (3 mL), washed with a saturated aqueous solution of sodium bicarbonate (1 mL), washed with water (1 mL), washed with brine (1 mL), and dried over anhydrous sodium sulfate. Concentration followed by purification by preparative HPLC afforded tert-butyl 1-(4-(5-(4-tert-butyl-5-phenylisoxazol-3-yl)-1,2,4-oxadiazol-3-yl)benzyl)-azetidine-3-carboxylate.

A solution of tert-butyl 1-(4-(5-(4-tert-butyl-5-phenylisoxazol-3-yl)-1,2,4-oxadiazol-3-yl)benzyl)azetidine-3-carboxylate in dichloromethane (0.5 mL) and trifluoroacetic acid (0.5 mL) was stirred at room temperature for 30 minutes. Concentration under reduced pressure afforded 1-(4-(5-(4-tert-butyl-5-phenylisoxazol-3-yl)-1,2,4-oxadiazol-3-yl)benzyl)azetidine-3-carboxylic acid, 2,2,2-trifluoroacetic acid salt (30.5 mg). The compound had an HPLC ret. time=3.12 min.–Column. YMC S5 COMBISCREEN® 4.6×50 mm; Gradient time: 4 min; Flow rate=4 ml/min; Solvent A=10% MeOH–90% Water–0.2% H$_3$PO$_4$; Solvent B=90% MeOH–10% water–0.2% H$_3$PO$_4$; Start % B=0; Final % B=100. LC-MS: M$^{+1}$=459$^+$. $^1$H NMR (500 MHz, MeOD) δ ppm 1.27 (s, 9H), 3.68-3.76 (m, 1H), 4.39 (d, J=7.70 Hz, 4H), 4.54 (s, 2H), 7.53-7.57 (m, 4H), 7.57-7.63 (m, 1H), 7.70 (d, J=8.25 Hz, 2H), and 8.29 (d, J=8.25 Hz, 2H).

Example 8

1-(4-(5-(5-Phenyl-4-(3,3,3-trifluoropropyl)isoxazol-3-yl)-1,2,4-oxadiazol-3-yl)benzyl)azetidine-3-carboxylic acid, 2,2,2-trifluoroacetic acid salt

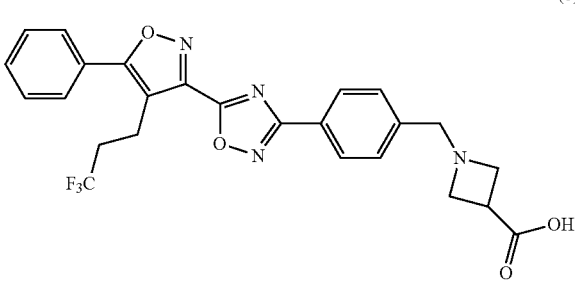

(8)

8-A. (5,5,5-Trifluoropent-1-ynyl)benzene

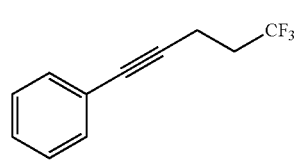

(8-A)

To a solution of 1,1,1-trifluoro-3-iodopropane (0.052 mL, 0.438 mmol), Pd$_2$(dba)$_3$ (24.0 mg, 0.026 mmol), Tri-2-furylphosphine (10.2 mg, 0.044 mmol) and copper(I) iodide (8.33 mg, 0.044 mmol) in N,N-dimethylformamide (2.5 mL) was added tributyl(phenylethynyl)stannane (0.178 mL, 0.481 mmol) under nitrogen. The reaction mixture was stirred at room temperature for 16 h. The reaction mixture was diluted with ethyl acetate (50 mL), washed with water (10 mL), washed with brine (10 mL), and dried over anhydrous sodium sulfate. Concentration followed by purification by silica gel chromatography with hexanes yielded (5,5,5-trifluoro-1-ynyl)benzene (50 mg). The compound had an HPLC ret. time=4.08 min.–Column: YMC S5 COMBISCREEN® 4.6×50 mm; Gradient time: 4 min; Flow rate=4 ml/min; Solvent A=10% MeOH–90% Water–0.2% H$_3$PO$_4$; Solvent B=90% MeOH–10% water–0.2% H$_3$PO$_4$; Start % B=0; Final % B=100.

8-B. Methyl 5-phenyl-4-(3,3,3-trifluoropropyl)isoxazole-3-carboxylate

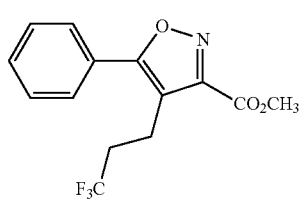

(8-B)

A solution of (5,5,5-trifluoropent-1-ynyl)benzene (215 mg, 1.09 mmol), diethyl nitromalonate (0.758 mL, 4.34 mmol), and 1-butyl-3-methylimidazolium hexafluorophosphate (0.023 mL, 0.108 mmol) in toluene (3 mL) was heated to 170° C. for 150 minutes. The reaction mixture was diluted with ethyl acetate (50 mL), washed with water (10 mL), washed with brine (10 mL), and dried over anhydrous sodium sulfate. Concentration followed by purification by silica gel chromatography with hexanes/ethyl acetate (9/1) provided methyl 5-phenyl-4-(3,3,3-trifluoropropyl)isoxazole-3-carboxylate (72 mg). The compound had an HPLC ret. time=3.61 min.–Column. YMC S5 COMBISCREEN® 4.6× 50 mm; Gradient time: 4 min; Flow rate=4 ml/min; Solvent A=10% MeOH–90% Water–0.2% H$_3$PO$_4$; Solvent B=90% MeOH–10% water–0.2% H$_3$PO$_4$; Start % B=0; Final % B=100.

8-C. 5-Phenyl-4-(3,3,3-trifluoropropyl)isoxazole-3-carboxylic acid

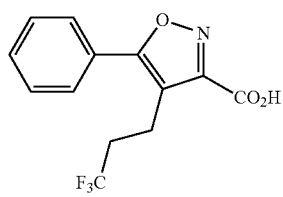

(8-C)

A solution of methyl 5-phenyl-4-(3,3,3-trifluoropropyl)isoxazole-3-carboxylate (25 mg, 0.084 mmol) and 1N aqueous sodium hydroxide (125 µL, 0.125 mmol) in methanol (1 mL) was heated at 23° C. for 2 h. To the reaction mixture was added acetic acid until the pH was ~5. The mixture was purified by preparative HPLC to afford 5-phenyl-4-(3,3,3-trifluoropropyl)isoxazole-3-carboxylic acid (5 mg). The compound had an HPLC ret. time=3.16 min.–Column. YMC S5 COMBISCREEN® 4.6×50 mm; Gradient time: 4 min; Flow rate=4 ml/min; Solvent A=10% MeOH–90% Water–0.2% H$_3$PO$_4$; Solvent B=90% MeOH–10% water–0.2% H$_3$PO$_4$; Start % B=0; Final % B=100. LC-MS: M$^{+1}$=286$^+$.

8. 1-(4-(5-(5-Phenyl-4-(3,3,3-trifluoropropyl)isoxazol-3-yl)-1,2,4-oxadiazol-3-yl)benzyl)-azetidine-3-carboxylic acid, 2,2,2-trifluoroacetic acid salt To a solution of 5-phenyl-4-(3,3,3-trifluoropropyl)isoxazole-3-carboxylic acid (5 mg, 0.018 mmol), HOBt (4.83 mg, 0.032 mmol) and diisopropylethylamine (12.3 µL, 0.070 mmol) in acetonitrile (0.5 mL) was added EDC (7.90 mg, 0.041 mmol) and (Z)-tert-butyl 1-(4-(N'-hydroxycarbamimidoyl)benzyl)azetidine-3-carboxylate (Int.1, 5.35 mg, 0.018 mmol). The reaction mixture was stirred at 23° C. for 2.5 h. The mixture was concentrated, and the residue was diluted with ethyl acetate (3 mL), washed with a saturated aqueous solution of sodium bicarbonate (1 mL), washed with water (1 mL), washed with brine (1 mL), and dried over anhydrous sodium sulfate. The mixture was concentrated and dissolved in acetonitrile (0.5 mL). A 1M solution of tetrabutylammonium fluoride in tetrahydrofuran (35 µL, 0.035 mmol) was added, and the reaction mixture was stirred for 1 h. The reaction mixture was concentrated, and the residue was diluted with ethyl acetate (3 mL), washed with water (1 mL), washed with a saturated aqueous solution of sodium carbonate (1 mL), washed with brine (1 mL), and dried over anhydrous sodium sulfate. Concentration followed by purification on a preparative TLC plate with hexanes/ethyl acetate (7/3) afforded tert-butyl 1-(4-(5-(5-phenyl-4-(3,3,3-trifluoropropyl)isoxazol-3-yl)-1,2,4-oxadiazol-3-yl)benzyl)azetidine-3-carboxylate.

A solution of tert-butyl 1-(4-(5-(5-phenyl-4-(3,3,3-trifluoropropyl)isoxazol-3-yl)-1,2,4-oxadiazol-3-yl)benzyl)azetidine-3-carboxylate in dichloromethane (0.5 mL) and trifluoroacetic acid (0.5 mL) was stirred at room temperature for 2 h. Concentration under reduced pressure afforded 1-(4-(5-(5-phenyl-4-(3,3,3-trifluoropropyl)isoxazol-3-yl)-1,2,4-oxadiazol-3-yl)benzyl)-azetidine-3-carboxylic acid, 2,2,2-trifluoroacetic acid salt (5.75 mg). The compound had an HPLC ret. time=3.23 min.–Column. YMC COMBISCREEN® ODS-A 4.6×50 mm S-5; Gradient time: 4 min; Flow rate=4 ml/min; Solvent A=10% MeOH–90% Water–0.1% TFA; Solvent B=90% MeOH–10% water–0.1% TFA. LC-MS: M$^{+1}$=499$^+$.

Example 9

1-(4-(5-(4-(1,1-Difluoroethyl)-5-phenylisoxazol-3-yl)-1,2,4-oxadiazol-3-yl)benzyl)azetidine-3-carboxylic acid, 2,2,2-trifluoroacetic acid salt

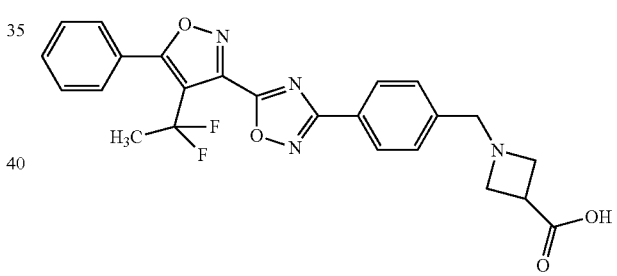

(9)

9-A. Methyl 5-phenylisoxazole-3-carboxylate

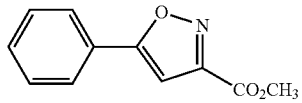

(9-A)

A solution of 5-phenylisoxazole-3-carboxylic acid (0.86 g, 4.55 mmol) in toluene (15.0 mL) and methanol (3 mL) was added a 2M solution of TMS-diazomethane in hexanes (3.1 mL, 6.14 mmol) dropwise at room temperature. The reaction mixture was stirred for 30 minutes and concentrated. The residue was dispersed in methanol (3 mL), stirred for 5 minutes, and filtered to give methyl 5-phenylisoxazole-3-carboxylate (897 mg). The compound had an HPLC ret. time=2.67 min.: YMC S5 COMBISCREEN® 4.6×50 mm; Gradient time: 4 min; Flow rate=4 ml/min; Solvent A=10%

MeOH–90% Water–0.2% H₃PO₄; Solvent B=90% MeOH–10% water–0.2% H₃PO₄; Start % B=0; Final % B=100. LC-MS: M$^{+1}$=204$^+$.

9-B. Methyl 4-bromo-5-phenylisoxazole-3-carboxylate

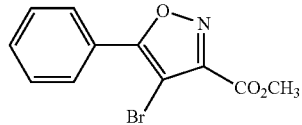

(9-B)

A solution of methyl 5-phenylisoxazole-3-carboxylate (100 mg, 0.492 mmol) and N-bromosuccinimide (119 mg, 0.669 mmol) in 5% fuming nitric acid in acetic acid (2 mL) was heated to 150° C. for 10 minutes via microwave. The reaction mixture was concentrated and purified by silica gel chromatography with hexanes/ethyl acetate (10/1) to afford methyl 4-bromo-5-phenylisoxazole-3-carboxylate (108 mg). The compound had an HPLC ret. time=3.21 min.–Column: YMC S5 COMBISCREEN® 4.6×50 mm; Gradient time: 4 min; Flow rate=4 ml/min; Solvent A=10% MeOH–90% Water–0.2% H₃PO₄; Solvent B=90% MeOH–10% water–0.2% H₃PO₄; Start % B=0; Final % B=100. LC-MS: M$^{+1}$=284$^+$.

9-C. Methyl 4-acetyl-5-phenylisoxazole-3-carboxylate

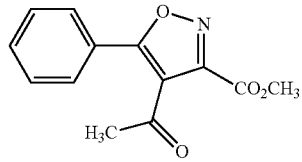

(9-C)

A solution of methyl 4-bromo-5-phenylisoxazole-3-carboxylate (358 mg, 1.269 mmol, prepared in a similar manner as described in step 9-B) and tributyl(1-ethoxyvinyl)tin (0.858 mL, 2.54 mmol) in dioxane (5 mL) was heated at 100° C. for 24 h. To the reaction mixture was added 1N aqueous hydrochloric acid (2.54 mL, 2.54 mmol), and the mixture was stirred at room temperature for 1 h. The reaction mixture was diluted with ethyl acetate (100 mL), washed with water (30 mL), washed with a saturated aqueous solution of sodium bicarbonate (30 mL), and washed with brine (30 mL). The mixture was concentrated to ~5 mL, and potassium fluoride (0.059 mL, 2.54 mmol) in 2 mL of water was added, and the mixture was stirred for 10 minutes. The solid was filtered and washed with ethyl acetate, and the filtrate was washed with water (10 mL), washed with brine (10 mL), and dried over anhydrous sodium sulfate. Concentration followed by purification by silica gel chromatography with hexanes/ethyl acetate (10/1) afforded methyl 4-acetyl-5-phenylisoxazole-3-carboxylate (105 mg). The compound had an HPLC ret. time=2.69 min.–Column: YMC S5 COMBISCREEN® 4.6×50 mm; Gradient time: 4 min; Flow rate=4 ml/min; Solvent A=10% MeOH–90% Water–0.2% H₃PO₄; Solvent B=90% MeOH–10% water–0.2% H₃PO₄; Start % B=0; Final % B=100. LC-MS: M$^{+1}$=246$^+$.

9-D. Methyl 4-(1,1-difluoroethyl)-5-phenylisoxazole-3-carboxylate

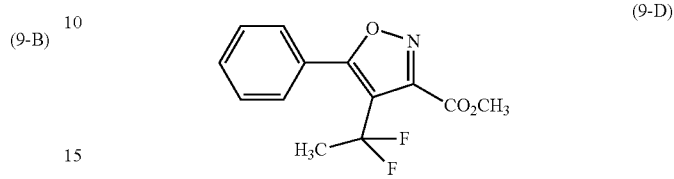

(9-D)

Methyl 4-acetyl-5-phenylisoxazole-3-carboxylate (105 mg, 0.428 mmol) was added to a reaction vessel containing ethanol (5.00 µL) and deoxofluor (513 µL, 2.78 mmol) was added, and the reaction mixture was heated to 85° C. for 6 h. The reaction mixture was quenched with 20 mL of a saturated aqueous solution of sodium bicarbonate while maintaining the temperature between 0-5° C. The mixture was extracted with ethyl acetate (30 mL), and the organic phase was washed with water (15 mL), washed with brine (15 mL), and dried over anhydrous sodium sulfate. Concentration followed by purification by silica gel chromatography with hexanes/ethyl acetate (9/1) afforded methyl 4-(1,1-difluoroethyl)-5-phenylisoxazole-3-carboxylate (63 mg). The compound had an HPLC ret. time=3.13 min.–Column. YMC S5 COMBISCREEN® 4.6×50 mm; Gradient time: 4 min; Flow rate=4 ml/min; Solvent A=10% MeOH–90% Water–0.2% H₃PO₄; Solvent B=90% MeOH–10% water–0.2% H₃PO₄; Start % B=0; Final % B=100. LC-MS: M$^{+1}$=268$^+$.

9-E. 4-(1,1-Difluoroethyl)-5-phenylisoxazole-3-carboxylic acid, sodium salt

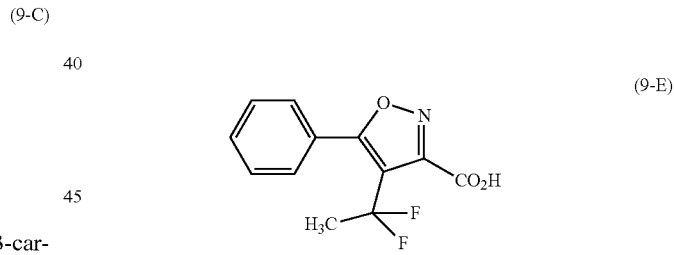

(9-E)

A solution of methyl 4-(1,1-difluoroethyl)-5-phenylisoxazole-3-carboxylate (62 mg, 0.232 mmol) and 1N aqueous sodium hydroxide (11.1 mg, 0.278 mmol) in methanol (1 mL) was stirred at 23° C. for 1 h. The reaction mixture was concentrated under reduced pressure to give 4-(1,1-difluoroethyl)-5-phenylisoxazole-3-carboxylic acid, sodium salt (68 mg). The compound had an HPLC ret. time=2.39 min.–Column. YMC S5 COMBISCREEN® 4.6×50 mm; Gradient time: 4 min; Flow rate=4 ml/min; Solvent A=10% MeOH–90% Water–0.2% H₃PO₄; Solvent B=90% MeOH–10% water–0.2% H₃PO₄; Start % B=0; Final % B=100. LC-MS: M$^{+1}$=254$^+$.

9. 1-(4-(5-(4-(1,1-Difluoroethyl)-5-phenylisoxazol-3-yl)-1,2,4-oxadiazol-3-yl)benzyl)-azetidine-3-carboxylic acid A solution of 4-(1,1-difluoroethyl)-5-phenylisoxazole-3-carboxylic acid (58.7 mg, 0.232 mmol), HOBt (64.0 mg, 0.418 mmol), and diisopropylethylamine (0.162 mL, 0.928 mmol) in acetonitrile (2 mL) was added EDC (105 mg, 0.545 mmol) and (Z)-tert-butyl 1-(4-(N'-hydroxycarbamimidoyl)benzyl)azetidine-3-carboxylate (Int.1, 70.8 mg, 0.232 mmol). The reaction mixture was stirred at 80° C. for 2 h and then concentrated. The residue was diluted with ethyl acetate (3 mL), washed with a saturated aqueous solution of sodium bicarbonate (1 mL), washed with water (1 mL), washed with brine (1 mL), and dried over anhydrous sodium sulfate. Concentration followed by purification by preparative HPLC gave tert-butyl 1-(4-(5-(4-(1,1-difluoropropyl)-5-phenylisoxazol-3-yl)-1,2,4-oxadiazol-3-yl)benzyl)azetidine-3-carboxylate.

A solution of tert-butyl 1-(4-(5-(4-(1,1-difluoropropyl)-5-phenylisoxazol-3-yl)-1,2,4-oxadiazol-3-yl)benzyl)azetidine-3-carboxylatein dichloromethane (0.5 mL) and trifluoroacetic acid (0.5 mL) was stirred at room temperature for 30 minutes. Concentration under reduced pressure afforded 1-(4-(5-(4-(1,1-Difluoroethyl)-5-phenylisoxazol-3-yl)-1,2,4-oxadiazol-3-yl)benzyl)-azetidine-3-carboxylic acid (19 mg). The compound had an HPLC ret. time=2.94 min.–Column: YMC COMBISCREEN® ODS-A 4.6×50 mm S-5; Gradient time: 4 min; Flow rate=4 ml/min; Solvent A=10% MeOH–90% Water–0.1% TFA; Solvent B=90% MeOH–10% water–0.1% TFA. LC-MS: $M^{+1}$=467+. $^1$H NMR (500 MHz, MeOD) δ ppm 2.24 (t, J=18.56 Hz, 3H) 3.64-3.73 (m, 1H), 4.35-4.39 (m, 4H), 4.52 (s, 2H), 7.58-7.67 (m, 3H), 7.70 (d, J=8.25 Hz, 2H), 7.76 (d, J=7.15 Hz, 2H), and 8.29 (d, J=8.25 Hz, 2H).

Example 10

1-(4-(5-(4-(1,1-Difluoropropyl)-5-phenylisoxazol-3-yl)-1,2,4-oxadiazol-3-yl)benzyl)azetidine-3-carboxylic acid, trifluoroacetic acid salt

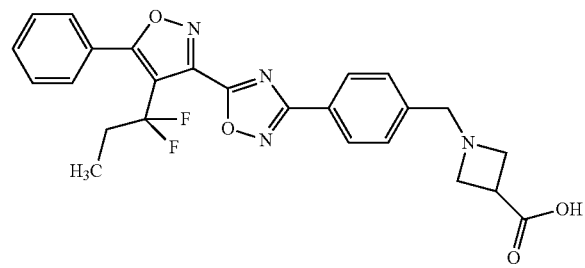

(10)

10-A. 1-Phenylpent-1-yn-3-ol

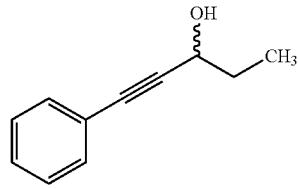

(10-A)

To a degassed solution of iodobenzene (0.110 mL, 0.980 mmol), bis(triphenylphosphine)palladium(II) chloride (41.3 mg, 0.059 mmol), copper(I) iodide (9.34 mg, 0.049 mmol), and diisopropylamine (0.559 mL, 3.92 mmol) in N,N-dimethylformamide (6 mL) was added pent-1-yn-3-ol (124 mg, 1.47 mmol). The reaction mixture was heated to 85° C. for 6 h. The reaction mixture was diluted with ethyl acetate (50 mL), washed with a 10% aqueous solution of lithium chloride (10 mL), washed with a 2M aqueous ammonium hydroxide (10 mL), washed with brine (10 mL), and dried over anhydrous sodium sulfate. Concentration followed by purification by silica gel chromatography with hexanes/ethyl acetate (3/1) afforded 1-Phenylpent-1-yn-3-ol (180 mg). The compound had an HPLC ret. time=2.74 min.–Column. YMC S5 COMBISCREEN® 4.6×50 mm; Gradient time: 4 min; Flow rate=4 ml/min; Solvent A=10% MeOH–90% Water–0.2% $H_3PO_4$; Solvent B=90% MeOH–10% water–0.2% $H_3PO_4$; Start % B=0; Final % B=100.

10-B. 1-Phenylpent-1-yn-3-one

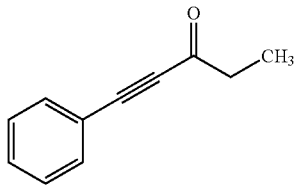

(10-B)

To a solution of oxalyl chloride (0.168 mL, 1.92 mmol) in dichloromethane (2.5 mL) at −78° C. was added dimethylsulfoxide (0.231 mL, 3.26 mmol) dropwise followed by 1-phenylpent-1-yn-3-ol (61.4 mg, 0.383 mmol) in 0.5 mL of dichloromethane dropwise. The reaction mixture was stirred at −78° C. for 1 h., and triethylamine (0.534 mL, 3.83 mmol) was then added dropwise. The reaction mixture was warmed to room temperature and stirred for 1 h. The reaction mixture was diluted with dichloromethane (2.5 mL), washed with water (1 mL), washed with a saturated aqueous solution of sodium bicarbonate (1 mL), washed with brine (1 mL), and dried over anhydrous sodium sulfate. Concentration followed by purification by silica gel chromatography with hexanes/ethyl acetate (10/1) afforded 1-phenylpent-1-yn-3-one (37 mg). The compound had an HPLC ret. time=2.88 min.–Column. YMC S5 COMBISCREEN® 4.6×50 mm; Gradient time: 4 min; Flow rate=4 ml/min; Solvent A=10% MeOH–90% Water–0.2% $H_3PO_4$; Solvent B=90% MeOH–10% water–0.2% $H_3PO_4$; Start % B=0; Final % B=100. LC-MS: $M^{+1}$=159+.

10-C. Ethyl 5-phenyl-4-propionylisoxazole-3-carboxylate

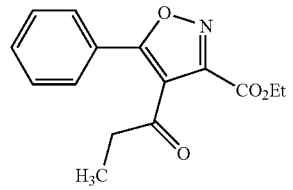

(10-C)

To a solution of 1-phenylpent-1-yn-3-one (36.7 mg, 0.232 mmol) and triethylamine (0.113 mL, 0.812 mmol) in toluene (1 mL) at 120° C. was added (Z)-ethyl 2-chloro-2-(hydroxyimino)acetate (105 mg, 0.696 mmol) in toluene (1 mL) dropwise. The reaction mixture was stirred at 120° C. for 16 h. To the reaction mixture was added additional (Z)-ethyl 2-chloro-2-(hydroxyimino)acetate (105 mg, 0.696 mmol) and triethylamine (0.113 mL, 0.812 mmol), and the reaction mixture was stirred at 140° C. for 3 days. The reaction mixture was concentrated, diluted with ethyl acetate (5 mL), washed with water (1 mL), washed with a saturated aqueous solution of sodium bicarbonate (1 mL), washed with brine (1 mL), and dried over anhydrous sodium sulfate. Concentration followed by purification by silica gel chromatography with hexanes/ethyl acetate (10/1) afforded ethyl 5-phenyl-4-propionylisoxazole-3-carboxylate (14.7 mg). The compound had an HPLC ret. time=3.15 min.–Column: YMC S5 COMBISCREEN® 4.6×50 mm; Gradient time: 4 min; Flow rate=4 ml/min; Solvent A=10% MeOH–90% Water–0.2% $H_3PO_4$; Solvent B=90% MeOH–10% water–0.2% $H_3PO_4$; Start % B=0; Final % B=100. LC-MS: 274$^+$.

10-D. Ethyl 4-(1,1-difluoropropyl)-5-phenylisoxazole-3-carboxylate

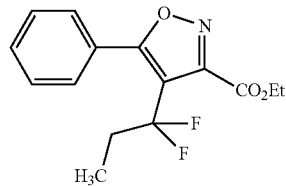

(10-D)

A mixture of ethyl 5-phenyl-4-propionylisoxazole-3-carboxylate (19.4 mg, 0.071 mmol), bis(2-methoxyethyl)aminosulfur trifluoride (131 µL, 0.710 mmol), and ethanol (0.829 µL, 0.014 mmol) was heated at 85° C. for 16 h. The reaction mixture was quenched with 2 mL of a saturated sodium bicarbonate while maintaining the temperature between 0-5° C. The reaction mixture was extracted with ethyl acetate (2×2 mL), and the organic phase was washed with water (1 mL), washed with brine (1 mL), and dried over anhydrous sodium sulfate. Concentration followed by purification on a preparative TLC plate with hexanes/ethyl acetate (9/1) afforded ethyl 4-(1,1-difluoropropyl)-5-phenylisoxazole-3-carboxylate (8.9 mg). The compound had an HPLC ret. time=3.47 min.– YMC S5 COMBISCREEN® 4.6×50 mm; Gradient time: 4 min; Flow rate=4 ml/min; Solvent A=10% MeOH–90% Water–0.2% $H_3PO_4$; Solvent B=90% MeOH–10% water–0.2% $H_3PO_4$; Start % B=0; Final % B=100. LC-MS: $M^{+1}$=296$^+$.

10-E. 4-(1,1-Difluoropropyl)-5-phenylisoxazole-3-carboxylic acid

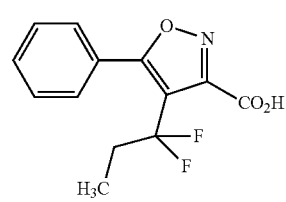

(10-E)

A solution of ethyl 4-(1,1-difluoropropyl)-5-phenylisoxazole-3-carboxylate (8.9 mg, 0.030 mmol) and 1N aqueous sodium hydroxide (36 µL, 0.036 mmol) in ethanol (1 mL) was stirred at room temperature for 30 minutes and then concentrated under reduced pressure. The residue was suspended in water (0.5 mL) and acidified with 1N aqueous hydrochloric acid to a pH of ~3. The aqueous solution was extracted with ethyl acetate (3×2 mL), and the combined organic layers were washed with water (1 mL), washed with brine (1 mL), and dried over anhydrous sodium sulfate. Concentration under reduced pressure afforded 4-(1,1-difluoropropyl)-5-phenylisoxazole-3-carboxylic acid (8.0 mg). The compound had an HPLC ret. time=2.69 min.–Column. YMC COMBISCREEN® ODS-A 4.6×50 mm S-5; Gradient time: 4 min; Flow rate=4 ml/min; Solvent A=10% MeOH–90% Water–0.1% TFA; Solvent B=90% MeOH–10% water–0.1% TFA.

10-F. 4-(1,1-Difluoropropyl)-5-phenylisoxazole-3-carbonyl fluoride

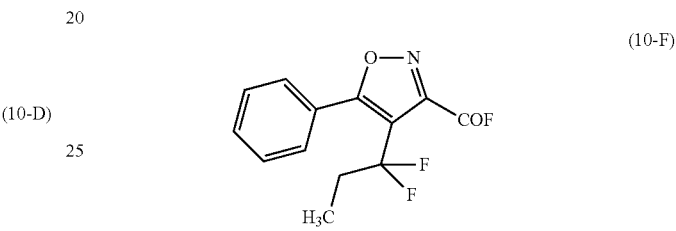

(10-F)

A solution of 4-(1,1-difluoropropyl)-5-phenylisoxazole-3-carboxylic acid (8.4 mg, 0.031 mmol) and pyridine (3.05 µL, 0.038 mmol) in dichloromethane (1 mL) was added cyanuric fluoride (3.18 µL, 0.038 mmol), and the reaction mixture was stirred at room temperature for 2 h. The reaction mixture was diluted with dichloromethane (2 mL) and washed with ice-water (2×1 mL). The aqueous layer was extracted with dichloromethane (2×1 mL), and the combined organic layers were washed brine (1 mL) and dried over anhydrous sodium sulfate. Concentration under reduced pressure afforded 4-(1,1-difluoropropyl)-5-phenylisoxazole-3-carbonyl fluoride (7.2 mg).

10. 1-(4-(5-(4-(1,1-Difluoropropyl)-5-phenylisoxazol-3-yl)-1,2,4-oxadiazol-3-yl)benzyl)-azetidine-3-carboxylic acid, 2,2,2-trifluoroacetic acid salt To a solution of 4-(1,1-difluoropropyl)-5-phenylisoxazole-3-carbonyl fluoride (7.2 mg, 0.027 mmol) and (Z)-tert-butyl 1-(4-(N'-hydroxycarbamimidoyl)benzyl)azetidine-3-carboxylate (Int.1, 8.17 mg, 0.027 mmol) in acetonitrile (1 mL) was added Hunig's Base (9.34 µL, 0.053 mmol), and the reaction mixture was stirred at room temperature for 3 days. The reaction mixture was concentrated and diluted with ethyl acetate (3 ml), washed with water (1 mL), washed with a saturated aqueous solution of sodium carbonate (1 mL), washed brine (1 mL), and dried over anhydrous sodium sulfate. The mixture was concentrated, dissolved in acetonitrile (1 mL), and a 1M solution of tetrabutylammonium fluoride in tetrahydrofuran (53 µL, 0.053 mmol) was added. The reaction mixture was stirred at room temperature for 5 h. The reaction mixture was concentrated, diluted with ethyl acetate (3 ml), washed with water (1 ml), washed with a saturated aqueous solution of sodium bicarbonate (1 ml), washed with brine (1 mL), and dried over anhydrous sodium sulfate. Concentration followed by purification by preparative HPLC afforded tert-butyl 1-(4-(5-(4-(1,1-difluoropropyl)-5-phenylisoxazol-3-yl)-1,2,4-oxadiazol-3-yl)benzyl)azetidine-3-carboxylate.

A solution of tert-butyl 1-(4-(5-(4-(1,1-difluoropropyl)-5-phenylisoxazol-3-yl)-1,2,4-oxadiazol-3-yl)benzyl)azetidine-3-carboxylate in dichloromethane (0.5 mL) and trifluoroacetic acid (0.5 mL) was stirred at room temperature for 30 minutes. The reaction mixture was concentrated under reduced pressure to give 1-(4-(5-(4-(1,1-difluoropropyl)-5-phenylisoxazol-3-yl)-1,2,4-oxadiazol-3-yl)benzyl)-azetidine-3-carboxylic acid, 2,2,2-trifluoroacetic acid salt (1.8 mg). The compound had an HPLC ret. time=3.15 min.–Column. YMC COMBISCREEN® ODS-A 4.6×50 mm S-5; Gradient time: 4 min; Flow rate=4 ml/min; Solvent A=10% MeOH–90% Water–0.1% TFA; Solvent B=90% MeOH–10% water–0.1% TFA. LC-MS: 481$^+$. $^1$H NMR (500 MHz, MeOH) δ ppm 1.06 (t, J=7.56 Hz, 3H), 2.46-2.59 (m, 2H), 3.70 (quin, J=8.25 Hz, 1H), 4.33-4.41 (m, 4H), 4.53 (s, 2H), 7.58-7.67 (m, 3H), 7.70 (d, J=8.25 Hz, 2H), 7.75 (d, J=7.15 Hz, 2H), and 8.28 (d, J=8.25 Hz, 2H).

Example 11

1-(4-(5-(3-Phenyl-4-propylisoxazol-5-yl)-1,2,4-oxadiazol-3-yl)benzyl)azetidine-3-carboxylic acid, 2,2,2-trifluoroacetic acid salt

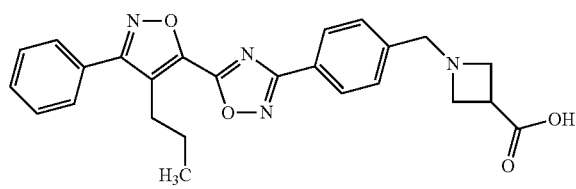

(11)

11-A. Ethyl 2-bromohex-2-enoate

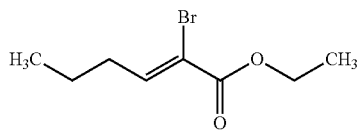

(11-A)

To a suspension of NaH, 60% (0.800 g, 20.00 mmol) in THF (40 mL), cooled in an adiabatic cooling bath, was added, portion wise over 15 minutes, triethylphosphonoacetate (4.00 mL, 20 mmol). The reaction mixture was allowed to stir at rt for 45 minutes. At this time, bromine (1.030 mL, 20.00 mmol) was added dropwise over 15 minutes. The orange color discharged immediately after each drop hit the reaction. However, when the addition was complete a light orange color persisted and the reaction mixture was a light orange suspension. This suspension was warmed to 40° C. for 10 minutes and was then allowed to stir at rt for 1 hr. The reaction mixture was cooled to 10° C. NaH, 60% (0.800 g, 20.00 mmol) was added in one portion and the reaction mixture was allowed to warm to rt and stir for 45 minutes. Gas evolution was observed. Butyraldehyde (1.803 mL, 20.00 mmol) was then added over 2 minutes and the reaction mixture was stirred at rt for 18 hrs. The reaction mixture was partitioned between Et$_2$O (200 ml) and water (100 ml). The organic layer was washed with saturated sodium bicarbonate solution (150 ml), water (100 ml) and brine (100 ml). After drying (MgSO$_4$) and filtration, the organic layer was concentrated to a light yellow liquid that was chromatographed on a 5×20 cm silica gel column, eluting with a 0-5% EtOAc/Hex gradient. The fractions containing product were concentrated to afford (Z)-ethyl 2-bromohex-2-enoate (3.61 g, 16.33 mmol, 82% yield) as a colorless liquid. HPLC retention time=1.81 minutes (PHENOMENEX® Luna 4.6×30 mm S-5 ODS column) eluting with 10-90% aqueous methanol+0.1% TFA over a 2 minute gradient. MS: (M+H)=221/223.08. Note: The product is a ~3:1 mixture of olefin isomers. The mixture was used as is in the next step.

11-B. Ethyl 3-phenyl-4-propylisoxazole-5-carboxylate

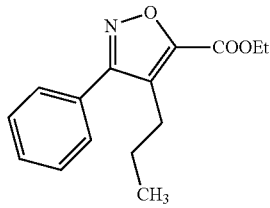

(11-B)

To a solution of (Z)-N-hydroxybenzimidoyl chloride (770 mg, 4.95 mmol) and ethyl 2-bromohex-2-enoate (1.09 g, 4.95 mmol) in DCM (15 mL) was added triethylamine (2.07 mL, 14.85 mmol) over 5 minutes. After ~50% of the addition was complete, a precipitate formed. Stirring was continued for 24 hr at rt. The reaction mixture was partitioned between Et$_2$O (100 ml) and water (100 ml). The organic layer was washed with brine (100 ml), dried (MgSO$_4$) and concentrated to afford a yellow oil. This oil was chromatographed on a 5×15 cm silica gel column, eluting with a 0-8% EtOAc/Hex gradient. The product containing fractions were concentrated to afford 343 mg of a waxy, white solid. This material was triturated with heptane. The solid contained no product. The mother liquor was concentrated to afford a partially purified semisolid residue. The portion of the residue that dissolved in ~3 ml of hexane was chromatographed on a 12 gm Isco silica gel cartridge, eluting with a 0-1% EtOAc/Hex gradient. Fractions containing the product were concentrated to afford ethyl 3-phenyl-4-propylisoxazole-5-carboxylate (34 mg, 0.131 mmol, 2.65% yield) as a colorless oil. HPLC retention time=1.91 minutes (PHENOMENEX® Luna 4.6×30 mm S-5 ODS column) eluting with 10-90% aqueous methanol+0.1% TFA over a 2 minute gradient. MS: (M+H)=260.23. $^1$H NMR (500 MHz, chloroform-d) δ ppm 0.90 (t, J=7.4 Hz, 3H), 1.45 (t, J=7.2 Hz, 3H), 1.53 (m, 2H), 2.80 (m, 2H), 4.46 (q, J=7.2 Hz, 2H), 7.45 (m, 1H), 7.50 (m, 2H), 7.59 (m, 2H).

By $^1$H NMR, there is a ~15% impurity containing an ethyl ester and a propyl group suggestive of the regioisomeric product. This material was used in the next step without further purification.

11-C. 3-Phenyl-4-propylisoxazole-5-carboxylic acid, lithium salt

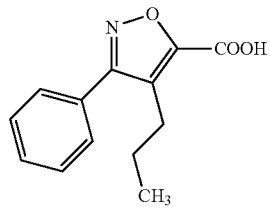

(11-C)

To a mixture of the product of step 11-B (27 mg, 0.104 mmol) in methanol (0.8 mL) and water (0.2 mL) was added LiOH, hydrate (4.37 mg, 0.104 mmol) and stirring was continued overnight at rt. The volatiles were removed in vacuo to afford 3-phenyl-4-propylisoxazole-5-carboxylic acid, lithium salt and its presumed regioisomer (24 mg, 0.101 mmol, 97% yield) as a colorless oil that was used without further purification. HPLC retention time=1.66 minutes (PHENOMENEX® Luna 4.6×30 mm S-5 ODS column) eluting with 10-90% aqueous methanol+0.1% TFA over a 2 minute gradient. MS: (M+H)=232.17.

11-D. tert-Butyl 1-(4-(5-(3-phenyl-4-propylisoxazol-5-yl)-1,2,4-oxadiazol-3-yl)benzyl)azetidine-3-carboxylate

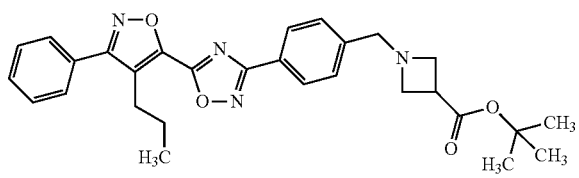

(11-D)

A mixture of 3-phenyl-4-propylisoxazole-5-carboxylic acid, lithium salt (23.12 mg, 0.1 mmol), (Z)-tert-butyl 1-(4-(N'-hydroxycarbamimidoyl)benzyl)azetidine-3-carboxylate, Int.1 (30.5 mg, 0.1 mmol), HOBT (16.85 mg, 0.110 mmol), diisopropylethylamine (0.044 mL, 0.250 mmol) and EDC (23.00 mg, 0.120 mmol) was stirred in DMF (1 mL) at rt for 18 hr. Additional EDC (23.00 mg, 0.120 mmol) was added and the reaction mixture was stirred at 60° C. for 5 hr. The reaction mixture was partitioned between EtOAc (30 mL) and saturated sodium bicarbonate solution (30 mL). The organic layer was washed with water (2×25 mL), brine (25 mL), dried (MgSO$_4$) and concentrated to afford an oil that was chromatographed on a 4 gm Isco silica gel cartridge, eluting with a 0-50% EtOAc/Hex gradient. The essentially pure fractions containing product were concentrated to afford tert-butyl 1-(4-(5-(3-phenyl-4-propylisoxazol-5-yl)-1,2,4-oxadiazol-3-yl)benzyl)azetidine-3-carboxylate (22 mg, 0.044 mmol, 43.9% yield) as a colorless oil. HPLC retention time=1.84 minutes (PHENOMENEX® Luna 4.6×30 mm S-5 ODS column) eluting with 10-90% aqueous methanol+0.1% TFA over a 2 minute gradient. MS: (M+H)=501.21.

11. 1-(4-(5-(3-Phenyl-4-propylisoxazol-5-yl)-1,2,4-oxadiazol-3-yl)benzyl)azetidine-3-carboxylic acid, 2,2,2-trifluoroacetic acid salt A solution of tert-butyl 1-(4-(5-(3-phenyl-4-propylisoxazol-5-yl)-1,2,4-oxadiazol-3-yl)benzyl)azetidine-3-carboxylate (22 mg, 0.044 mmol) in TFA (0.5 mL) was allowed to stand at rt for 2.5 hr. The volatiles were removed in vacuo and the residue was triturated with Et$_2$O and dried to afford 1-(4-(5-(3-phenyl-4-propylisoxazol-5-yl)-1,2,4-oxadiazol-3-yl)benzyl)azetidine-3-carboxylic acid, 2,2,2-trifluoroacetic acid salt (16 mg, 0.028 mmol, 63.0% yield) as an off-white solid. HPLC retention time=3.17 minutes (YMC-Combi 4.6×30 mm S-5 ODS column) eluting with 10-90% aqueous methanol+0.2% phosphoric acid over a 4 minute gradient. MS: (M+H)=445.18. $^1$H NMR (400 MHz, MeOD) δ ppm 0.97 (t, J=7.4 Hz, 3H), 1.66 (m, 2H), 3.09 (t, J=7.8 Hz, 2H), 3.71 (m, 1H), 4.39 (m, 4H), 4.54 (s, 2H), 7.61 (m, 3H), 7.72 (m, 4H), 8.31 (d, J=8.3 Hz, 2H).

Example 12

1-(4-(5-(4-(Difluoromethyl)-3-phenylisoxazol-5-yl)-1,2,4-oxadiazol-3-yl)benzyl)azetidine-3-carboxylic acid, 2,2,2-trifluoroacetic acid salt

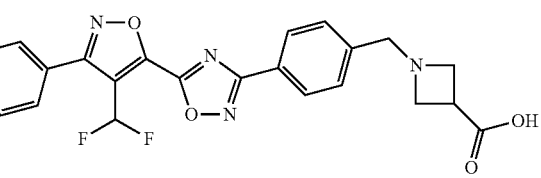

(12)

12-A. (E)-Methyl 4,4-dimethoxy-2-(phenylsulfinyl)but-2-enoate

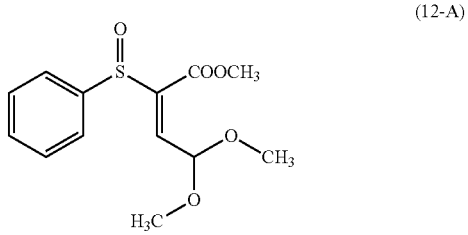 [SMILES: COC(=O)/C(=C\C(OC)OC)S(=O)c1ccccc1]

(12-A)

A mixture of methyl 2-(phenylsulfinyl)acetate (1 g, 5.04 mmol), 2,2-dimethoxyacetaldehyde (3.15 ml, 10.09 mmol) and piperidine (0.999 ml, 10.09 mmol) in acetonitrile (20 ml) was heated to 60° C. for 18 hr. After cooling to rt, the volatiles were removed in vacuo and the residue was chromatographed on a 5×12 cm silica gel column, eluting with a 0-40% EtOAc/Hex gradient. The pure fractions were concentrated to afford (E)-methyl 4,4-dimethoxy-2-(phenylsulfinyl)but-2-enoate (1.42 g, 4.99 mmol, 99% yield) as a light yellow oil. HPLC retention time=1.23 minutes (PHENOMENEX® Luna 4.6×30 mm S-5 ODS column) eluting with 10-90% aqueous methanol+0.1% TFA over a 2 minute gradient. MS: (M+Na)=307.06. $^1$H NMR (500 MHz, chloroform-d) δ ppm 3.40 (s, 3H), 3.41 (s, 3H), 3.69 (s, 3H), 5.71 (d, J=7.2 Hz, 1H), 7.07 (d, J=6.6 Hz, 1H), 7.48 (m, 3H), 7.66 (m, 2H).

12-B. Methyl 4-(dimethoxymethyl)-3-phenylisoxazole-5-carboxylate

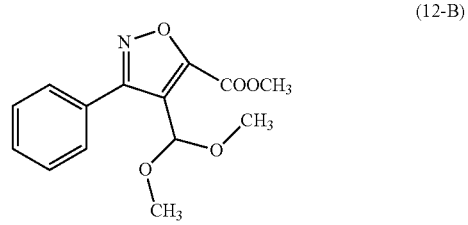 [SMILES: COC(=O)c1onc(-c2ccccc2)c1C(OC)OC]

(12-B)

12-B was prepared as described below in a similar manner as the t-Butyl ester as reported by Garcia Ruano, J. L. et al., *Tetrahedron*, 14491-14500 (1999).

To a solution of (E)-methyl 4,4-dimethoxy-2-(phenylsulfinyl)but-2-enoate (0.284 g, 1 mmol) and (Z)-N-hydroxybenzimidoyl chloride (0.370 g, 2.378 mmol) in DCM (5 mL) at rt was added Et₃N (0.488 mL, 3.50 mmol) dropwise over 30 minutes as a solution in 5 mL of DCM. After stirring 18 hr at rt, the reaction mixture was cooled to 0° C. and additional (Z)-N-hydroxybenzimidoyl chloride (0.370 g, 2.378 mmol) was added. The cooling bath was removed and the reaction mixture stirred for 2 hr during which the temperature of the reaction reached rt, Et₃N (0.488 mL, 3.50 mmol) was added over ~2 minutes. The reaction mixture was stirred an additional 18 hr at rt. The reaction mixture was poured into ~100 ml of hexane. The resulting suspension was allowed to stand at rt for 30 minutes. After filtration, the filtrate was concentrated and the residue was chromatographed on a 5×12 cm silica gel column, eluting with a 0-6% EtOAc/Hex gradient. (Note: to load the column, the residue was slurried in 5% CH₂Cl₂/Hex. Not all of the material dissolved). The essentially pure fractions containing the product were concentrated to afford methyl 4-(dimethoxymethyl)-3-phenylisoxazole-5-carboxylate (125 mg, 0.451 mmol, 45.1% yield) as a colorless oil. (Note: The desired product is the third product to elute and began eluting at 6% EtOAc/Hex.). HPLC retention time=1.63 minutes (PHENOMENEX® Luna 4.6×30 mm S-5 ODS column) eluting with 10-90% aqueous methanol+0.1% TFA over a 2 minute gradient. MS: (M+H)=278.12. ¹H NMR (400 MHz, chloroform-d) δ ppm 3.41 (s, 6H), 4.03 (s, 3H), 5.95 (s, 1H), 7.45 (m, 3H), 7.96 (dd, J=7.8, 2.0 Hz, 2H).

12-C. Methyl 4-formyl-3-phenylisoxazole-5-carboxylate

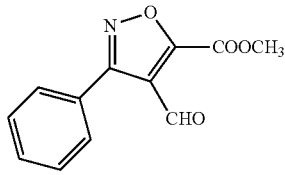

(12-C)

A mixture of methyl 4-(dimethoxymethyl)-3-phenylisoxazole-5-carboxylate (88 mg, 0.317 mmol) and Amberlyst 15 ion exchange resin, dry (250 mg) in CHCl₃ (5 mL) was stirred at rt for 18 hr. The resin was filtered off and the filtrate was concentrated to afford methyl 4-formyl-3-phenylisoxazole-5-carboxylate (73 mg, 0.316 mmol, 99% yield) as a colorless oil that was used in the next step without further purification.

12-D. Methyl 4-(difluoromethyl)-3-phenylisoxazole-5-carboxylate

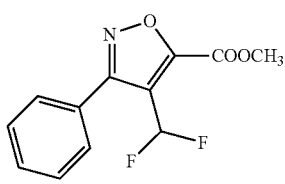

(12-D)

To a solution of methyl 4-formyl-3-phenylisoxazole-5-carboxylate (70 mg, 0.303 mmol) in CH₂Cl₂ (1.5 mL) at rt was added [Bis(2-methoxyethyl)amino]sulfur trifluoride (0.095 mL, 0.515 mmol), followed by ethanol (3.54 µL, 0.061 mmol). The reaction mixture was stirred at rt for 4 days. The reaction mixture was partitioned between EtOAc (30 mL) and saturated sodium bicarbonate solution (30 mL). After drying (MgSO₄) and filtration, the organic layer was concentrated to an oil which was chromatographed on a 4 gm Isco silica gel cartridge, eluting with a 0-4% EtOAc/Hex gradient. The fractions containing essentially pure product were concentrated to afford methyl 4-(difluoromethyl)-3-phenylisoxazole-5-carboxylate (34 mg, 0.134 mmol, 44.4% yield) as a colorless oil. HPLC retention time=1.69 minutes (PHENOMENEX® Luna 4.6×30 mm S-5 ODS column) eluting with 10-90% aqueous methanol+0.1% TFA over a 2 minute gradient. MS: (M+H)=254.10.

12-E. 4-(Difluoromethyl)-3-phenylisoxazole-5-carboxylic acid, lithium salt

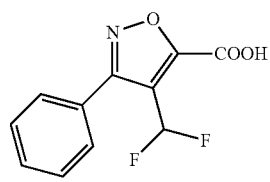

(12-E)

To a solution of methyl 4-(difluoromethyl)-3-phenylisoxazole-5-carboxylate (29 mg, 0.115 mmol) in methanol (1 mL) and water (0.2 mL) was added LiOH, hydrate (4.81 mg, 0.115 mmol) and the mixture was stirred at rt for 1 hr. The volatiles were removed in vacuo to afford 4-(difluoromethyl)-3-phenylisoxazole-5-carboxylic acid, lithium salt (28 mg, 0.114 mmol, 99% yield) as a colorless oil. HPLC retention time=1.45 minutes (PHENOMENEX® Luna 4.6×30 mm S-5 ODS column) eluting with 10-90% aqueous methanol+0.1% TFA over a 2 minute gradient. MS: (M+H)=240.12.

12-F. tert-Butyl 1-(4-(5-(4-(difluoromethyl)-3-phenylisoxazol-5-yl)-1,2,4-oxadiazol-3-yl)benzyl)azetidine-3-carboxylate

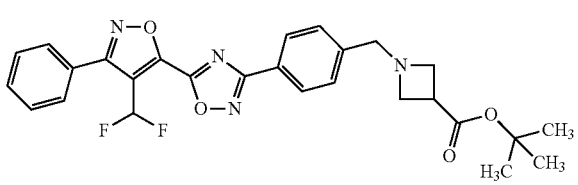

(12-F)

A mixture of 4-(difluoromethyl)-3-phenylisoxazole-5-carboxylic acid (28 mg, 0.117 mmol), (Z)-tert-butyl 1-(4-(N'-hydroxycarbamimidoyl)benzyl)azetidine-3-carboxylate, Int.1, (35.7 mg, 0.117 mmol), HOBT (28.7 mg, 0.187 mmol), EDC (52.7 mg, 0.275 mmol) and diisopropylethylamine (82 µL, 0.468 mmol) in DMF was stirred at rt for 3 hr and at 55° C. for 18 hr. The reaction mixture was partitioned between EtOAc (30 ml) and saturated sodium bicarbonate solution (30 ml). The organic layer was washed with water (2×30 ml) and brine (30 ml). After drying (MgSO₄) and filtration, the organic layer was concentrated to a yellow oil that was chromatographed on a 4 gm Isco silica gel cartridge, eluting with a 0-50% EtOAc/Hex gradient. The essentially pure fractions containing the product were concentrated to afford tert-butyl 1-(4-(5-(4-(difluoromethyl)-3-phenylisoxazol-5-yl)-1,2,4-oxadiazol-3-yl)benzyl)azetidine-3-carboxylate (23 mg, 0.045 mmol, 38.6% yield) as a white solid. HPLC retention time=1.80 minutes (PHENOMENEX® Luna 4.6×30 mm S-5 ODS column) eluting with 10-90% aqueous methanol+0.1% TFA over a 2 minute gradient. MS: (M+H)=509.14.

12. 1-(4-(5-(4-(Difluoromethyl)-3-phenylisoxazol-5-yl)-1,2,4-oxadiazol-3-yl)benzyl)azetidine-3-carboxylic acid, 2,2,2-trifluoroacetic acid salt A solution of tert-butyl 1-(4-(5-(4-(difluoromethyl)-3-phenylisoxazol-5-yl)-1,2,4-oxadiazol-3-yl)benzyl)azetidine-3-carboxylate (23 mg, 0.045 mmol) in TFA (0.5 mL) was allowed to stand at rt for 1.5 hr. At this time, the volatiles were removed in vacuo and the residue was triturated with ether. Drying afforded 1-(4-(5-(4-(difluoromethyl)-3-phenylisoxazol-5-yl)-1,2,4-oxadiazol-3-yl)benzyl)azetidine-3-carboxylic acid, 2,2,2-trifluoroacetic acid salt (14 mg, 0.025 mmol, 54.6% yield) as an off-white solid. HPLC retention time=3.03 minutes (YMC Combi 4.6×50 mm S-5 ODS column) eluting with 10-90% aqueous methanol+0.2% phosphoric acid over a 4 minute gradient. MS: (M+H)=453.11. $^1$H NMR (400 MHz, MeOD) δ ppm 3.74 (m, 1H), 4.40 (m, 4H), 4.56 (s, 2H), 7.56 (m's, 6H), 7.87 (m, 2H), 8.34 (d, J=8.3 Hz, 2H).

Example 13

1-(4-(5-(4-(Methoxycarbonyl)-3-phenylisoxazol-5-yl)-1,2,4-oxadiazol-3-yl)benzyl)azetidine-3-carboxylic acid, 2,2,2-trifluoroacetic acid salt

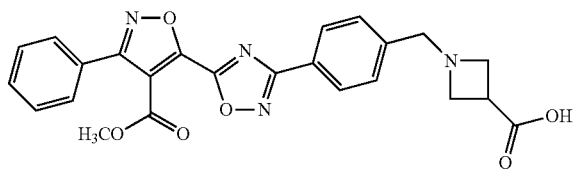

(13)

13-A. Dimethyl 3-phenylisoxazole-4,5-dicarboxylate

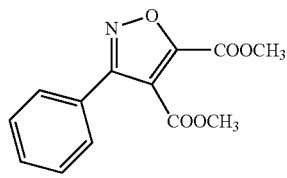

(13-A)

To a solution of (Z)-N-hydroxybenzimidoyl chloride (467 mg, 3 mmol) and dimethyl but-2-ynedioate (0.374 mL, 3.00 mmol) in Et$_2$O (10 mL) at rt was added dropwise over 5 minutes Et$_3$N (0.460 mL, 3.30 mmol). The reaction mixture became a thick suspension and was stirred at rt for 2 hr. After filtration, the filtrate was concentrated to an oil that was chromatographed on a 24 gm Isco silica gel cartridge, eluting with a 0-25% EtOAc/Hex gradient. The pure fractions were concentrated to afford dimethyl 3-phenylisoxazole-4,5-dicarboxylate (780 mg, 2.99 mmol, 100% yield) as a colorless oil. HPLC retention time=2.86 minutes (YMC Combi 4.6×50 mm S-5 ODS column) eluting with 10-90% aqueous methanol+0.2% phosphoric acid over a 4 minute gradient. MS: (M+H)=262.15. $^1$H NMR (500 MHz, CDCl$_3$) d ppm 3.91 (s, 2H) 4.02 (s, 2H) 7.46-7.53 (m, 2H) 7.69 (d, J=6.6 Hz, 1H).

13-B. 4-(Methoxycarbonyl)-3-phenylisoxazole-5-carboxylic acid

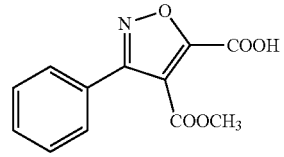

(13-B)

To a solution of dimethyl 3-phenylisoxazole-4,5-dicarboxylate (770 mg, 2.95 mmol) in MeOH (15 mL)/water (5.00 mL) at rt was added LiOH, hydrate (124 mg, 2.95 mmol) and the reaction mixture was allowed to stir at rt for 1 hr. The MeOH was removed in vacuo and the remaining aqueous solution was diluted with water (5 mL). The pH was adjusted to <1 with 1N HCl and the mixture was extracted with EtOAc (40 mL). The organic layer was washed with brine (25 mL), dried (MgSO$_4$) and concentrated to afford 4-(methoxycarbonyl)-3-phenylisoxazole-5-carboxylic acid (709 mg, 2.87 mmol, 97% yield) as a colorless oil. HPLC retention time=1.99 minutes (YMC Combi 4.6×50 mm S-5 ODS column) eluting with 10-90% aqueous methanol+0.2% phosphoric acid over a 4 minute gradient. MS: (M+H)=248.13. $^1$H NMR (400 MHz, chloroform-d) δ ppm 3.89 (s, 3H) 7.51 (m, 5H).

13-C. Methyl 5-(fluorocarbonyl)-3-phenylisoxazole-4-carboxylate

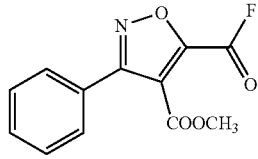

(13-C)

To a solution of 4-(methoxycarbonyl)-3-phenylisoxazole-5-carboxylic acid (100 mg, 0.405 mmol) and pyridine (0.039 mL, 0.485 mmol) in DCM (4 mL) at rt was added cyanuric fluoride (0.041 mL, 0.485 mmol) and the reaction mixture was stirred at rt for 2 hr. The reaction mixture was diluted with dichloromethane (20 ml) and washed with ice-cold 0.5N HCl (20 mL). The aqueous layer was extracted with DCM (10 mL) and the combined organic layers were dried (MgSO$_4$), filtered and concentrated to afford methyl 5-(fluorocarbonyl)-3-phenylisoxazole-4-carboxylate (100 mg, 0.401 mmol, 99% yield) as a colorless oil. The compound was found to react readily with methanol and was characterized as the methyl ester. HPLC retention time=1.59 minutes (PHENOMENEX® Luna 4.6×30 mm S-5 ODS column) eluting with 10-90% aqueous methanol+0.1% TFA over a 2 minute gradient. MS: (M+H)=262.15 (methyl ester).

13-D. Methyl 5-(3-(4-((3-(tert-butoxycarbonyl)azetidin-1-yl)methyl)phenyl)-1,2,4-oxadiazol-5-yl)-3-phenylisoxazole-4-carboxylate

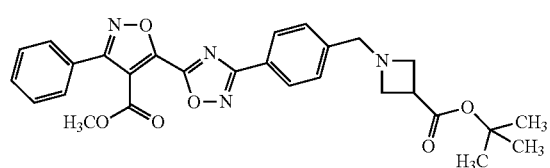

(13-D)

To a mixture of methyl 5-(fluorocarbonyl)-3-phenylisoxazole-4-carboxylate (99 mg, 0.397 mmol) and (Z)-tert-butyl 1-(4-(N'-hydroxycarbamimidoyl)benzyl)azetidine-3-carboxylate (121 mg, 0.397 mmol) in acetonitrile (2 mL) at rt was added diisopropylethylamine (0.083 mL, 0.477 mmol) and the reaction mixture was allowed to stir at rt over the weekend. The reaction mixture was partitioned between EtOAc (30 mL) and water (30 mL). The organic layer was washed with brine (20 mL), dried (MgSO₄) and concentrated to afford a white solid that was chromatographed on a 12 gm Isco silica gel cartridge, eluting with a 0-100% EtOAc/Hex gradient. The essentially pure fractions containing product were concentrated to afford methyl 5-(3-(4-((3-(tert-butoxycarbonyl)azetidin-1-yl)methyl)phenyl)-1,2,4-oxadiazol-5-yl)-3-phenylisoxazole-4-carboxylate (128 mg, 0.248 mmol, 62.4% yield) as a white solid. HPLC retention time=1.78 minutes (YMC Combi 4.6×30 mm S-5 ODS column) eluting with 10-90% aqueous methanol+0.1 TFA a 2 minute gradient. MS: (M+H)=517.22. $^1$H NMR (400 MHz, chloroform-d) d ppm 1.45 (s, 9H) 3.23-3.32 (m, 3H) 3.51-3.58 (m, 2H) 3.68 (s, 2H) 3.95 (s, 3H) 7.44 (d, J=8.0 Hz, 2H) 7.48-7.56 (m, 3H) 7.75 (dd, J=7.91, 1.63 Hz, 2H) 8.11 (d, J=8.3 Hz, 2H).

13. 1-(4-(5-(4-(Methoxycarbonyl)-3-phenylisoxazol-5-yl)-1,2,4-oxadiazol-3-yl)benzyl)azetidine-3-carboxylic acid, 2,2,2-trifluoroacetic acid salt A solution of methyl 5-(3-(4-((3-(tert-butoxycarbonyl)azetidin-1-yl)methyl)phenyl)-1,2,4-oxadiazol-5-yl)-3-phenylisoxazole-4-carboxylate (22 mg, 0.043 mmol) in TFA (0.5 mL) was allowed to stand at rt for 1.5 hr. The volatiles were removed in vacuo and the residue was co-evaporated from EtOAc/Heptane (3×2 mL) and dried under high vacuum to afford 1-(4-(5-(4-(methoxycarbonyl)-3-phenylisoxazol-5-yl)-1,2,4-oxadiazol-3-yl)benzyl)azetidine-3-carboxylic acid, 2,2,2-trifluoroacetic acid salt (24 mg, 0.042 mmol, 98% yield) as a white powder. HPLC retention time=2.84 minutes (YMC Combi 4.6×50 mm S-5 ODS column) eluting with 10-90% aqueous methanol+0.2% phosphoric acid over a 4 minute gradient. MS: (M+H)=461.18. $^1$H NMR (400 MHz, MeOD) d ppm 3.67-3.77 (m, 1H) 3.93 (s, 3H) 4.39 (m, 4H) 4.53 (s, 2H) 7.50-7.62 (m, 3H) 7.66-7.77 (m, 4H) 8.28 (d, J=8.0 Hz, 2H).

Example 14

1-(4-(5-(4-(Methylcarbamoyl)-3-phenylisoxazol-5-yl)-1,2,4-oxadiazol-3-yl)benzyl)azetidine-3-carboxylic acid, 2,2,2-trifluoroacetic acid salt

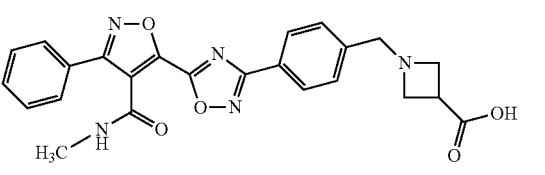

(14)

14-A. 5-(Methoxycarbonyl)-3-phenylisoxazole-4-carboxylic acid

(14-A)

To a solution of methyl 4-(dimethoxymethyl)-3-phenylisoxazole-5-carboxylate, 12-B, (144 mg, 0.519 mmol) in acetone (3 mL) at rt was added Jones' Reagent (0.539 mL, 0.727 mmol) and the resulting mixture was allowed to stir at rt for 1 hr. Three additional aliquots of Jones' Reagent (0.539 mL, 0.727 mmol) were added portion wise over 1 hr and stirring was continued at rt for 2 hr. At this time, the reaction mixture was partitioned between EtOAc (30 mL) and 2% NaHSO₃ solution (30 mL). The organic layer was washed with brine (20 mL), dried (MgSO₄) and concentrated to afford 5-(methoxycarbonyl)-3-phenylisoxazole-4-carboxylic acid (108 mg, 0.437 mmol, 84% yield) as a light yellow solid. HPLC retention time=1.30 minutes (PHENOMENEX® Luna 4.6×30 mm S-5 ODS column) eluting with 10-90% aqueous methanol+0.1% TFA over a 2 minute gradient. MS: (M+H)=248.13. $^1$H NMR (400 MHz, chloroform-d) δ ppm 4.16 (s, 3H), 7.50 (m, 3H), 7.66 (dd, J=8.2, 1.4 Hz, 2H).

14-B. Methyl 4-(methylcarbamoyl)-3-phenylisoxazole-5-carboxylate

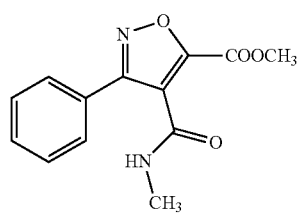

(14-B)

A mixture of 5-(methoxycarbonyl)-3-phenylisoxazole-4-carboxylic acid (50 mg, 0.202 mmol), methylamine hydrochloride (19.12 mg, 0.283 mmol), HOBT (37.2 mg, 0.243 mmol), EDC (46.5 mg, 0.243 mmol) and diisopropylethylamine (0.141 mL, 0.809 mmol) in DMF was stirred at rt for 22 hr. The reaction mixture was partitioned between EtOAc (30 mL) and water (30 mL). The organic layer was washed with saturated potassium bisulfate solution (30 ml), saturated sodium bicarbonate solution (30 mL) and brine (30 mL). After drying (MgSO$_4$) and filtration, the organic layer was concentrated to afford methyl 4-(methylcarbamoyl)-3-phenylisoxazole-5-carboxylate (38 mg, 0.146 mmol, 72.2% yield) as a tan solid. HPLC retention time=1.09 minutes (YMC Combi 4.6×30 mm S-5 ODS column) eluting with 10-90% aqueous methanol+0.1 TFA a 2 minute gradient. MS: (M+H)=261.15. $^1$H NMR (400 MHz, chloroform-d) d ppm 2.97 (d, J=4.77 Hz, 3H) 4.04 (s, 3 H) 7.19 (brs, 1H) 7.42-7.51 (m, 3H) 7.66-7.73 (m, 2H).

14-C. 4-(Methylcarbamoyl)-3-phenylisoxazole-5-carboxylic acid

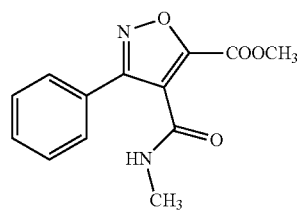

(14-C)

To a suspension of methyl 4-(methylcarbamoyl)-3-phenylisoxazole-5-carboxylate (35 mg, 0.134 mmol) in MeOH (0.8 mL) and water (0.2 mL) was added LiOH, Hydrate (6.77 mg, 0.161 mmol) and the mixture was allowed to stir at rt for 1 hr. during which time the reaction became homogeneous. The volatiles were removed in vacuo and the residue was partitioned between DCM (20 mL) and saturated potassium bisulfate solution (10 mL). The aqueous layer was extracted with DCM (10 mL) and the combined organic layers were dried (MgSO$_4$) and concentrated to afford 4-(methylcarbamoyl)-3-phenylisoxazole-5-carboxylic acid (33 mg, 0.134 mmol, 100% yield) as a slightly off-white foam. HPLC retention time=0.88 minutes (YMC Combi 4.6×30 mm S-5 ODS column) eluting with 10-90% aqueous methanol+0.1 TFA a 2 minute gradient. MS: (M+H)=247.13.

14-D. tert-Butyl 1-(4-(5-(4-(methylcarbamoyl)-3-phenylisoxazol-5-yl)-1,2,4-oxadiazol-3-yl)benzyl)azetidine-3-carboxylate

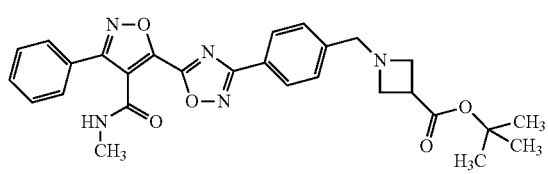

(14-D)

A mixture of 4-(methylcarbamoyl)-3-phenylisoxazole-5-carboxylic acid (32 mg, 0.130 mmol), (Z)-tert-butyl 1-(4-(N'-hydroxycarbamimidoyl)benzyl)azetidine-3-carboxylate, Int.1, (39.7 mg, 0.130 mmol), HOBT (31.8 mg, 0.208 mmol), EDC (58.5 mg, 0.305 mmol) and diisopropylethylamine (0.091 mL, 0.520 mmol) in DMF (1 mL) was stirred at rt for 18 hr. After warming to 60° C. for 3 hr, the reaction mixture was partitioned between EtOAc (30 mL) and saturated sodium bicarbonate solution (30 mL). The organic layer was washed with water (2×30 mL) and brine (30 mL). After drying (MgSO$_4$) and filtration, the organic layer was concentrated to a yellow oil that was chromatographed on a 4 gm Isco silica gel cartridge, eluting with a 0-90% EtOAc/Hex gradient. The essentially pure fractions containing product were concentrated to afford tert-butyl 1-(4-(5-(4-(methylcarbamoyl)-3-phenylisoxazol-5-yl)-1,2,4-oxadiazol-3-yl)benzyl)azetidine-3-carboxylate (29 mg, 0.056 mmol, 43.3% yield) as a colorless glassy solid. HPLC retention time=1.50 minutes (YMC Combi 4.6×30 mm S-5 ODS column) eluting with 10-90% aqueous methanol+0.1 TFA a 2 minute gradient. MS: (M+H)=516.27.

14. 1-(4-(5-(4-(Methylcarbamoyl)-3-phenylisoxazol-5-yl)-1,2,4-oxadiazol-3-yl)benzyl)azetidine-3-carboxylic acid, 2,2,2-trifluoroacetic acid salt A solution of tert-butyl 1-(4-(5-(4-(methylcarbamoyl)-3-phenylisoxazol-5-yl)-1,2,4-oxadiazol-3-yl)benzyl)azetidine-3-carboxylate (28 mg, 0.054 mmol) in TFA (1 mL) was allowed to stand at rt for 1.5 hr. The volatiles were removed in vacuo and the residue was co-evaporated from EtOAc/Hex (2×2 mL). The residue was triturated with ethyl ether and dried to afford partially purified material. The residue was subjected to preparative HPLC (Shimadzu 20×100 mm S-10 column; eluting with 0-90% aqueous methanol+0.1% TFA over a 10 minute gradient). The essentially pure fractions containing product were concentrated to afford 1-(4-(5-(4-(methylcarbamoyl)-3-phenylisoxazol-5-yl)-1,2,4-oxadiazol-3-yl)benzyl)azetidine-3-carboxylic acid, 2,2,2-trifluoroacetic acid salt (24 mg, 0.042 mmol, 77% yield) as a white solid. HPLC retention time=2.22 minutes (YMC Combi 4.6×50 mm S-5 ODS column) eluting with 10-90% aqueous methanol+0.2% phosphoric acid over a 4 minute gradient. MS: (M+H)=460.18. $^1$H NMR (400 MHz, MeOD) d ppm 2.99 (d, J=4.52 Hz, 3H) 3.68-3.79 (m, 1H) 4.33-4.44 (m, 4H) 4.53 (s, 2H) 7.50-7.60 (m, 3H) 7.69 (d, J=8.0 Hz, 2H) 7.82 (dd, J=7.7, 1.6 Hz, 2H) 8.26 (d, J=8.3 Hz, 2H) 8.98 (d, J=4.52 Hz, 1H).

Example 15

1-(4-(5-(3-Phenyl-4-(2,2,2-trifluoroethylcarbamoyl)isoxazol-5-yl)-1,2,4-oxadiazol-3-yl)benzyl)azetidine-3-carboxylic acid, 2,2,2-trifluoroacetic acid salt

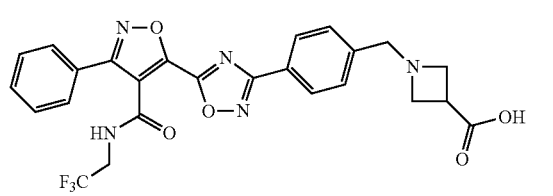

(15)

15-A. 5-(3-(4-((3-(tert-Butoxycarbonyl)azetidin-1-yl)methyl)phenyl)-1,2,4-oxadiazol-5-yl)-3-phenyl-isoxazole-4-carboxylic acid, lithium salt

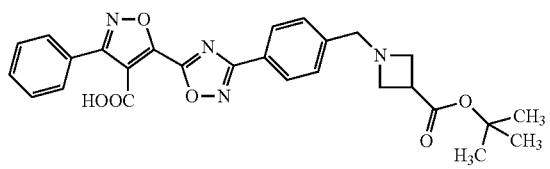

(15-A)

To a mixture of methyl 5-(3-(4-((3-(tert-butoxycarbonyl)azetidin-1-yl)methyl)phenyl)-1,2,4-oxadiazol-5-yl)-3-phenylisoxazole-4-carboxylate, 13-D, (567 mg, 1.098 mmol) in THF (8 mL) and water (2 mL) at rt was added LiOH, hydrate (46.1 mg, 1.098 mmol) and the reaction mixture was allowed to stir at rt for 18 hr. An additional 11 mg of LiOH, hydrate was added and stirring was continued at rt for 24 hr. The volatiles were removed in vacuo and the residue was co-evaporated from EtOAc/Heptane (3×5 mL) and dried to afford as a 5-(3-(4-((3-(tert-butoxycarbonyl)azetidin-1-yl)methyl)phenyl)-1,2,4-oxadiazol-5-yl)-3-phenylisoxazole-4-carboxylic acid, lithium salt (555 mg, 1.089 mmol, 99% yield) foamy yellow solid. The material was used as is in the subsequent step. HPLC retention time=1.69 minutes (YMC Combi 4.6×30 mm S-5 ODS column) eluting with 10-90% aqueous methanol+0.1 TFA a 2 minute gradient. MS: (M+H)=503.06.

15-B. tert-Butyl 1-(4-(5-(3-phenyl-4-(2,2,2-trifluoroethylcarbamoyl)isoxazol-5-yl)-1,2,4-oxadiazol-3-yl)benzyl)azetidine-3-carboxylate

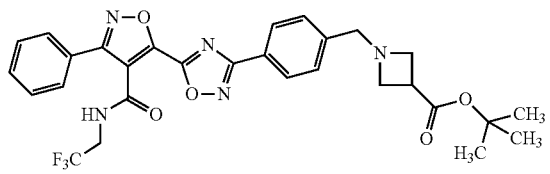

(15-B)

A mixture of 5-(3-(4-((3-(tert-butoxycarbonyl)azetidin-1-yl)methyl)phenyl)-1,2,4-oxadiazol-5-yl)-3-phenylisoxazole-4-carboxylic acid (30 mg, 0.060 mmol), 2,2,2-trifluoroethylamine (7.15 μL, 0.090 mmol), BOP-Cl (18.24 mg, 0.072 mmol) and Et₃N (0.025 mL, 0.179 mmol) in DMF (0.5 mL) was stirred at rt over the weekend. The reaction mixture was partitioned between EtOAc (30 mL) and saturated sodium bicarbonate solution (30 mL). The organic layer was washed with water (2×30 mL) and brine (30 mL). After drying (MgSO₄) and filtration, the organic layer was concentrated to a colorless solid that was chromatographed on a 4 gm Isco silica gel cartridge, eluting with a 0-70% EtOAc/Hex gradient. The essentially pure fractions containing product were concentrated to afford tert-butyl 1-(4-(5-(3-phenyl-4-(2,2,2-trifluoroethylcarbamoyl)isoxazol-5-yl)-1,2,4-oxadiazol-3-yl)benzyl)azetidine-3-carboxylate (18 mg, 0.031 mmol, 51.7% yield) as a white solid. This material was deemed suitable to use in the next step without further purification. HPLC retention time=1.71 minutes (YMC Combi 4.6×30 mm S-5 ODS column) eluting with 10-90% aqueous methanol+0.1 TFA a 2 minute gradient. MS: (M+H)=584.10.

15. Preparation of 1-(4-(5-(3-phenyl-4-(2,2,2-trifluoroethylcarbamoyl)isoxazol-5-yl)-1,2,4-oxadiazol-3-yl)benzyl)azetidine-3-carboxylic acid, 2,2,2-trifluoroacetic acid salt A solution of tert-butyl 1-(4-(5-(3-phenyl-4-(2,2,2-trifluoroethylcarbamoyl) isoxazol-5-yl)-1,2,4-oxadiazol-3-yl)benzyl)azetidine-3-carboxylate (17 mg, 0.029 mmol) in TFA was allowed to stand at rt for 1.5 hr. After concentration, the residue was subjected to preparative HPLC (Shimadzu 20×100 mm S-10 column; eluting with 30-90% aqueous methanol+0.1% TFA over a 10 minute gradient). The essentially pure fractions containing product were concentrated to afford 1-(4-(5-(3-phenyl-4-(2,2,2-trifluoroethylcarbamoyl)isoxazol-5-yl)-1,2,4-oxadiazol-3-yl)benzyl)azetidine-3-carboxylic acid, 2,2,2-trifluoroacetic acid salt (14 mg, 0.022 mmol, 74.9% yield) as a colorless glassy solid. HPLC retention time=2.56 minutes (YMC Combi 4.6×50 mm S-5 ODS column) eluting with 10-90% aqueous methanol+0.2% phosphoric acid over a 4 minute gradient.

MS: (M+H)=528.00. ¹H NMR (400 MHz, MeOD) δ ppm 3.68-3.79 (m, 1H) 4.18 (q, J=9.3 Hz, 2H) 4.33-4.43 (m, 4H) 4.52 (s, 2H) 7.50-7.59 (m, 3H) 7.68 (d, J=8.0 Hz, 2H) 7.77-7.86 (m, 2H) 8.27 (d, J=8.3 Hz, 2H).

Example 16

5-(3-(4-((3-Carboxyazetidin-1-yl)methyl)phenyl)-1,2,4-oxadiazol-5-yl)-3-phenylisoxazole-4-carboxylic acid

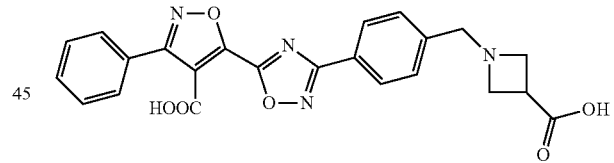

(16)

A solution of 5-(3-(4-((3-(tert-butoxycarbonyl)azetidin-1-yl)methyl)phenyl)-1,2,4-oxadiazol-5-yl)-3-phenylisoxazole-4-carboxylic acid, lithium salt, 15-A, (25 mg, 0.049 mmol) in TFA (0.5 mL) was allowed to stand at rt for 1 hr. The volatiles were removed in vacuo and the residue was suspended in water (1 ml). The pH was adjusted to ~10 with 1N NaOH, resulting in a homogeneous solution. The pH was then adjusted to ~4 with 1N HCl. The resulting suspension was allowed to stir at rt for 1.5 hr. Slow filtration, washing the filter cake with water and drying afforded 17 mg of a white solid. The solid was suspended in MeOH (2 ml) and was stirred briskly at rt for 4 hr. Filtration and drying afford 5-(3-(4-((3-carboxyazetidin-1-yl)methyl)phenyl)-1,2,4-oxadiazol-5-yl)-3-phenylisoxazole-4-carboxylic acid (15 mg, 0.034 mmol, 68.5% yield) as a white solid. HPLC retention time=2.43 minutes (YMC Combi 4.6×50 mm S-5 ODS column) eluting with 10-90% aqueous methanol+0.2% phosphoric acid over a 4 minute gradient. MS: (M+H)=447.15. ¹H NMR (400 MHz, DMSO-d$_6$) δ ppm 3.83 (s, 2H) 3.92 (s, 2H) 4.15 (s, 2H) 7.52-7.58 (m, 3H) 7.61 (d, J=8.0 Hz, 2H) 7.89-7.96 (m, 2H) 8.04 (d, J=8.0 Hz, 2H).

Example 17

Preparation of 1-(4-(5-(4,5-diphenylisoxazol-3-yl)-1,2,4-oxadiazol-3-yl)benzyl)azetidine-3-carboxylic acid, 2,2,2-trifluoroacetic acid salt

(17)

17-A. Methyl 4,5-diphenylisoxazole-3-carboxylate

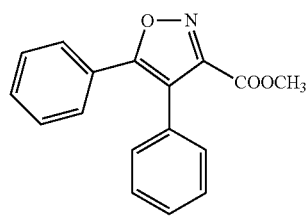

(17-A)

A mixture of 1,2-diphenylethyne (1.53 g, 8.6 mmol) and dimethyl 2-nitromalonate (1.05 mL, 7.83 mmol) in mesitylene (11 ml) was heated to 150° C. for 18 hr. The volatiles were removed in vacuo and the residue was chromatographed on a 5×12 cm silica gel column eluting with 0-10% EtOAc/hexanes. The essentially pure fractions containing product were concentrated to afford methyl 4,5-diphenylisoxazole-3-carboxylate (307 mg, 1.1 mmol, 14.04% yield) as a light yellow solid. HPLC retention time=1.85 minutes (YMC Combi 4.6×30 mm S-5 ODS column) eluting with 10-90% aqueous methanol+0.1 TFA a 2 minute gradient.

MS: (M+H)=280.08. $^1$H NMR (400 MHz, chloroform-d) δ ppm 3.87 (s, 3H) 7.29-7.40 (m, 5H) 7.43 (m, 3H) 7.47-7.53 (m, 2H).

17-B. 4,5-Diphenylisoxazole-3-carboxylic acid

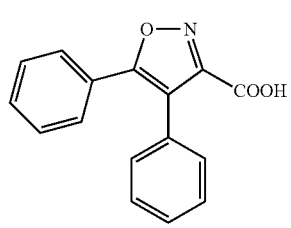

(17-B)

To a thick suspension of methyl 4,5-diphenylisoxazole-3-carboxylate (306 mg, 1.09 mmol) in MeOH (8 mL), THF (2 mL) and water (2 mL) at rt was added LiOH, hydrate (46.0 mg, 1.09 mmol) and the reaction mixture was allowed to stir at rt for 1 hr. During this time, the reaction became homogeneous. The MeOH and THF were removed in vacuo and the remaining aqueous mixture was acidified to pH ~1 with 1N HCl. The mixture was then extracted with EtOAc (30 mL). The organic layer was washed with brine (20 mL), dried (MgSO$_4$) and concentrated to afford 4,5-diphenylisoxazole-3-carboxylic acid (290 mg, 1.09 mmol, 100% yield) as a yellow solid. HPLC retention time=1.72 minutes (YMC Combi 4.6×30 mm S-5 ODS column) eluting with 10-90% aqueous methanol+0.1 TFA a 2 minute gradient.

MS: (M+H)=266.08.

17-C. tert-Butyl 1-(4-(5-(4,5-diphenylisoxazol-3-yl)-1,2,4-oxadiazol-3-yl)benzyl)azetidine-3-carboxylate

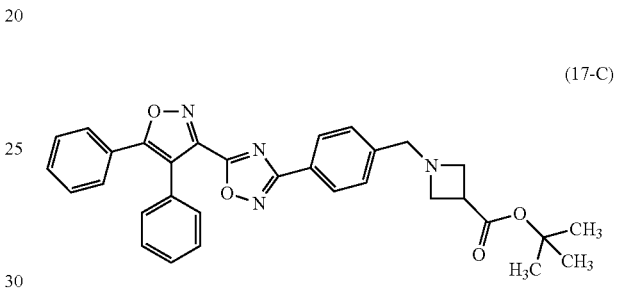

(17-C)

A mixture of 4,5-diphenylisoxazole-3-carboxylic acid (26.5 mg, 0.1 mmol), (Z)-tert-butyl 1-(4-(N'-hydroxycarbamimidoyl)benzyl)azetidine-3-carboxylate, Int.1, (30.5 mg, 0.100 mmol), HOBT (16.85 mg, 0.110 mmol) and EDC (21.09 mg, 0.110 mmol) in DMF (1 mL) was stirred at rt for 18 hr. The reaction mixture was warmed to 60° C. for 2 hr and 70° C. for 2 hr. After cooling to rt overnight, the reaction mixture was partitioned between EtOAc (30 ml) and saturated sodium bicarbonate solution (30 ml). The organic layer was washed with water (2×30 ml) and brine (20 ml). After drying (MgSO$_4$) and filtration, the organic layer was concentrated to a yellow solid that was chromatographed on a 4 gm Isco silica gel cartridge, eluting with a 0-60% EtOAc/Hex gradient. The pure fractions were concentrated to afford tert-butyl 1-(4-(5-(4,5-diphenylisoxazol-3-yl)-1,2,4-oxadiazol-3-yl)benzyl)azetidine-3-carboxylate (37 mg, 0.069 mmol, 69.2% yield) as a white solid. HPLC retention time=1.90 minutes (YMC Combi 4.6×30 mm S-5 ODS column) eluting with 10-90% aqueous methanol+0.1 TFA a 2 minute gradient.

MS: (M+H)=535.16.

Example 17. 1-(4-(5-(4,5-Diphenylisoxazol-3-yl)-1,2,4-oxadiazol-3-yl)benzyl)azetidine-3-carboxylic acid, 2,2,2-trifluoroacetic acid salt A solution of tert-butyl 1-(4-(5-(4,5-diphenylisoxazol-3-yl)-1,2,4-oxadiazol-3-yl)benzyl)azetidine-3-carboxylate (37 mg, 0.069 mmol) in TFA (1 mL) was allowed to stand at rt for 1 hr. At this time, the volatiles were removed in vacuo and the residue was subjected to preparative HPLC (Shimadzu 20×100 mm 5-10 column; eluting with 50-90% aqueous methanol+0.1% TFA over a 8 minute gradient). The essentially pure fractions containing product were concentrated to afford 1-(4-(5-(4,5-diphenylisoxazol-3-yl)-1,2,4-oxadiazol-3-yl)benzyl)azetidine-3-carboxylic acid, 2,2,2-trifluoroacetic acid salt (31 mg, 0.052 mmol, 76% yield) as a white Examples 18 and 19

1-(4-(5-(5-Isobutyl-4-propylisoxazol-3-yl)-1,2,4-oxadiazol-3-yl)benzyl)azetidine-3-carboxylic acid, (18), and 1-(4-(5-(4-Isobutyl-5-propylisoxazol-3-yl)-1,2,4-oxadiazol-3-yl)benzyl)azetidine-3-carboxylic acid, (19)

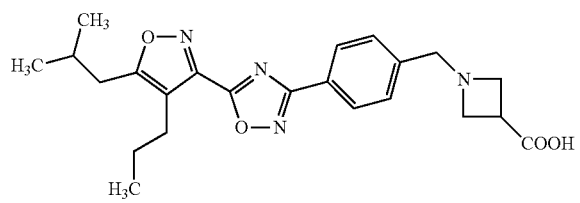
(18)

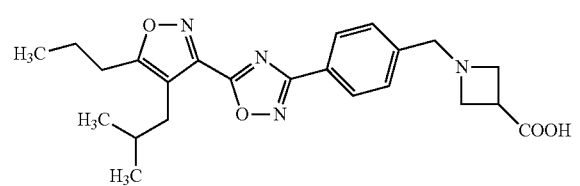
(19)

18-A. 2-Methyloct-4-yne

(18-A)

To a solution of 4-methylpent-1-yne (0.588 mL, 5 mmol) in THF at −78° C. was added BuLi, 2.5 M in hexanes (2.200 mL, 5.50 mmol). After stirring 15 minutes at −78° C., the reaction mixture was allowed to warm to room temperature, 1-iodopropane (0.488 mL, 5.00 mmol) was added and the reaction mixture was stirred at rt for 3 days. The reaction mixture was quenched with water (50 mL) and the resulting mixture was transferred to a separatory funnel. The mixture was extracted with ether (75 mL). The organic layer was washed with brine (50 mL), dried (MgSO$_4$) and concentrated to afford 2-methyloct-4-yne (555 mg, 4.47 mmol, 89% yield) as a light yellow liquid. $^1$H NMR (400 MHz, chloroform-d) δ ppm 0.91-0.99 (m, 9H) 1.45-1.53 (m, 2H) 1.70-1.81 (m, 1H) 2.03 (dt, J=6.5, 2.4 Hz, 2H) 2.12 (tt, J=7.0, 2.4 Hz, 2H).

18-B. Methyl 5-isobutyl-4-propylisoxazole-3-carboxylate and methyl 4-isobutyl-5-propylisoxazole-3-carboxylate

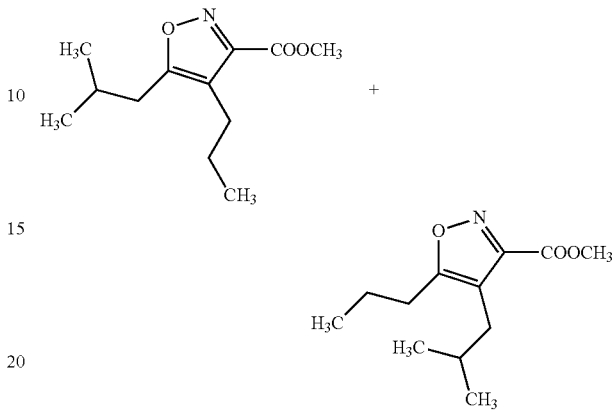

A mixture of 6-methylhept-3-yne (220 mg, 2 mmol), dimethyl 2-nitromalonate (567 mg, 3.20 mmol) and 1-butyl-3-methylimidazolium hexafluorophosphate (0.04 ml, 0.2 mmol) in toluene (4 mL) was heated to 170° C. in the microwave for 1 hr. After cooling to rt, the reaction mixture was partitioned between EtOAc (50 ml) and water (50 ml). The organic layer was washed with brine, dried (MgSO$_4$) and concentrated to afford an orange oil that was chromatographed on a 12 gm Isco silica gel cartridge, eluting with a 0-5% EtOAc/Hex gradient. The fractions which contained product were concentrated to afford 228 mg, 54. % yield of a mixture of methyl 4-ethyl-5-isobutylisoxazole-3-carboxylate and methyl 5-ethyl-4-isobutylisoxazole-3-carboxylate as light yellow oil. HPLC retention time=1.86 minutes (YMC Combi 4.6×30 mm S-5 ODS column) eluting with 10-90% aqueous methanol+0.1 TFA a 2 minute gradient. MS: (M+H)=226.22. $^1$H NMR indicates a ~1:1 mixture of regioisomers. These isomers were not readily separable by normal or reverse phase chromatography and this material was used without further purification in the next step.

18.C 5-Isobutyl-4-propylisoxazole-3-carboxylic acid and 4-isobutyl-5-propylisoxazole-3-carboxylic acid

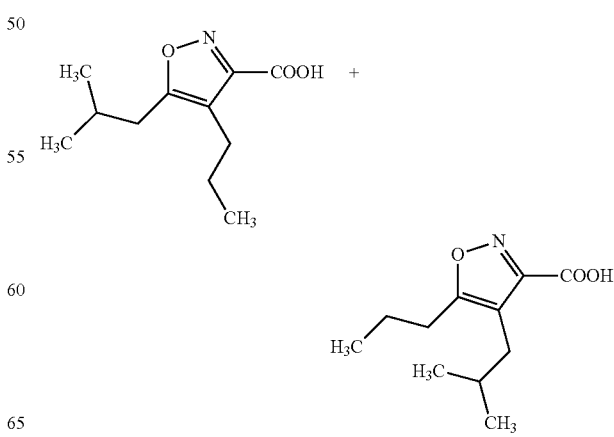

To a mixture of methyl 5-isobutyl-4-propylisoxazole-3-carboxylate and methyl 4-isobutyl-5-propylisoxazole-3-carboxylate (164 mg, 0.728 mmol) in MeOH (8 mL) and water (2 mL) was added LiOH, hydrate (15.28 mg, 0.364 mmol) and the mixture was allowed to stir overnight at rt. An additional amount of LiOH, hydrate (15.28 mg, 0.364 mmol) was added and the reaction mixture was stirred at rt for 2 hr. The MeOH was removed in vacuo and the remaining aqueous was acidified to pH ~1 with 1N HCl. The mixture was extracted with EtOAc (20 mL). The organic layer was washed with brine (20 mL), dried (MgSO$_4$) and concentrated to afford (144 mg, 0.682 mmol, 94% yield) of product which was approximately a 1:1 mixture of 5-isobutyl-4-propylisoxazole-3-carboxylic acid and 4-isobutyl-5-propylisoxazole-3-carboxylic acid as a light yellow oil. HPLC retention time=1.72 minutes (YMC Combi 4.6×30 mm S-5 ODS column) eluting with 10-90% aqueous methanol+0.1 TFA a 2 minute gradient. MS: (M+H)=212.20.

$^1$H NMR indicates a ~1:1 mixture of regioisomers as shown in the schematic above. These isomers were not readily separable by normal or reverse phase chromatography and this material was used without further purification in the next step.

18-D. tert-Butyl 1-(4-(5-(5-isobutyl-4-propylisoxazol-3-yl)-1,2,4-oxadiazol-3-yl)benzyl)azetidine-3-carboxylate and tert-Butyl 1-(4-(5-(4-isobutyl-5-propylisoxazol-3-yl)-1,2,4-oxadiazol-3-yl)benzyl)azetidine-3-carboxylate

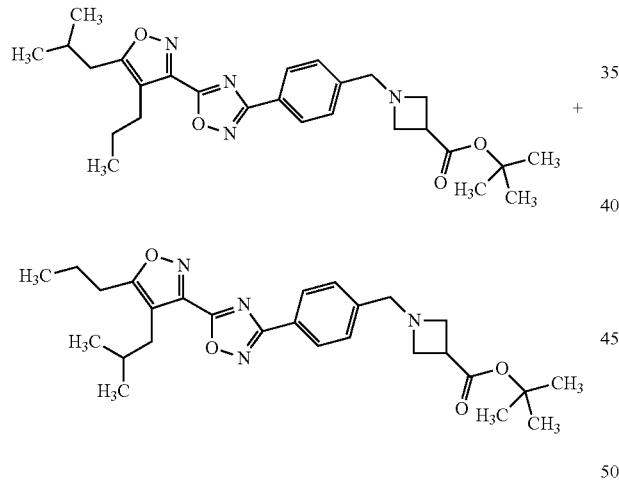

A mixture of 5-isobutyl-4-propylisoxazole-3-carboxylic acid, and 4-isobutyl-5-propylisoxazole-3-carboxylic acid (42.26 mg, 0.2 mmol), (Z)-tert-butyl 1-(4-(N'-hydroxycarbamimidoyl)benzyl)azetidine-3-carboxylate (61.1 mg, 0.200 mmol), HOBt (38.3 mg, 0.250 mmol), diisopropylethylamine (0.070 mL, 0.400 mmol) and EDC (47.9 mg, 0.250 mmol) in DMF (1 mL) was stirred at rt for 18 hr. DMF (1 mL) was added and the reaction mixture was warmed to 50° C. for 8 hr. The reaction mixture was partitioned between EtOAc (30 ml) and saturated sodium bicarbonate solution (30 ml). The organic layer was washed with water (2×30 ml) and brine (30 ml). After drying (MgSO$_4$) and filtration, the organic layer was concentrated to afford an oil that was chromatographed on a 4 gm Isco silica gel cartridge, eluting with a 0-100% EtOAc/Hex gradient. The pure fractions were concentrated to afford a mixture of tert-butyl 1-(4-(5-(5-isobutyl-4-propylisoxazol-3-yl)-1,2,4-oxadiazol-3-yl)benzyl)azetidine-3-carboxylate (32 mg, 0.067 mmol, 66.6% yield) and tert-butyl 1-(4-(5-(4-isobutyl-5-propylisoxazol-3-yl)-1,2,4-oxadiazol-3-yl)benzyl)azetidine-3-carboxylate (32 mg, 0.067 mmol, 66.6% yield) as a colorless oil. HPLC retention time=1.89 minutes (YMC Combi 4.6×30 mm S-5 ODS column) eluting with 10-90% aqueous methanol+0.1 TFA a 2 minute gradient.

MS: (M+H)=481.32.

The mixture was separated on a Berger Prep SFC MGIII Unit on a Chiral AD-H 30×3 cm ID, 5 µm column, eluting with 70/30 CO$_2$/(MeOH, 0.1% diethylamine) and a flow rate of 88 mL/min, monitored at 220 nm. The fractions from the first peak to elute were concentrated to afford tert-butyl 1-(4-(5-(4-isobutyl-5-propylisoxazol-3-yl)-1,2,4-oxadiazol-3-yl)benzyl)azetidine-3-carboxylate (21 mg; 44%) as a colorless oil. $^1$H NMR (500 MHz, CDCl$_3$) δ ppm 0.93 (d, J=7.3 Hz, 6H) 1.00 (t, J=7.4 Hz, 3H) 1.44 (s, 9H) 1.79 (m, 2H) 1.92 (m, 1H) 2.62 (d, J=6.7 Hz, 2H) 2.77 (t, J=7.4 Hz, 2H) 3.27 (m, 3H) 3.53 (m, 2H) 3.66 (s, 2H) 7.42 (d, J=8.1 Hz, 2H) 8.10 (d, J=8.1 Hz, 2H).

The fractions from the second peak to elute were concentrated to afford tert-butyl 1-(4-(5-(5-isobutyl-4-propylisoxazol-3-yl)-1,2,4-oxadiazol-3-yl)benzyl)azetidine-3-carboxylate (24 mg; 50%) as a colorless oil. $^1$H NMR (500 MHz, CDCl$_3$) δ ppm 0.95-1.01 (m, 9H) 1.44 (s, 9H) 1.57-1.65 (m, 2H) 2.10-2.19 (m, 1H) 2.67 (d, J=7.4 Hz, 2H) 2.69-2.73 (m, 2H) 3.22-3.30 (m, 3H) 3.50-3.56 (m, 2H) 3.67 (s, 2H) 7.42 (d, J=8.1 Hz, 2H) 8.10 (d, J=8.1 Hz, 2H).

Example 18

1-(4-(5-(5-Isobutyl-4-propylisoxazol-3-yl)-1,2,4-oxadiazol-3-yl)benzyl)azetidine-3-carboxylic acid, TFA

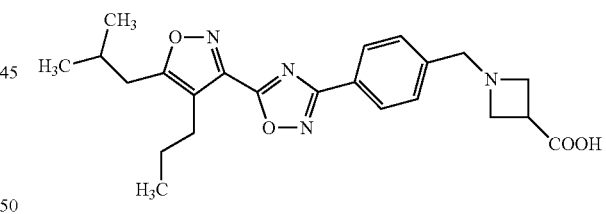

(18)

A solution of tert-butyl 1-(4-(5-(5-isobutyl-4-propylisoxazol-3-yl)-1,2,4-oxadiazol-3-yl)benzyl)azetidine-3-carboxylate (23 mg, 0.048 mmol) in TFA (0.5 mL) was allowed to stand at rt for 2.5 hr. The volatiles were removed in vacuo and the residue was triturated with Et$_2$O and dried to afford 1-(4-(5-(5-isobutyl-4-propylisoxazol-3-yl)-1,2,4-oxadiazol-3-yl)benzyl)azetidine-3-carboxylic acid, TFA (24 mg, 0.044 mmol, 92% yield) as a light yellow glassy solid. HPLC retention time=3.21 minutes (YMC Combi 4.6×50 mm S-5 ODS column) eluting with 10-90% aqueous methanol+0.2% phosphoric acid over a 4 minute gradient. MS: (M+H)=425.20. $^1$H NMR (400 MHz, MeOD) δ ppm 1.01 (m, 9H) 1.60-1.71 (m, 2H) 2.14 (m, 1H) 2.77 (m, 4H) 3.62-3.73 (m, 1H) 4.30-4.40 (m, 4H) 4.51 (s, 2H) 7.68 (d, J=7.8 Hz, 2H) 8.24 (d, J=7.8 Hz, 2H).

Example 19

1-(4-(5-(4-Isobutyl-5-propylisoxazol-3-yl)-1,2,4-oxadiazol-3-yl)benzyl)azetidine-3-carboxylic acid, TFA

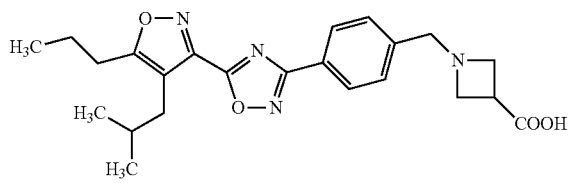
(19)

A solution of tert-butyl 1-(4-(5-(4-isobutyl-5-propylisoxazol-3-yl)-1,2,4-oxadiazol-3-yl)benzyl)azetidine-3-carboxylate (21 mg, 0.044 mmol) in TFA (0.5 mL) was allowed to stand at rt for 2.5 hr. The volatiles were removed in vacuo and the residue was triturated with Et$_2$O and dried to afford 1-(4-(5-(4-isobutyl-5-propylisoxazol-3-yl)-1,2,4-oxadiazol-3-yl)benzyl)azetidine-3-carboxylic acid, TFA (21 mg, 0.038 mmol, 88% yield) as a light yellow glassy solid. HPLC retention time=3.20 minutes (YMC Combi 4.6×50 mm S-5 ODS column) eluting with 10-90% aqueous methanol+0.2% phosphoric acid over a 4 minute gradient. MS: (M+H)=425.20. $^1$H NMR (400 MHz, MeOD) δ ppm 0.96 (d, J=6.5 Hz, 6H) 1.03 (t, J=7.3 Hz, 3H) 1.75-1.86 (m, 2H) 1.94 (m, 1H) 2.68 (d, J=7.3 Hz, 2H) 2.85 (t, J=7.5 Hz, 2H) 3.61-3.71 (m, 1H) 4.29-4.40 (m, 4H) 4.50 (s, 2H) 7.68 (d, J=8.0 Hz, 2H) 8.24 (d, J=8.3 Hz, 2H).

Example 20

1-(4-(5-(5-Isobutyl-4-(trifluoromethyl)isoxazol-3-yl)-1,2,4-oxadiazol-3-yl)benzyl)-azetidine-3-carboxylic acid

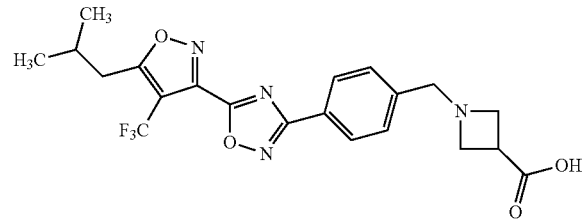
(20)

20-A. Methyl 4-Iodo-5-isobutylisoxazole-3-carboxylate

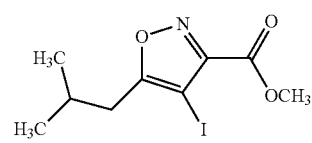
(20-A)

A mixture of methyl 5-isobutylisoxazole-3-carboxylate (0.923 g, 5.04 mmol) and N-iodosuccinimide (1.25 g, 5.54 mmol) in trifluoroacetic acid (25 mL) was stirred at room temperature overnight. By HPLC, the reaction was complete. The trifluoroacetic acid was removed under reduced pressure, and the residue was diluted with dichloromethane (100 mL), washed with a saturated aqueous solution of sodium bicarbonate (2×25 mL), washed with a 2.5% aqueous solution of sodium bisulfate (25 mL), and dried over anhydrous sodium sulfate. Concentration under reduced pressure followed by purification by flash silica gel chromatography using a 5% mixture of ethyl acetate in hexane afforded methyl 4-iodo-5-isobutylisoxazole-3-carboxylate (1.21 g, 3.91 mmol, 78% yield) as a pale yellow oil. The product had an HPLC ret. time=2.40 min.–Column: CHROMOLITH® SpeedROD 4.6×50 mm (4 min.); Solvent A=10% MeOH, 90% H$_2$O, 0.1% TFA; Solvent B=90% MeOH, 10% H$_2$O, 0.1% TFA. LC/MS M+1=310.1.

20-B. Methyl 5-isobutyl-4-(trifluoromethyl)isoxazole-3-carboxylate

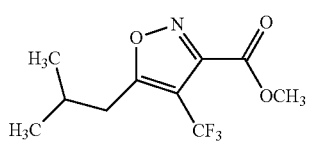
(20-B)

To a solution of methyl 4-iodo-5-isobutylisoxazole-3-carboxylate (1.21 g, 3.91 mmol), copper(I) iodide (0.149 g, 0.783 mmol), and HMPA (2.59 mL) in N,N-dimethylformamide (19 mL) was added methyl 2,2-difluoro-2-(fluorosulfonyl)acetate (1.99 mL, 15.7 mmol) over 1 min. The reaction mixture was immediately immersed in an oil bath at 75° C. and was stirred overnight. The clear, orange reaction mixture was cooled to room temperature and diluted with ether (100 mL), washed with a saturated aqueous solution of ammonium chloride (2×100 mL), washed with a 10% aqueous solution of lithium chloride (2×50 mL), and washed with brine (50 mL). The aqueous layer was back-extracted with ether (100 mL+50 mL), and the combined organic layers were dried over anhydrous sodium sulfate. Concentration under reduced pressure followed by purification by flash silica gel chromatography using a 5% mixture of ethyl acetate in hexane provided methyl 5-isobutyl-4-(trifluoromethyl)isoxazole-3-carboxylate (0.819 g, 3.26 mmol, 83% yield) as a clear, colorless oil. The product had an HPLC ret. time=2.52 min.–Column. CHROMOLITH® SpeedROD 4.6×50 mm (4 min.); Solvent A=10% MeOH, 90% H$_2$O, 0.1% TFA; Solvent B=90% MeOH, 10% H$_2$O, 0.1% TFA. $^1$H NMR (500 MHz, CDCl$_3$) δ ppm 0.99 (s, 3H), 1.00 (s, 3H), 2.09-2.20 (m, 1H), 2.86 (dd, J=7.21, 1.11 Hz, 2H), and 4.01 (s, 3H).

20-C. 5-Isobutyl-4-(trifluoromethyl)isoxazole-3-carboxylic acid

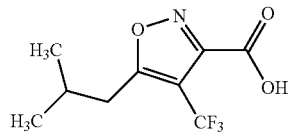
(20-C)

A mixture of methyl 5-isobutyl-4-(trifluoromethyl)isoxazole-3-carboxylate (0.816 g, 3.25 mmol) and lithium hydroxide hydrate (0.136 g, 3.25 mmol) in methanol (18 mL)

and water (9.00 mL) was stirred at room temperature overnight. HPLC and LCMS analysis indicated that the hydrolysis was complete. The reaction mixture was concentrated under reduced pressure, and the residue dissolved in 1N aqueous hydrochloric acid and extracted with ether. The organic layer was collected and dried over anhydrous sodium sulfate. Concentration under reduced pressure afforded 5-isobutyl-4-(trifluoromethyl)isoxazole-3-carboxylic acid (0.746 g, 3.15 mmol, 97% yield) as an off-white solid. The product had an HPLC ret. time=2.00 min.–Column. CHROMOLITH® SpeedROD 4.6×50 mm (4 min.); Solvent A=10% MeOH, 90% $H_2O$, 0.1% TFA; Solvent B=90% MeOH, 10% $H_2O$, 0.1% TFA. $^1$H NMR (400 MHz, DMSO-$d_6$) δ ppm 0.91 (s, 3H), 0.93 (s, 3H), 1.97-2.09 (m, 1H), and 2.89 (d, J=7.28 Hz, 2H).

20-D. 3-Isobutyl-4-(trifluoromethyl)isoxazole-5-carbonyl fluoride

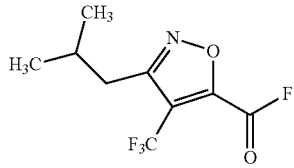

(20-D)

To a mixture of 3-isobutyl-4-(trifluoromethyl)isoxazole-5-carboxylic acid (0.200 g, 0.843 mmol) and pyridine (0.082 mL, 1.01 mmol) in dichloromethane (8 mL) at room temperature was added 2,4,6-trifluoro-1,3,5-triazine (cyanuric fluoride) (0.085 mL, 1.01 mmol). The reaction mixture was stirred at room temperature overnight. The heterogeneous reaction was diluted with dichloromethane, washed with an ice-cold solution of 0.5N aqueous hydrochloric acid (2×), and the organic layer was collected. The aqueous layer was back-extracted with dichloromethane, and the combined organic layers were dried anhydrous sodium sulfate and concentrated to afford 3-isobutyl-4-(trifluoromethyl)isoxazole-5-carbonyl fluoride (0.130 g, 0.544 mmol, 65% yield) as a yellow solid. The product had an HPLC ret. time=2.51 min. (corresponding to the methyl ester)–Column: CHROMOLITH® SpeedROD 4.6×50 mm (4 min.); Solvent A=10% MeOH, 90% $H_2O$, 0.1% TFA; Solvent B=90% MeOH, 10% $H_2O$, 0.1% TFA.

20-E. tert-Butyl 1-(4-(5-(5-isobutyl-4-(trifluoromethyl)isoxazol-3-yl)-1,2,4-oxadiazol-3-yl)benzyl)azetidine-3-carboxylate

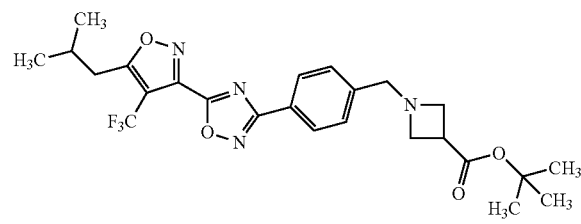

(20-E)

A mixture of 5-isobutyl-4-(trifluoromethyl)isoxazole-3-carbonyl fluoride (0.130 g, 0.544 mmol), tert-butyl 1-(4-(N'-hydroxycarbamimidoyl)benzyl)azetidine-3-carboxylate (Int.1, 0.166 g, 0.544 mmol), and Hunig's Base (0.123 mL, 0.707 mmol) in acetonitrile (2 mL) was stirred at room temperature for 2 days. By HPLC, there was ~7% of the uncyclized intermediate remaining The reaction mixture was gently heated with a heat gun for ~15 min., resulting in further cyclization. The homogenous mixture was diluted with dichloromethane and washed with a saturated aqueous solution of sodium bicarbonate. The aqueous layer was extracted with dichloromethane, and the organic layers were combined and dried over anhydrous sodium sulfate. Concentration under reduced pressure followed by purification by flash silica gel chromatography using a 1% mixture of methanol in dichloromethane afforded tert-butyl 1-(4-(5-(5-isobutyl-4-(trifluoromethyl)isoxazol-3-yl)-1,2,4-oxadiazol-3-yl)benzyl)azetidine-3-carboxylate (0.219 g, 0.432 mmol, 80% yield) as a clear, viscous yellow oil. The product had an HPLC ret. time=3.03 min.–Column. CHROMOLITH® SpeedROD 4.6×50 mm (4 min.); Solvent A=10% MeOH, 90% $H_2O$, 0.1% TFA; Solvent B=90% MeOH, 10% $H_2O$, 0.1% TFA. MS $M^{+1}$=507.4.

20. 1-(4-(5-(5-Isobutyl-4-(trifluoromethyl)isoxazol-3-yl)-1,2,4-oxadiazol-3-yl)benzyl)-azetidine-3-carboxylic acid A mixture of tert-butyl 1-(4-(5-(5-isobutyl-4-(trifluoromethyl)isoxazol-3-yl)-1,2,4-oxadiazol-3-yl)benzyl)azetidine-3-carboxylate (0.219 g, 0.432 mmol) and trifluoroacetic acid (2.50 mL, 32.4 mmol) was stirred at room temperature for 45 min. The trifluoroacetic acid was removed under reduced pressure, and the residue was suspended in ~6 mL of water with sonication. The product gummed up and did not disperse. The pH was adjusted to ~4.5 with 1N aqueous sodium hydroxide, and the product still remained largely clumped on the bottom. Dichloromethane (~8 mL) was added, and the mixture was stirred vigorously overnight. The organic layer was collected, dried over anhydrous sodium sulfate, and concentrated. The oily residue was dissolved in methanol and left standing overnight. The methanol solution was passed through a Whatman 0.45 um PTFE w/GMF syringe filter and concentrated to give the product (0.195 g, 0.424 mmol, 98% yield) as a pale, yellow oil.

A portion of the compound was purified by flash silica gel chromatography using a mixture of methanol, dichloromethane, and ammonium hydroxide (10:90:0-20:80:1). The desired fractions were concentrated, diluted with dichloromethane and water, and the pH was adjusted to 4.5 with 1.0 N aqueous hydrochloric acid. After shaking, the resulting emulsion was left to settle for 30 min. The organic layer was collected, and the aqueous layer/emulsion was back-extracted with dichloromethane (2×). The cloudy organic layer was dried over anhydrous sodium sulfate and concentrated to give a white solid residue which was redissolved in dichloromethane and filtered through a Whatman 0.45 um PTFE w/GMF syringe filter and concentrated to give the product as a white solid (118 mg). The solid was suspended in methanol with sonication and concentrated (2×). After the third resuspension, the solid was collected by vacuum filtration to give 1-(4-(5-(5-isobutyl-4-(trifluoromethyl)isoxazol-3-yl)-1,2,4-oxadiazol-3-yl)benzyl)azetidine-3-carboxylic acid (0.011 g, 0.024 mmol, 5.6% yield) as a white solid. The compound had an HPLC ret. time=2.68 min.–Column. CHROMOLITH® SpeedROD 4.6×50 mm (4 min.); Solvent A=10% MeOH, 90% $H_2O$, 0.1% TFA; Solvent B=90% MeOH, 10% $H_2O$, 0.1% TFA. MS M$^{+1}$=451.1. $^1$H NMR (500 MHz, CDCl$_3$) δ ppm 1.02 (s, 3H), 1.03 (s, 3H), 2.15-2.25 (m, 1H), 2.93 (d, J=7.21 Hz, 2H), 3.39 (br. s., 1H), 3.93 (br. s., 2H), 4.15 (br. s., 4H), 7.55 (d, J=7.77 Hz, 2H), and 8.14 (d, J=7.77 Hz, 2H).

HPLC purity 99.2/99.2%, ret. time=7.51 min. (A linear gradient using 5% acetonitrile, 95% water, and 0.05% TFA (Solvent A) and 95% acetonitrile, 5% water, and 0.05% TFA (Solvent B); t=0 min., 10% B, t=12 min., 100% B (15 min.) was employed on a SunFire C18 3.5 u 4.6×150 mm column. Flow rate was 2 ml/min and UV detection was set to 220/254 nm.).

HPLC purity 99.4/99.4%, ret. time=8.44 min. (A linear gradient using 5% acetonitrile, 95% water, and 0.05% TFA (Solvent A) and 95% acetonitrile, 5% water, and 0.05% TFA (Solvent B); t=0 min., 10% B, t=12 min., 100% B (15 min.) was employed on a XBridge Ph 3.5 u 4.6×150 mm column. Flow rate was 2 ml/min and UV detection was set to 220/254 nm.).

Example 21

1-(2-Fluoro-4-(5-(3-phenyl-4-(trifluoromethyl)isoxazol-5-yl)-1,2,4-oxadiazol-3-yl)benzyl)azetidine-3-carboxylic acid

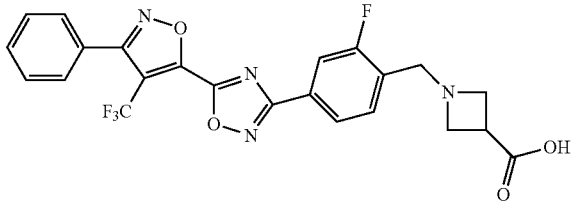

(21)

21-A. 3-Fluoro-4-(hydroxymethyl)benzonitrile

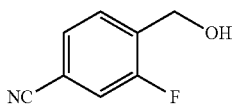

(21-A)

To a solution of 3-fluoro-4-formylbenzonitrile (3.6 g, 24.1 mmol) in methanol (40 mL) was added sodium borohydride (0.304 g, 8.04 mmol) slowly at room temperature. After 20 min., the reaction was complete by HPLC and LCMS. The reaction mixture was stirred at room temperature overnight. The reaction was quenched with water (~5 mL; stirred for 20 min.), and the methanol was removed under reduced pressure. The aqueous residue was diluted with dichloromethane (80 mL), washed with water (50 mL), and collected. The aqueous layer was extracted with dichloromethane (40 mL), and the combined organic layers were dried over anhydrous sodium sulfate. Concentration under reduced pressure afforded 3-fluoro-4-(hydroxymethyl)benzonitrile (3.51 g, 23.2 mmol, 96% yield) as a yellow solid. The compound had an HPLC ret. time=0.720 min.–Column: CHROMOLITH® SpeedROD 4.6×50 mm (4 min.); Solvent A=10% MeOH, 90% H$_2$O, 0.1% TFA; Solvent B=90% MeOH, 10% H$_2$O, 0.1% TFA. MS M$^{+1}$=152.09. $^1$H NMR (500 MHz, CDCl$_3$) δ ppm 4.85 (s, 2H), 7.35 (dd, J=9.43, 1.66 Hz, 1H), 7.50 (dd, J=7.91, 1.25 Hz, 1H), and 7.65 (t, J=7.49 Hz, 1H).

21-B. 3-Fluoro-N'-hydroxy-4-(hydroxymethyl)benzimidamide

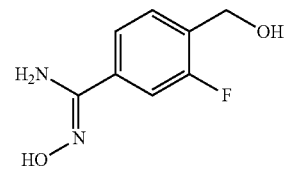

(21-B)

To a mixture of 3-fluoro-4-(hydroxymethyl)benzonitrile (3.51 g, 23.2 mmol) and hydroxylamine hydrochloride (3.23 g, 46.4 mmol) in methanol (100 mL) under nitrogen was added sodium bicarbonate (7.80 g, 93 mmol). The reaction mixture was stirred at room temperature for 5 min. and then immersed in an oil bath and heated at reflux for 2 h. HPLC analysis indicated that the starting material had been consumed. The heterogeneous mixture was filtered, the solid was washed with methanol, and the filtrate was concentrated under reduced pressure. The white solid residue was diluted with ethyl acetate (400 mL) but remained heterogeneous. The mixture was sonicated for 5 min and filtered under reduced pressure. The filtrated was washed with water (60 mL), and washed with a 10% aqueous solution of lithium chloride (60 mL), and washed with brine (60 mL). The combined aqueous layers were extracted with ethyl acetate (100 mL), and the combined organic layers were dried over anhydrous sodium sulfate. Concentration under reduced pressure afforded (Z)-3-fluoro-N'-hydroxy-4-(hydroxymethyl)benzimidamide (3.85 g, 20.9 mmol, 90% yield) as a white solid. The compound had an HPLC time=0.263 min.–Column. CHROMOLITH® SpeedROD 4.6×50 mm (4 min.); Solvent A=10% MeOH, 90% H$_2$O, 0.1% TFA; Solvent B=90% MeOH, 10% H$_2$O, 0.1% TFA. MS M$^{+1}$=184.9. $^1$H NMR (500 MHz, DMSO-d$_6$) δ ppm 4.54 (d, 2H), 5.28 (t, J=5.83 Hz, 1H), 5.86 (s, 2H), 7.40 (dd, J=11.65, 1.39 Hz, 1H), 7.44 (t, J=7.91 Hz, 1H), 7.51 (dd, J=8.05, 1.66 Hz, 1H), and 9.72 (s, 1H).

21-C. (2-Fluoro-4-(5-(3-phenyl-4-(trifluoromethyl) isoxazol-5-yl)-1,2,4-oxadiazol-3-yl)phenyl)methanol

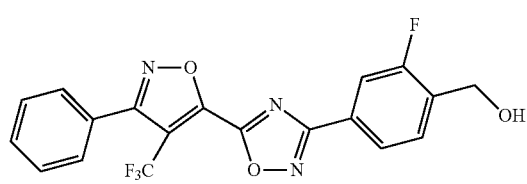

(21-C)

A heterogeneous mixture of 3-phenyl-4-(trifluoromethyl) isoxazole-5-carbonyl fluoride (1-E, 0.973 g, 3.75 mmol), 3-fluoro-N'-hydroxy-4-(hydroxymethyl)benzimidamide (0.691 g, 3.75 mmol), and Hunig's Base (0.852 mL, 4.88 mmol) in acetonitrile (7 mL) was stirred at room temperature over the weekend. The reaction mixture was diluted with dichloromethane, washed with a saturated aqueous solution of sodium bicarbonate, and dried over anhydrous sodium sulfate. The dichloromethane was removed under reduced pressure to give an orange oily residue which was purified by flash silica gel chromatography using a 20% mixture of ethyl acetate in hexane to give (2-fluoro-4-(5-(3-phenyl-4-(trifluoromethyl)isoxazol-5-yl)-1,2,4-oxadiazol-3-yl)phenyl)methanol (0.762 g, 1.88 mmol, 50% yield) as a pale yellow solid. The compound had an HPLC ret. time=3.33 min.–Column: CHROMOLITH® SpeedROD 4.6×50 mm (4 min.); Solvent A=10% MeOH, 90% H$_2$O, 0.1% TFA; Solvent B=90% MeOH, 10% H$_2$O, 0.1% TFA. MS M$^{+1}$=406.1.

21-D. 3-(4-(Bromomethyl)-3-fluorophenyl)-5-(3-phenyl-4-(trifluoromethyl)isoxazol-5-yl)-1,2,4-oxadiazole

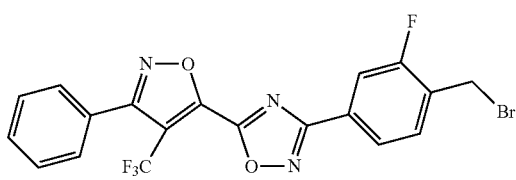

(21-D)

To a solution of (2-fluoro-4-(5-(3-phenyl-4-(trifluoromethyl)isoxazol-5-yl)-1,2,4-oxadiazol-3-yl)phenyl)methanol (1.95 mL, 0.740 mmol) in dichloromethane (8 mL) at 0° C. was added phosphorus tribromide (1.0M in dichloromethane) (0.740 mL, 0.740 mmol). After 5 minutes, the ice bath was removed, and the reaction mixture was stirred at room temperature overnight. The reaction mixture was diluted with dichloromethane, washed with a saturated aqueous solution of sodium bicarbonate, washed with brine, and dried over anhydrous sodium sulfate. The residue was triturated with methanol with sonication, filtered, and washed with methanol. Analysis of the white solid by HPLC and LCMS indicated that there was no significant amount of the desired product present. The filtrate was concentrated under reduced pressure, and the compound was loaded with a minimum amount of dichloromethane on a fritted funnel containing a layer of CELITE® topped with a layer of silica gel. The plug column was eluted with dichloromethane to give 3-(4-(bromomethyl)-3-fluorophenyl)-5-(3-phenyl-4-(trifluoromethyl)isoxazol-5-yl)-1,2,4-oxadiazole (0.173 g, 0.370 mmol, 50% yield) as a white solid. The compound had an HPLC ret. time=3.72 min.–Column: CHROMOLITH® SpeedROD 4.6×50 mm (4 min.); Solvent A=10% MeOH, 90% H$_2$O, 0.1% TFA; Solvent B=90% MeOH, 10% H$_2$O, 0.1% TFA. MS M$^{+1}$=468.0 and 470.0.

21-E. tert-Butyl 1-(2-fluoro-4-(5-(3-phenyl-4-(trifluoromethyl)isoxazol-5-yl)-1,2,4-oxadiazol-3-yl)benzyl)azetidine-3-carboxylate

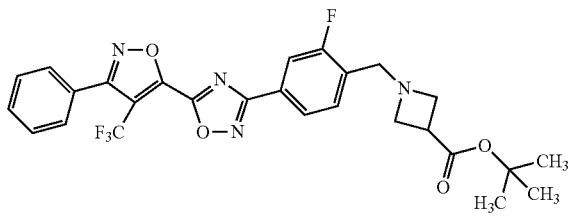

(21-E)

To a mixture of 3-(4-(bromomethyl)-3-fluorophenyl)-5-(3-phenyl-4-(trifluoromethyl)isoxazol-5-yl)-1,2,4-oxadiazole (0.080 g, 0.171 mmol) and tert-butyl azetidine-3-carboxylate, HCl salt (0.050 g, 0.256 mmol) at room temperature was added triethylamine (0.071 mL, 0.513 mmol) dropwise. The reaction mixture was stirred overnight at room temperature. The reaction mixture was diluted with dichloromethane, washed with a saturated aqueous solution of sodium bicarbonate, and dried over anhydrous sodium sulfate. Concentration under reduced pressure followed by purification by flash silica gel chromatography using a 20% mixture of ethyl acetate in hexane provided tert-butyl 1-(2-fluoro-4-(5-(3-phenyl-4-(trifluoromethyl)isoxazol-5-yl)-1,2,4-oxadiazol-3-yl)benzyl)azetidine-3-carboxylate (0.073 g, 0.134 mmol, 78% yield) as a white solid. The compound had an HPLC ret. time=3.07 min.–Column: CHROMOLITH® SpeedROD 4.6×50 mm (4 min.); Solvent A=10% MeOH, 90% H$_2$O, 0.1% TFA; Solvent B=90% MeOH, 10% H$_2$O, 0.1% TFA. MS M$^{+1}$=545.3.

21. 1-(2-Fluoro-4-(5-(3-phenyl-4-(trifluoromethyl)isoxazol-5-yl)-1,2,4-oxadiazol-3-yl)benzyl)azetidine-3-carboxylic acid A mixture of tert-butyl 1-(2-fluoro-4-(5-(3-phenyl-4-(trifluoromethyl)isoxazol-5-yl)-1,2,4-oxadiazol-3-yl)benzyl)azetidine-3-carboxylate (0.072 g, 0.132 mmol) and trifluoroacetic acid (3.06 mL, 39.7 mmol) were stirred at room temperature for 60 min. The trifluoroacetic acid was removed under reduced pressure, and the residue was diluted with water, the pH was adjusted to 4.5 (with sonication), and the solid was collected by vacuum filtration washed with water, and dried to give 61 mg of the product as a white solid. The solid was suspended in methanol with sonication, filtered under reduced pressure, washed with methanol, and dried well to give 1-(2-fluoro-4-(5-(3-phenyl-4-(trifluoromethyl)isoxazol-5-yl)-1,2,4-oxadiazol-3-yl)benzyl)azetidine-3-carboxylic acid (0.014 g, 0.028 mmol, 22% yield) as a white solid. The compound had an HPLC ret. time=2.72 min.–Column. CHROMOLITH® SpeedROD 4.6×50 mm (4 min.); Solvent A=10% MeOH, 90% H$_2$O, 0.1% TFA; Solvent B=90% MeOH, 10% H$_2$O, 0.1% TFA. MS M+1=489.4. $^1$H NMR (500 MHz, DMSO-d$_6$) δ ppm 3.21-3.31 (m, 3H), 3.46 (t, J=7.07 Hz, 2H), 3.68 (s, 2H), 7.61-7.70 (m, 6H), 7.83 (dd, J=10.13, 1.25 Hz, 1H), and 7.94 (dd, J=7.91, 1.53 Hz, 1H).

HPLC purity 99.6/99.4%, ret. time=7.51 min. (A linear gradient using 5% acetonitrile, 95% water, and 0.05% TFA (Solvent A) and 95% acetonitrile, 5% water, and 0.05% TFA (Solvent B); t=0 min., 10% B, t=12 min., 100% B (15 min.) was employed on a SunFire C18 3.5 u 3.0×150 mm column. Flow rate was 2 ml/min and UV detection was set to 220/254 nm.).

HPLC purity 99.8/99.5%, ret. time=8.85 min. (A linear gradient using 5% acetonitrile, 95% water, and 0.05% TFA (Solvent A) and 95% acetonitrile, 5% water, and 0.05% TFA (Solvent B); t=0 min., 10% B, t=12 min., 100% B (15 min.) was employed on a XBridge Ph 3.5 u 3.0×150 mm column. Flow rate was 2 ml/min and UV detection was set to 220/254 nm.).

Example 22

Preparation of 1-(2-methyl-4-(5-(3-phenyl-4-(trifluoromethyl)isoxazol-5-yl)-1,2,4-oxadiazol-3-yl)benzyl)azetidine-3-carboxylic acid

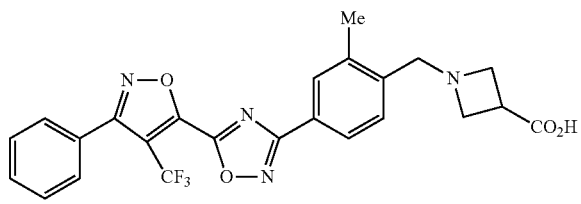

(22)

22-A. N'-Hydroxy-4-iodo-3-methylbenzimidamide

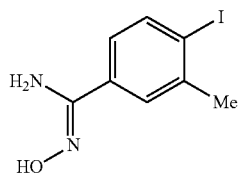

(22-A)

To a mixture of 4-iodo-3-methylbenzonitrile (3.59 g, 14.8 mmol) and hydroxylamine hydrochloride (2.05 g, 29.5 mmol) in methanol (75 mL) under nitrogen was added sodium bicarbonate (4.96 g, 59.1 mmol). The reaction mixture was stirred at room temperature for 5 min. and then immersed in an oil bath and heated at reflux for 2 h. The heterogeneous mixture was filtered, the solid was washed with methanol, and the filtrate was concentrated under reduced pressure. The white solid residue was diluted with ethyl acetate (300 mL) but remained heterogeneous. The mixture was sonicated for 5 min and filtered under reduced pressure. By HPLC, the solid appeared to be inorganic. The filtrated was washed with (50 mL), and washed with a 10% aqueous solution of lithium chloride (50 mL), and washed with brine (50 mL). The combined aqueous layers were extracted with ethyl acetate (2×50 mL), and the combined organic layers were dried over anhydrous sodium sulfate. Concentration under reduced pressure afforded N'-hydroxy-4-iodo-3-methylbenzimidamide (3.87 g, 14.0 mmol, 95% yield) as a white solid. The compound had an HPLC ret. time=0.993 min.–Column: CHROMOLITH® SpeedROD 4.6×50 mm (4 min.); Solvent A=10% MeOH, 90% $H_2O$, 0.1% TFA; Solvent B=90% MeOH, 10% $H_2O$, 0.1% TFA. MS $M^{+1}$=276.8. $^1$H NMR (500 MHz, CDCl$_3$) δ ppm 2.46 (s, 3H), 4.85 (br. s., 2H), 7.13 (dd, J=8.32, 2.22 Hz, 1H), 7.51 (d, J=1.66 Hz, 1H), and 7.84 (d, J=8.32 Hz, 1H).

22-B. 3-(4-Iodo-3-methylphenyl)-5-(3-phenyl-4-(trifluoromethyl)isoxazol-5-yl)-1,2,4-oxadiazole

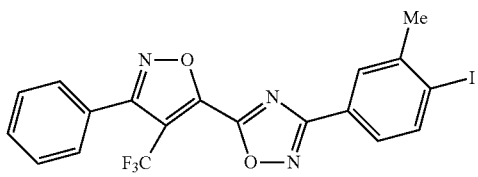

(22-B)

A heterogeneous mixture of 3-phenyl-4-(trifluoromethyl)isoxazole-5-carbonyl fluoride (1-E, 0.974 g, 3.76 mmol), N'-hydroxy-4-iodo-3-methylbenzimidamide (1.04 g, 3.76 mmol), and Hunig's Base (0.853 mL, 4.89 mmol) in acetonitrile (7 mL) was stirred at room temperature over the weekend. The reaction mixture was diluted with dichloromethane, washed with a saturated aqueous solution of sodium bicarbonate, and dried over anhydrous sodium sulfate. The dichloromethane was removed under reduced pressure, and the reddish residue was triturated with methanol with sonication (15 min.) and filtered to afford the product as an off-white solid. The filtrate was concentrated and triturated with methanol two additional times. The combined solids were dried well to give 3-(4-iodo-3-methylphenyl)-5-(3-phenyl-4-(trifluoromethyl)isoxazol-5-yl)-1,2,4-oxadiazole (1.45 g, 2.92 mmol, 78% yield) as an off-white white solid. The compound had an HPLC ret. time=4.01 min.–Column. CHROMOLITH® SpeedROD 4.6×50 mm (4 min.); Solvent A=10% MeOH, 90% $H_2O$, 0.1% TFA; Solvent B=90% MeOH, 10% $H_2O$, 0.1% TFA. MS $M^{+1}$=497.89.

22-C. 3-(3-Methyl-4-vinylphenyl)-5-(3-phenyl-4-(trifluoromethyl)isoxazol-5-yl)-1,2,4-oxadiazole

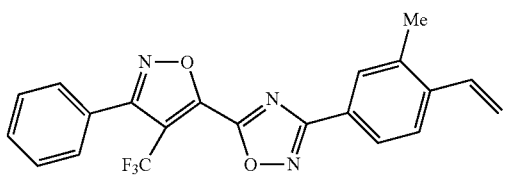

(22-C)

To a solution of 3-(4-iodo-3-methylphenyl)-5-(3-phenyl-4-(trifluoromethyl)isoxazol-5-yl)-1,2,4-oxadiazole (1.45 g, 2.92 mmol) in dioxane (5 mL) in a sealed tube was added sequentially tributyl(vinyl)stannane (0.942 mL, 3.21 mmol) and lithium chloride (0.371 g, 8.75 mmol). The mixture was degassed under reduced pressure and charged with nitrogen (2×). To the mixture was added tetrakis(triphenylphosphine)palladium(0) (0.337 g, 0.292 mmol), and the mixture was stirred under a strong stream of nitrogen for 5 min. The reaction mixture was sealed, immersed in an oil bath at 100° C., and stirred overnight. The reaction mixture was diluted with ethyl acetate and filtered. The solid was rinsed with ethyl acetate (3×). The filtrate was concentrated, diluted with ether, and filtered under reduced pressure. HPLC indicated that the product was in the filtrate, which was concentrated under reduced pressure and purified by flash silica gel chromatography using a mixture of ethyl acetate in hexane (1%-2.5%) to give 3-(3-methyl-4-vinylphenyl)-5-(3-phenyl-4-(trifluoromethyl)isoxazol-5-yl)-1,2,4-oxadiazole (0.514 g, 1.294 mmol, 44.4% yield) as an white solid. The compound had an HPLC ret. time=3.85 min.–Column. CHROMOLITH® SpeedROD 4.6×50 mm (4 min.); Solvent A=10% MeOH, 90% $H_2O$, 0.1% TFA; Solvent B=90% MeOH, 10% $H_2O$, 0.1% TFA. MS $M^{+1}$=398.0. $^1$H NMR (500 MHz, CDCl$_3$) δ ppm 2.47 (s, 3H), 5.43-5.46 (m, 1H), 7.00 (dd, J=17.34, 10.96 Hz, 1H), 7.53-7.62 (m, 3H) 7.65 (d, J=8.32 Hz, 1H), 7.69 (d, J=6.94 Hz, 2H), and 7.99-8.04 (m, 2H).

22-D. 2-Methyl-4-(5-(3-phenyl-4-(trifluoromethyl) isoxazol-5-yl)-1,2,4-oxadiazol-3-yl)benzaldehyde

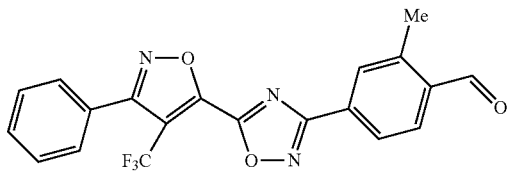

(22-D)

To a solution of 3-(3-methyl-4-vinylphenyl)-5-(3-phenyl-4-(trifluoromethyl)isoxazol-5-yl)-1,2,4-oxadiazole (0.250 g, 0.629 mmol) in dichloromethane (10 mL) at −78° C. was added ozone until the solution turned blue. The reaction mixture was purged with oxygen until the blue color disappeared and then nitrogen. To the reaction mixture was added triethylamine (0.263 mL, 1.89 mmol), and the mixture was stirred at room temperature for 15 min. Analysis by HPLC indicated that the starting material had been consumed. The solvent was removed under reduce pressure to give the product as a pale yellow solid. The compound was triturated with methanol with sonication, filtered, and dried to give 2-methyl-4-(5-(3-phenyl-4-(trifluoromethyl)isoxazol-5-yl)-1,2,4-oxadiazol-3-yl)benzaldehyde (0.150 g, 0.376 mmol, 60% yield) as a white solid. The product had an HPLC ret. time=3.48 min.–Column. CHROMOLITH® SpeedROD 4.6×50 mm (4 min.); Solvent A=10% MeOH, 90% H$_2$O, 0.1% TFA; Solvent B=90% MeOH, 10% H$_2$O, 0.1% TFA. $^1$H NMR (500 MHz, CDCl$_3$) δ ppm 2.81 (s, 3H), 7.54-7.63 (m, 3H), 7.70 (d, J=7.21 Hz, 2H), 8.00 (d, J=7.77 Hz, 1H), 8.14 (s, 1H), 8.21 (d, J=8.32 Hz, 1H), and 10.39 (s, 1H).

22. 1-(2-Methyl-4-(5-(3-phenyl-4-(trifluoromethyl) isoxazol-5-yl)-1,2,4-oxadiazol-3-yl)benzyl)azetidine-3-carboxylic acid To a mixture of 2-methyl-4-(5-(3-phenyl-4-(trifluoromethyl)isoxazol-5-yl)-1,2,4-oxadiazol-3-yl)benzaldehyde (0.050 g, 0.125 mmol) and azetidine-3-carboxylic acid (0.015 g, 0.150 mmol) in methanol (0.5 mL) and dichloroethane (0.5 mL) at room temperature was added 3 drops of acetic acid via a pasteur pipette. The reaction mixture was heated at 60° C. for 1 h. The reaction was cooled to room temperature, sodium cyanoborohydride (9.59 mg, 0.150 mmol) was added, and the mixture was stirred at room temperature overnight. The reaction mixture was diluted with dichloromethane, washed with water, washed with brine, and dried over anhydrous sodium sulfate. Concentration under reduced pressure afforded a white solid which was triturated with methanol with sonication and filtered. The resulting white solid was purified by flash silica gel chromatography using a mixture of methanol, dichloromethane, and ammonium hydroxide (10:90:0-20:80: 1) to give 1-(2-methyl-4-(5-(3-phenyl-4-(trifluoromethyl) isoxazol-5-yl)-1,2,4-oxadiazol-3-yl)benzyl)azetidine-3-carboxylic acid (0.032 g, 0.065 mmol, 52% yield) as a white solid. The compound had an HPLC ret. time=2.82 min.–Column: CHROMOLITH® SpeedROD 4.6×50 mm (4 min.); Solvent A=10% MeOH, 90% H$_2$O, 0.1% TFA; Solvent B=90% MeOH, 10% H$_2$O, 0.1% TFA. MS M$^{+1}$=485.2. $^1$H NMR (500 MHz, DMSO-d$_6$) δ ppm 2.38 (s, 3H), 3.17 (s, 2H), 3.22-3.24 (m, 1H), 3.46 (br. s., 2H), 3.63 (s, 2H), 7.51 (d, J=7.77 Hz, 1H), 7.57-7.73 (m, 5H), 7.86-7.94 (m, 2H), and 12.33 (br. s., 1H).

HPLC purity 99.3/99.1%, ret. time=7.62 min. (A linear gradient using 5% acetonitrile, 95% water, and 0.05% TFA (Solvent A) and 95% acetonitrile, 5% water, and 0.05% TFA (Solvent B); t=0 min., 10% B, t=12 min., 100% B (15 min.) was employed on a SunFire C18 3.5 u 3.0×150 mm column. Flow rate was 2 ml/min and UV detection was set to 220/254 nm.).

HPLC purity 99.4/99.2%, ret. time=8.90 min. (A linear gradient using 5% acetonitrile, 95% water, and 0.05% TFA (Solvent A) and 95% acetonitrile, 5% water, and 0.05% TFA (Solvent B); t=0 min., 10% B, t=12 min., 100% B (15 min.) was employed on a XBridge Ph 3.5 u 3.0×150 mm column. Flow rate was 2 ml/min and UV detection was set to 220/254 nm.).

Example 23

Preparation of 1-(3-chloro-4-(5-(3-phenyl-4-(trifluoromethyl)isoxazol-5-yl)-1,2,4-oxadiazol-3-yl)benzyl)azetidine-3-carboxylic acid

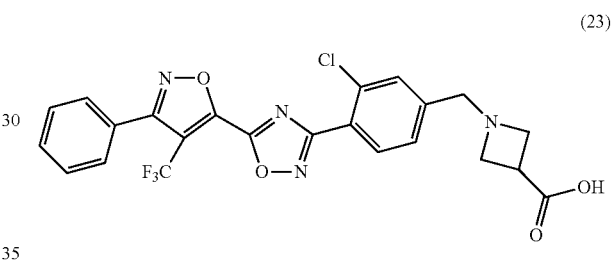

(23)

23-A. 4-(Bromomethyl)-2-chlorobenzonitrile

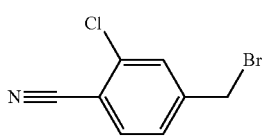

(23-A)

To a solution of 4-(bromomethyl)-2-chlorobenzonitrile (2.72 g, 17.4 mmol) in carbon tetrachloride (10 mL) at 85° C. was added a mixture of N-bromosuccinimide (3.83 g, 21.5 mmol) and benzoyl peroxide (1.15 g, 7.00 mmol) in 5 portions over 1 hr. After 25 min., an additional 6.0 mL of carbon tetrachloride was added to help dissolve the N-bromosuccinimide and AIBN portions being added. After 45 min., 10 mL of carbon tetrachloride and 5.0 mL of chloroform were added. Reflux was continued for 2.5 hrs. After cooling to room temperature, a saturated aqueous solution of sodium bicarbonate was added. The layers were separated, and the organic layer was washed with a saturated aqueous solution of sodium bicarbonate, dried over anhydrous sodium sulfate, and concentrated under reduced pressure to yield 4.02 g of a yellow oil. Flash silica gel chromatography with a mixture of hexane and ethyl acetate (500 mL of 99:1; 250 mL of 97:3; and 1.0 L of 95:5) yielded 4-(bromomethyl)-2-chlorobenzonitrile (2.30 g, 9.66 mmol, 54% yield) as a white solid. $^1$H NMR (400

MHz, CDCl₃) δ ppm 7.67 (1H, d, J=8.03 Hz), 7.56 (1H, d, J=1.51 Hz), 7.40 (1H, dd, J=8.03, 1.51 Hz), and 4.44 (2H, s).

23-B. tert-Butyl 1-(3-chloro-4-cyanobenzyl)azetidine-3-carboxylate

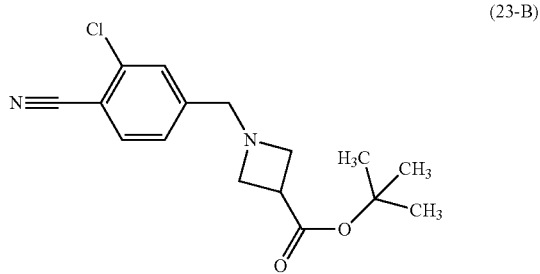 [SMILES: CC(C)(C)OC(=O)C1CN(Cc2ccc(C#N)c(Cl)c2)C1]

(23-B)

A solution of 4-(bromomethyl)-2-chlorobenzonitrile (2.30 g, 9.66 mmol), tert-butyl azetidine-3-carboxylate, HCl (0.084 g, 0.434 mmol), and diisopropylethylamine (0.189 mL, 1.09 mmol) in dimethylformamide was stirred at 60° C. for 2.33 hrs. HPLC indicated a 83% complete reaction. Additional diisopropylethylamine (0.189 mL, 1.09 mmol) and tert-butyl azetidine-3-carboxylate, HCl (64 mg) were added and stirring at 60° C. was continued for 1.5 hrs. The reaction mixture was cooled to room temperature, diluted with ethyl acetate, and washed with a 10% aqueous solution of lithium chloride. The organic layer was collected, washed with a 10% aqueous solution of sodium bicarbonate (2×), washed with brine, and dried over anhydrous sodium sulfate. Concentration under reduced pressure afforded tert-butyl 1-(3-chloro-4-cyanobenzyl)azetidine-3-carboxylate (0.138 g) as a tan oil. The compound had an HPLC ret. time=1.18 min.–Column: PHENOMENEX® S5 4.6×30 mm (2 min.); Solvent A=10% MeOH, 90% H₂O, 0.1% TFA; Solvent B=90% MeOH, 10% H₂O, 0.1% TFA. MS M$^{+1}$=307.06.

23-C. tert-Butyl 1-(3-chloro-4-(N'-hydroxycarbamimidoyl)benzyl)azetidine-3-carboxylate

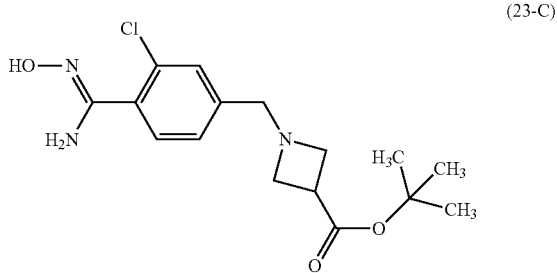 [SMILES: CC(C)(C)OC(=O)C1CN(Cc2ccc(/C(N)=N/O)c(Cl)c2)C1]

(23-C)

A solution of tert-butyl 1-(3-chloro-4-cyanobenzyl)azetidine-3-carboxylate (0.133 g, 0.434 mmol) in isopropanol (1.2 mL) with hydroxylamine hydrochloride (0.060 g, 0.868 mmol) and sodium bicarbonate (0.146 g, 1.74 mmol) was stirred at 90° C. for 6.5 hrs. HPLC and LCMS indicated the reaction was only 33% complete after 20 minutes. Additional hydroxylamine hydrochloride (0.060 g) and sodium bicarbonate (0.146 g) were added and heating was continued for 5 hrs. The isopropanol was removed under reduced pressure, and the reaction mixture was diluted with ethyl acetate and washed with water (2×), washed with brine, and dried over anhydrous sodium sulfate. Concentration under reduced pressure afforded tert-butyl 1-(3-chloro-4-(N'-hydroxycarbamimidoyl)benzyl)azetidine-3-carboxylate (142 mg) of a tan viscous taffy. The compound had an HPLC ret. time=0.795 min.–Column. PHENOMENEX® S5 4.6×30 mm (2 min.); Solvent A=10% MeOH, 90% H₂O, 0.1% TFA; Solvent B=90% MeOH, 10% H₂O, 0.1% TFA. MS M$^{+1}$=340.11.

23-D. tert-Butyl 1-(3-chloro-4-(5-(3-phenyl-4-(trifluoromethyl)isoxazol-5-yl)-1,2,4-oxadiazol-3-yl)benzyl)azetidine-3-carboxylate

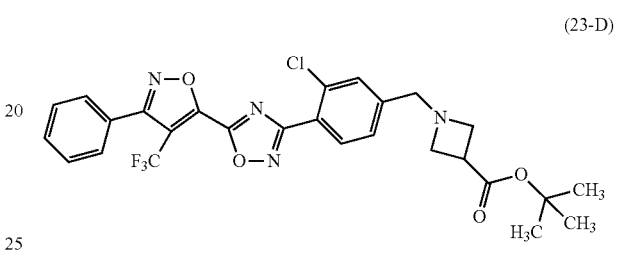

(23-D)

A mixture of 3-phenyl-4-(trifluoromethyl)isoxazole-5-carboxylic acid (1-D, 0.027 g, 0.105 mmol), tert-butyl 1-(3-chloro-4-(N'-hydroxycarbamimidoyl)benzyl)azetidine-3-carboxylate (0.036 g, 0.105 mmol), BOP-Cl (0.035 g, 0.136 mmol), and triethylamine (0.044 mL, 0.315 mmol) in N,N-dimethylformamide (1 mL) was shaken on platform shaker at room temperature overnight. The reaction mixture was diluted with dichloromethane, washed with a saturated aqueous solution of sodium bicarbonate, dried over anhydrous sodium sulfate, and concentrated under reduced pressure. The crude product was loaded on a fitted funnel containing a pad of CELITE® topped with a pad of silica gel, eluted with a 5% mixture of ethyl acetate in hexane, eluted with dichloromethane, and then eluted with a 20% mixture of ethyl acetate in hexane to give tert-butyl 1-(3-chloro-4-(5-(3-phenyl-4-(trifluoromethyl)isoxazol-5-yl)-1,2,4-oxadiazol-3-yl)benzyl)azetidine-3-carboxylate (0.013 g, 0.023 mmol, 22% yield) as a white solid. The compound had an HPLC ret. time=2.13 min.–Column. CHROMOLITH® SpeedROD 4.6×50 mm (4 min.); Solvent A=10% MeOH, 90% H₂O, 0.1% TFA; Solvent B=90% MeOH, 10% H₂O, 0.1% TFA. MS M$^{+1}$=561.2.

23. 1-(3-Chloro-4-(5-(3-phenyl-4-(trifluoromethyl)isoxazol-5-yl)-1,2,4-oxadiazol-3-yl)benzyl)azetidine-3-carboxylic acid A mixture of tert-butyl 1-(3-chloro-4-(5-(3-phenyl-4-(trifluoromethyl) isoxazol-5-yl)-1,2,4-oxadiazol-3-yl)benzyl) azetidine-3-carboxylate (0.0125 g, 0.022 mmol) and trifluoroacetic acid (1.0 mL) was stirred at room temperature for 45 min. The trifluoroacetic acid was removed under reduced pressure. The compound was dissolved in triethylamine and concentrated. The compound was then purified by flash silica gel chromatography using a mixture of methanol, dichloromethane, and ammonium hydroxide (10:90:0-20:80:1) to give the product as a colorless, viscous oil (9.5 mg). The sample was lyophilized (acetonitrile/water) to give 1-(3-chloro-4-(5-(3-phenyl-4-(trifluoromethyl)isoxazol-5-yl)-1,2,4-oxadiazol-3-yl)benzyl)azetidine-3-carboxylic acid (0.0035 g, 6.52 μmol, 29% yield) as a white solid. The compound had an HPLC ret. time=2.81 min.–Column. CHROMOLITH® SpeedROD 4.6×50 mm (4 min.); Solvent A=10% MeOH, 90% H$_2$O, 0.1% TFA; Solvent B=90% MeOH, 10% H$_2$O, 0.1% TFA. MS M$^{+1}$=504.9/507.0. $^1$H NMR (500 MHz, MeOD) δ ppm 3.37-3.45 (m, 1H), 4.01-4.12 (m, 4H), 4.29 (s, 2H), 7.56-7.65 (m, 4H), 7.69 (d, J=6.94 Hz, 2H), 7.77 (s, 1H), and 8.13 (d, J=8.05 Hz, 1H).

HPLC purity 94.8/96.6%, ret. time=7.71 min. (A linear gradient using 5% acetonitrile, 95% water, and 0.05% TFA (Solvent A) and 95% acetonitrile, 5% water, and 0.05% TFA (Solvent B); t=0 min., 10% B, t=12 min., 100% B (15 min.) was employed on a SunFire C18 3.5 u 4.6×150 mm column. Flow rate was 2 ml/min and UV detection was set to 220/254 nm.).

HPLC purity 95.4/96.3%, ret. time=9.01 min. (A linear gradient using 5% acetonitrile, 95% water, and 0.05% TFA (Solvent A) and 95% acetonitrile, 5% water, and 0.05% TFA (Solvent B); t=0 min., 10% B, t=12 min., 100% B (15 min.) was employed on a XBridge Ph 3.5 u 4.6×150 mm column. Flow rate was 2 ml/min and UV detection was set to 220/254 nm.).

Example 24

Preparation of 1-(4-(5-(3-phenyl-4-(trifluoromethyl)isoxazol-5-yl)-1,2,4-oxadiazol-3-yl)-3-(trifluoromethyl)benzyl)azetidine-3-carboxylic acid

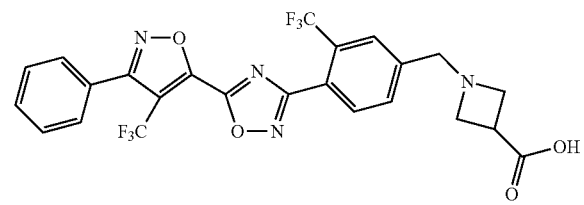

(24)

24-A.
4-(Bromomethyl)-2-(trifluoromethyl)benzonitrile

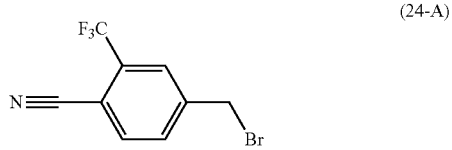 [SMILES: N#Cc1ccc(CBr)cc1C(F)(F)F]

(24-A)

To a solution of 4-(bromomethyl)-2-(trifluoromethyl)benzonitrile in carbon tetrachloride (20 mL) and chloroform (2 mL) at 85° C. was added a mixture of N-bromosuccinimide (3.31 g, 18.6 mmol) and AIBN (0.933 g, 6.05 mmol) in 5 portions over 1 hr. Precipitation occurred after several minutes. The reaction mixture was refluxed for 2.5 hrs. After 1.6 h, there was no product observed by HPLC. Additional chloroform was added (2.0 mL), and the reaction mixture was refluxed for 1.5 hrs. HPLC analysis indicated that the reaction had progressed slowly. Additional N-bromosuccinimide was added (0.30 eq, 0.83 g) along with AIBN (0.25 g, 0.10 eq) and chloroform (4 mL) and heating was continued. Analysis indicated that the reaction was complete after 2.5 hrs. After cooling to room temperature, a saturated aqueous solution of sodium bicarbonate was added. The layers were separated, and the organic layer was washed with a saturated aqueous solution of sodium bicarbonate, dried over anhydrous sodium sulfate, and concentrated under reduced pressure to yield 6.65 g of an orange oil. Flash chromatography on silica gel eluting with ethyl hexane and ethyl acetate (1 L of 99:1, 2 L of 97:3, and 2 L of 95:5) afforded 1.2 g of 4-(bromomethyl)-2-(trifluoromethyl)benzonitrile (1.20 g, 4.54 mmol, 29% yield) as a colorless oil which slowly solidified to a white solid. $^1$H NMR (400 MHz, CDCl$_3$) δ ppm 7.79-7.86 (2H, m), 7.71 (1H, dd, J=7.91, 1.38 Hz), 4.51 (2H, s).

24-B. tert-Butyl 1-(4-cyano-3-(trifluoromethyl)benzyl)azetidine-3-carboxylate

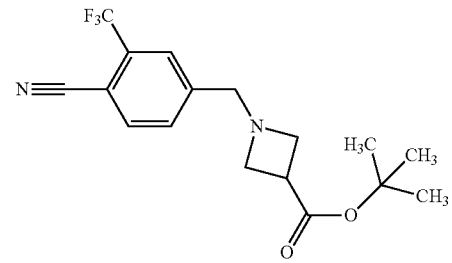

(24-B)

A solution of 4-(bromomethyl)-2-(trifluoromethyl)benzonitrile (0.223 g, 0.843 mmol), tert-butyl azetidine-3-carboxylate, HCl (0.201 g, 0.927 mmol), and diisopropylethylamine (0.74 mL, 4.21 mmol) in dimethylformamide was stirred at 60° C. for 1 hr. The reaction solution was cooled to room temperature, diluted with ethyl acetate, and washed with a 10% aqueous solution of lithium chloride. The organic layer was collected, washed with a 10% aqueous solution of lithium chloride (2×), washed with brine, and dried over anhydrous sodium sulfate. Concentration under reduced pressure yielded tert-butyl 1-(4-cyano-3-(trifluoromethyl)benzyl)azetidine-3-carboxylate (0.268 g, 0.787 mmol, 93%) as a viscous tan oil. The compound had an HPLC ret. time=1.26 min.–Column: PHENOMENEX® S5 4.6×30 mm (2 min.); Solvent A=10% MeOH, 90% H$_2$O, 0.1% TFA; Solvent B=90% MeOH, 10% H$_2$O, 0.1% TFA. MS M$^{+1}$=341.14.

24-C. tert-Butyl 1-(4-(N'-hydroxycarbamimidoyl)-3-(trifluoromethyl)benzyl)azetidine-3-carboxylate

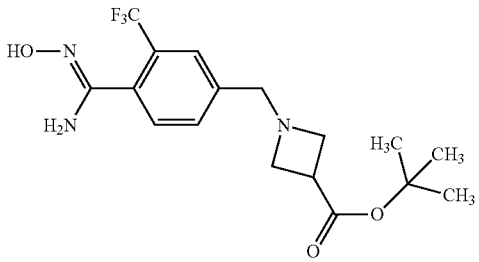

(24-C)

A solution of tert-butyl 1-(4-cyano-3-(trifluoromethyl)benzyl)azetidine-3-carboxylate (0.268 g, 0.787 mmol), hydroxylamine hydrochloride (0.109 g, 1.57 mmol), and sodium bicarbonate (0.265 g, 3.15 mmol) in isopropanol (2.2 mL) was stirred at 90° C. for 6.0 hrs. HPLC and LCMS indicated that the reaction was 69% complete. Additional hydroxylamine hydrochloride (0.109 g), sodium bicarbonate (0.265 g), and isopropanol (2.2 mL) were added, and heating was continued for 16 hrs. The isopropanol was removed under reduced pressure, and the reaction mixture was diluted with ethyl acetate and washed with water (2×), washed with brine, and dried over anhydrous sodium sulfate. Concentration under reduced pressure afforded tert-butyl 1-(4-(N'-hydroxycarbamimidoyl)-3-(trifluoromethyl)benzyl)azetidine-3-carboxylate (0.258 g, 0.690 mmol, 88% yield) of a colorless, viscous oil. The compound had an HPLC ret. time=0.880 min.–Column: PHENOMENEX® S5 4.6×30 mm (2 min.); Solvent A=10% MeOH, 90% H$_2$O, 0.1% TFA; Solvent B=90% MeOH, 10% H$_2$O, 0.1% TFA. MS M$^{+1}$=374.10.

24-D. tert-Butyl 1-(4-(5-(3-phenyl-4-(trifluoromethyl)isoxazol-5-yl)-1,2,4-oxadiazol-3-yl)-3-(trifluoromethyl)benzyl)azetidine-3-carboxylate (24-D)

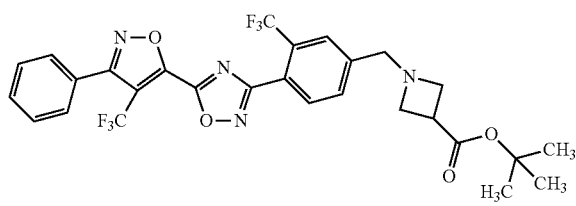

A mixture of 3-phenyl-4-(trifluoromethyl)isoxazole-5-carboxylic acid (0.030 g, 0.104 mmol), tert-butyl 1-(4-(N'-hydroxycarbamimidoyl)-3-(trifluoromethyl)benzyl)azetidine-3-carboxylate (0.039 g, 0.104 mmol), BOP-Cl (0.035 g, 0.136 mmol), and triethylamine (0.044 mL, 0.313 mmol) in N,N-dimethylformamide (1 mL) was shaken on platform shaker at room temperature overnight. The reaction mixture was diluted with dichloromethane, washed with a saturated aqueous solution of sodium bicarbonate, dried over anhydrous sodium sulfate, and concentrated under reduced pressure. The crude product was purified by flash silica gel chromatography using a mixture of 20% mixture of ethyl acetate in hexane to give tert-butyl 1-(4-(5-(3-phenyl-4-(trifluoromethyl)isoxazol-5-yl)-1,2,4-oxadiazol-3-yl)-3-(trifluoromethyl)benzyl)azetidine-3-carboxylate (0.010 g, 0.017 mmol, 16% yield) as a white solid. The compound had an HPLC ret. time=3.16 min.–Column. CHROMOLITH® SpeedROD 4.6×50 mm (4 min.); Solvent A=10% MeOH, 90% H$_2$O, 0.1% TFA; Solvent B=90% MeOH, 10% H$_2$O, 0.1% TFA. MS M$^{+1}$=595.2.

24. 1-(4-(5-(3-Phenyl-4-(trifluoromethyl)isoxazol-5-yl)-1,2,4-oxadiazol-3-yl)-3-(trifluoromethyl)benzyl)azetidine-3-carboxylic acid A mixture of tert-butyl 1-(4-(5-(3-phenyl-4-(trifluoromethyl)isoxazol-5-yl)-1,2,4-oxadiazol-3-yl)-3-(trifluoromethyl)benzyl)azetidine-3-carboxylate (0.010 g, 0.017 mmol) and trifluoroacetic acid (1.0 mL) was stirred at room temperature for 45 min. The trifluoroacetic acid was removed under reduced pressure. The compound was dissolved in triethylamine and concentrated. The compound was then purified by flash silica gel chromatography using a mixture of methanol, dichloromethane, and ammonium hydroxide (10:90:0-20:80:1) to give the product as a colorless, viscous oil (6.8 mg). The sample was lyophilized (acetonitrile/water) to give 1-(4-(5-(3-phenyl-4-(trifluoromethyl)isoxazol-5-yl)-1,2,4-oxadiazol-3-yl)-3-(trifluoromethyl)benzyl)azetidine-3-carboxylic acid (0.0065 g, 0.011 mmol, 68% yield) as an off-white solid. The product was >99% pure by HPLC with a ret. time=2.86 min.–Column. CHROMOLITH® SpeedROD 4.6×50 mm (4 min.); Solvent A=10% MeOH, 90% H$_2$O, 0.1% TFA; Solvent B=90% MeOH, 10% H$_2$O, 0.1% TFA. MS M$^{+1}$=539.0. $^1$H NMR (500 MHz, DMSO-d$_6$) δ ppm 3.16-3.23 (m, 1H), 3.25 (t, J=6.80 Hz, 2H), 3.42-3.47 (m, 2H), 3.75 (s, 2H), 7.60-7.69 (m, 5H), 7.82 (d, J=7.77 Hz, 1H), 7.90 (s, 1H), and 7.94 (d, J=7.77 Hz, 1H).

HPLC purity 96.9/98.9%, ret. time=7.90 min. (A linear gradient using 5% acetonitrile, 95% water, and 0.05% TFA (Solvent A) and 95% acetonitrile, 5% water, and 0.05% TFA (Solvent B); t=0 min., 10% B, t=12 min., 100% B (15 min.) was employed on a SunFire C18 3.5 u 4.6×150 mm column. Flow rate was 2 ml/min and UV detection was set to 220/254 nm.).

HPLC purity 97.1/99.0%, ret. time=9.09 min. (A linear gradient using 5% acetonitrile, 95% water, and 0.05% TFA (Solvent A) and 95% acetonitrile, 5% water, and 0.05% TFA (Solvent B); t=0 min., 10% B, t=12 min., 100% B (15 min.) was employed on a XBridge Ph 3.5 u 4.6×150 mm column. Flow rate was 2 ml/min and UV detection was set to 220/254 nm.).

$^1$H NMR (500 MHz, DMSO-d$_6$) δ ppm 3.16-3.23 (m, 1H), 3.25 (t, J=6.80 Hz, 2H), 3.42-3.47 (m, 2H), 3.75 (s, 2H), 7.60-7.69 (m, 5H), 7.82 (d, J=7.77 Hz, 1H), 7.90 (s, 1H), and 7.94 (d, J=7.77 Hz, 1H).

Example 25

1-(4-(5-(4,5-Diphenylisoxazol-3-yl)-1,2,4-oxadiazol-3-yl)-3-(trifluoromethyl)benzyl)azetidine-3-carboxylic acid, 2,2,2-trifluoroacetic acid salt (25)

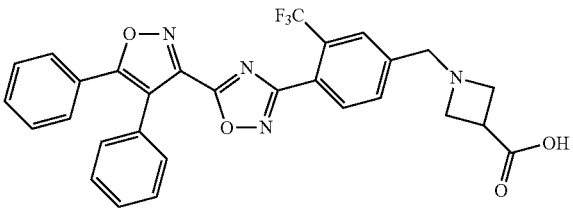

25-A. N'-Hydroxy-4-methyl-2-(trifluoromethyl)benzimidamide (25-A)

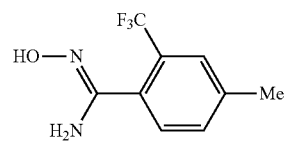

An oven-dried 20 mL reaction vial containing a stir bar was cooled under a stream of dry nitrogen. The vial was charged with 4-methyl-2-(trifluoromethyl)benzonitrile (1000 mg, 5.40 mmol), hydroxylamine hydrochloride (469 mg, 6.75 mmol), sodium bicarbonate (681 mg, 8.10 mmol), and methanol (6 mL). The vial was flushed with nitrogen, sealed, stirred at room temperature for 30 minutes, and then placed in a sand bath set to 75° C. and stirred overnight. The crude reaction material was purified by reverse phase preparative HPLC. The collected product fractions were evaporated under vacuum to afford N'-hydroxy-4-methyl-2-(trifluoromethyl)benzimidamide (0.54 g, 2.45 mmol, 45% yield). MS M$^{+1}$=219.0.

25-B. 5-(4,5-Diphenylisoxazol-3-yl)-3-(4-methyl-2-(trifluoromethyl)phenyl)-1,2,4-oxadiazole

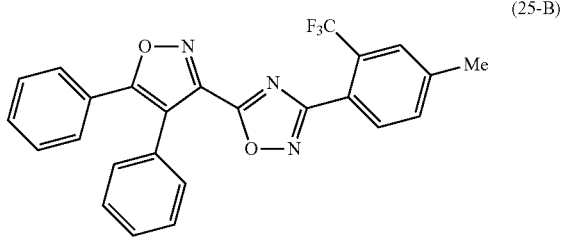 [SMILES: Cc1ccc(-c2noc(-c3noc(-c4ccccc4)c3-c3ccccc3)n2)c(C(F)(F)F)c1]

(25-B)

A 2 dram reaction vial containing a stir bar was charged with 4,5-diphenylisoxazole-3-carboxylic acid (17-B, 48.6 mg, 0.183 mmol), EDC (43.9 mg, 0.229 mmol), HOBT (35.1 mg, 0.229 mmol), and dimethylformamide (1 mL). The vial was flushed with dry nitrogen, sealed, and the reaction was stirred at room temperature for 30 minutes. N'-Hydroxy-4-methyl-2-(trifluoromethyl)benzimidamide (40.0 mg, 0.183 mmol) was introduced. The vial was flushed with dry nitrogen, sealed, stirred at room temperature for 30 minutes, and then placed on a reactor block set to 60° C. overnight. Water was added dropwise (~0.5 mL) until the solution remained cloudy, and then the reaction was cooled to room temperature. Additional water (5 mL) was added after cooling, and the reaction was placed in a sonicator bath for 60 min. A gummy solid formed on the side of the flask and stir bar. The aqueous solution was decanted and the residue washed with water and then partially dried under a stream of air. The gummy solid was dissolved in methanol (1-2 mL), transferred, and evaporated to dryness to give a pale yellow solid The pale yellow solid was purified by flash chromatography (12 g Isco silica gel). Elution with dichloromethane afforded the major product. The product containing fractions were evaporated to afford 5-(4,5-diphenylisoxazol-3-yl)-3-(4-methyl-2-(trifluoromethyl)phenyl)-1,2,4-oxadiazole (24 mg) MS M$^{+1}$=448.1.

25. 1-(4-(5-(4,5-Diphenylisoxazol-3-yl)-1,2,4-oxadiazol-3-yl)-3-(trifluoromethyl)benzyl)-azetidine-3-carboxylic acid, 2,2,2-trifluoroacetic acid salt A 2-dram vial containing a stir bar was charged with 5-(4,5-diphenylisoxazol-3-yl)-3-(4-methyl-2-(trifluoromethyl)phenyl)-1,2,4-oxadiazole (22 mg, 0.049 mmol) in chloroform (3 mL), and the vial was placed on a reactor block set to 65° C. N-bromosuccinimide (17.5 mg, 0.098 mmol) followed by AIBN (4.04 mg, 0.025 mmol) were added and the vial was sealed. After 1.5 h, additional N-bromosuccinimide (20 mg) was added, and the reaction left overnight at 65° C. Water (2 mL) and chloroform (2 mL) were added, and the reaction was vortexed to mix thoroughly. The organic phase was washed with water (2 mL) and brine (2 mL) before being dried over anhydrous sodium sulfate, filtered, and concentrated to dryness to afford a pale yellow film The residue was dissolved in dimethylformamide (1 mL) and tert-butyl azetidine-3-carboxylate, acetic acid salt (21.4 mg, 0.098 mmol) was added. The reaction was left to stir at room temperature for four days. Additional tert-butyl azetidine-3-carboxylate, acetic acid salt (20 mg) and triethylamine (0.030 mL) were added. The reaction was stirred at room temperature overnight and then at 60° C. for an additional day. The crude reaction mixture was purified by reverse phase preparative HPLC. The product containing fraction was evaporated to dryness, and the resulting residue was dissolved in TFA (0.5 mL) and allowed to stand at room temperature. The TFA was evaporated, and the residue was re-evaporated from methanol and left under high vacuum to afford 1-(4-(5-(4,5-diphenylisoxazol-3-yl)-1,2,4-oxadiazol-3-yl)-3-(trifluoromethyl)benzyl)azetidine-3-carboxylic acid, TFA (1.9 mg, 2.76 mmol). The compound had an HPLC retention time=3.52 min.–Column. CHROMOLITH® SpeedROD 4.6×50 mm (4 min.); Solvent A=10% MeOH, 90% H$_2$O, 0.2% H$_3$PO$_4$; Solvent B=90% MeOH, 10% H$_2$O, 0.2% H$_3$PO$_4$. LC/MS M$^{+1}$=547.0 $^1$H NMR (400 MHz, MeOD) δ ppm 3.73 (m, 1H) 4.39-4.41 (m, 4H) 4.60 (s, 2H) 7.39-7.50 (m, 8H) 7.57-7.59 (m, 2H) 7.87-7.95 (m, 2H) 8.06 (s, 1 H).

Comparative Compound A (Comp. A)

1-(4-(5-(4-Phenyl-5-(trifluoromethyl)thiophen-2-yl)-1,2,4-oxadiazol-3-yl)benzyl)azetidine-3-carboxylic acid A comparative Compound (Comp. A) was prepared for evaluation. This compound is Example 54 from WO 2003/062252 which has also been described in Hale et al., *J. Med. Chem.*, 6662 (2004).

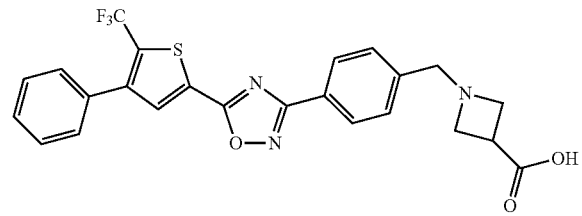

(Comp. A)

Comp. A-1. (Z)-tert-Butyl 1-(4-(N'-(4-phenyl-5-(trifluoromethyl)thiophene-2-carbonyloxy)-carbamimidoyl)benzyl)azetidine-3-carboxylate

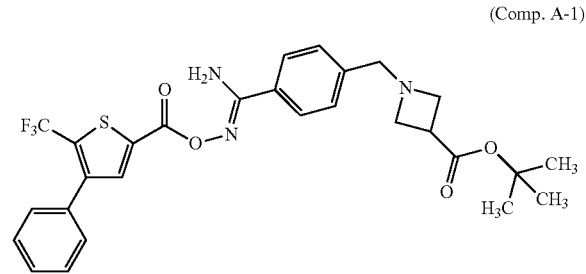 [SMILES: CC(C)(C)OC(=O)C1CN(Cc2ccc(/C(N)=N/OC(=O)c3cc(-c4ccccc4)c(C(F)(F)F)s3)cc2)C1]

(Comp. A-1)

A mixture of 4-phenyl-5-(trifluoromethyl)thiophene-2-carboxylic acid (408 mg, 1.50 mmol), (Z)-tert-butyl 1-(4-(N'-hydroxycarbamimidoyl)benzyl)azetidine-3-carboxylate (Int.1, 458 mg, 1.50 mmol), HOBt (345 mg, 2.250 mmol), Hunig's Base (1.05 mL, 6.00 mmol), and EDC (431 mg, 2.25 mmol) in N,N-dimethylformamide (7.5 mL) was stirred at room temperature for 18 h. The reaction mixture was partitioned between ethyl acetate (120 mL) and a saturated aqueous solution of sodium bicarbonate (60 mL). The organic layer was washed with water (2×120 mL), washed with brine (120 mL), and dried over anhydrous magnesium sulfate. Concentration under reduced pressure afforded (Z)-tert-butyl 1-(4-(N'-(4-phenyl-5-(trifluoromethyl)thiophene-2-carbonyloxy)carbamimidoyl)benzyl)azetidine-3-carboxylate (744 mg, 1.33 mmol, 89% yield) as a light peach colored solid that was used in the next step without further purification. HPLC: ret. time=3.26 minutes (YMC Combi S-5 4.6×50 mm ODS column) eluting with 10-90% aqueous methanol+0.2% phosphoric acid over a 4 minute gradient. MS: (M+H)=560.25.

Comp. A-2. tert-Butyl 1-(4-(5-(4-phenyl-5-(trifluoromethyl)thiophen-2-yl)-1,2,4-oxadiazol-3-yl)benzyl)azetidine-3-carboxylate (Comp. A-2)

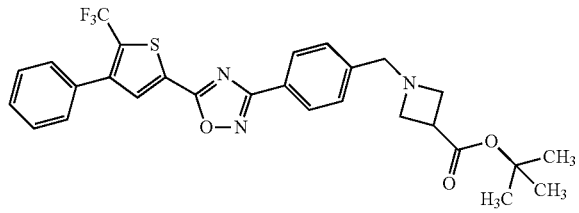

To a solution of (Z)-tert-butyl 1-(4-(N'-(4-phenyl-5-(trifluoromethyl)thiophene-2-carbonyloxy)carbamimidoyl)benzyl)azetidine-3-carboxylate (744 mg, 1.33 mmol) in acetonitrile (30 mL) was added a 1M solution of TBAF in tetrahydrofuran (3.99 mL, 3.99 mmol), and the reaction mixture was allowed to stir at room temperature for 3 days. The volatiles were removed under reduced pressure, and the residue was chromatographed on a 5×12 cm silica gel column, eluting with a 0-50% EtOAc/Hex gradient. The essentially pure fractions containing product were concentrated to afford tert-butyl 1-(4-(5-(4-phenyl-5-(trifluoromethyl)thiophen-2-yl)-1,2,4-oxadiazol-3-yl)benzyl)azetidine-3-carboxylate (521 mg, 0.962 mmol, 72.4% yield) as a colorless solid. HPLC ret. time=3.63 min. (YMC Combi S-5 4.6×50 mm ODS column) eluting with 10-90% aqueous methanol+0.2% phosphoric acid over a 4 minute gradient. MS: (M+H) =542.22. $^1$H NMR (500 MHz, CDCl$_3$) δ ppm 1.46 (s, 9H), 3.25-3.31 (m, 3H), 3.52-3.58 (m, 2H), 3.69 (s, 2H), 7.43 (d, J=8.25 Hz, 2H), 7.47 (m, 5H), 7.91 (s, d, J=1.65 Hz, 1H), and 8.09 (d, J=8.25 Hz, 2H).

Comp. A. 1-(4-(5-(4-Phenyl-5-(trifluoromethyl)thiophen-2-yl)-1,2,4-oxadiazol-3-yl)benzyl)-azetidine-3-carboxylic acid A solution of tert-butyl 1-(4-(5-(4-phenyl-5-(trifluoromethyl)thiophen-2-yl)-1,2,4-oxadiazol-3-yl)benzyl)azetidine-3-carboxylate (518 mg, 0.956 mmol) in trifluoroacetic acid (15 mL) was allowed to stand at room temperature for 1.5 h. The volatiles were removed under reduced pressure, and the residue was co-evaporated from ethyl acetate/hexanes. (2×10 mL). The residue was suspended in water (10 mL) and the pH was adjusted to ~11 with 1N aqueous sodium hydroxide. To this solution was added sufficient 1N aqueous hydrochloric acid to adjust the pH ~4.5. The resulting suspension was stirred at room temperature overnight. The white suspension was filtered through a medium porosity sintered glass filter, and the filter cake was washed thoroughly with water. The solid was dried, the white powder was suspended in methanol, and the suspension was sonicated until it was uniform. The methanol was removed under reduced pressure, and the procedure was repeated twice more to afford a white solid that was stirred as a suspension in methanol (~30 mL) overnight. Vacuum filtration and drying afforded 1-(4-(5-(4-phenyl-5-(trifluoromethyl)thiophen-2-yl)-1,2,4-oxadiazol-3-yl)benzyl)-azetidine-3-carboxylic acid (345 mg, 0.707 mmol, 74% yield) as a white powder. HPLC ret. time=3.45 min. (YMC Combi S-5 4.6×50 mm ODS column) eluting with 10-90% aqueous methanol+0.2% phosphoric acid over a 4 minute gradient. MS: (M+H)=486.12. $^1$H NMR (400 MHz, DMSO-d$_6$) δ ppm 3.23 (s, 3H), 3.39-3.45 (m, 2H), 3.64 (s, 2H), 7.50 (d, J=8.28 Hz, 2H), 7.58 (m, 5H), 8.02 (d, J=8.28 Hz, 2H), and 8.26 (d, J=1.25 Hz, 1H). Elemental Analysis: Calc. for $C_{24}H_{18}N_3O_3SF_3 \cdot 0.1H_2O$: C 59.22; H, 3.76; N, 8.63, S 6.59, F 11.71. Found: $C_{24}H_{18}N_3O_3SF_3 \cdot 0.1H_2O$: C 59.06; H, 3.45; N, 8.60, S 6.61, F 11.42; KF (Found)=0.25% water.

Biological Assays

S1P$_1$ Binding Assay

Membranes were prepared from CHO cells expressing human S1P$_1$. Cells were dissociated in buffer containing 20 mM HEPES, pH 7.5, 50 mM NaCl, 2 mM EDTA and Protease Inhibitor cocktail (Roche), and disrupted on ice using the Polytron homogenizer. The homogenate was centrifuged at 20,000 rpm (48,000 g) and the supernatant was discarded. The membrane pellets were resuspended in buffer containing 50 mM HEPES, pH 7.5, 100 mM NaCl, 1 mM MgCl$_2$, 2 mM EDTA and stored in aliquots at −80° C. after protein concentration determination.

Membranes (2 μg/well) and 0.03 nM final concentration of $^{33}$P-S1P ligand (1 mCi/ml, American Radiolabeled Chemicals) were added to the compound plates. Binding was performed for 60 min at room temperature, terminated by collecting the membranes onto GF/B filter plates, and radioactivity was measured by TOPCOUNT®. The competition data of the test compounds over a range of concentrations was plotted as percentage inhibition of radioligand specific binding. The IC$_{50}$ is defined as the concentration of competing ligand needed to reduce specific binding by 50%.

Compounds of the present invention and Comparative Compound A were tested in the S1P$_1$ binding assay described hereinabove and the results rounded to two digits, shown in Table A were obtained. In some instances, the value is an average of multiple experiments where N is the number of experiments conducted that provided satisfactory dose response curves. When more than one batch of an example was tested, the value presented is from the batch which allowed a comparison of GTPγS S1P$_1$ and GTPγS S1P$_3$ in Method A (Data shown in Table B). Data was not averaged across different batches of an example compound.

TABLE A

| Ex. | S1P$_1$ Binding IC$_{50}$ (nM) | N |
|---|---|---|
| 1 | 0.091 | 2 |
| 2 | 0.050 | 1 |
| 3 | 0.065 | 1 |
| 4 | 0.17 | 1 |
| 5 | 0.14 | 1 |
| 6 | 0.043 | 1 |
| 7 | 0.58 | 2 |
| 8 | 0.090 | 1 |
| 9 | 0.14 | 1 |
| 10 | 0.055 | 1 |
| 11 | 0.13 | 1 |
| 12 | 0.078 | 1 |
| 13 | 0.094 | 1 |
| 14 | 0.70 | 1 |
| 15 | 6.5 | 1 |
| 16 | 40 | 1 |
| 17 | 0.063 | 2 |
| 18 | 0.14 | 1 |
| 19 | 0.30 | 1 |
| 20 | 0.15 | 2 |
| 21 | 0.32 | 2 |
| 22 | 0.55 | 2 |
| 23 | 0.26 | 1 |
| 24 | 1.56 | 1 |
| 25 | 0.44 | 1 |
| Comp. A | 2.5 | 1 |

Method A: Receptor [35S] GTPγS Binding Assays

Compounds were loaded in a 384 Falcon v-bottom plate (0.5 μl/well in a 3-fold dilution). Membranes prepared from S1P$_1$/CHO cells or EDG3-Gα15-bla HEK293T cells were added to the compound plate (40 μl/well, final protein 3 mg/well) with MULTIDROP®. [$^{35}$S]GTP (1250 Ci/mmol, Perkin Elmer) was diluted in assay buffer: 20 mM HEPES, pH7.5, 10 mM MgCl$_2$, 150 mM NaCl, 1 mM EGTA, 1 mM DTT, 10 μM GDP, 0.1% fatty acid free BSA, and 10 mg/ml Saponin to 0.4 nM. 40 μl of the [$^{35}$S] GTP solution was added to the compound plate with a final concentration of 0.2 nM. The reaction was kept at room temperature for 45 min. At the end of incubation, all the mixtures in the compound plate were transferred to a 384 well FB filter plates via GPCR robot system. The filter plate was washed with water 4 times by using the modified manifold Embla plate washer and dried at 60° C. for 45 min. 30 μl of MicroScint 20 scintillation fluid was added to each well for counting at Packard TOP-COUNT®. EC$_{50}$ is defined as the agonist concentration that corresponds to 50% of the Ymax (maximal response) obtained for each individual compound tested.

Method B: Receptor [$^{35}$S] GTPγS SPA Binding Assays

Membranes prepared from S1P$_1$ or S1P$_3$ transfected CHO cells (2 μg protein) were incubated in 96-well white plates (CORNING® 3693) with test compounds diluted in DMSO, in 50 μl of reaction mixture containing 7.5 μl WGA-PVT beads (20 mg/ml), and 5 μM GDP, 20 mM HEPES pH 7.4, 100 mM NaCl, 1 mM EDTA, 5 mM MgCl$_2$, 10 μg/ml saponin, 0.1% BSA, and 1 μM leupeptin. The assay was initiated with the addition of 25 μl of 0.2 nM [$^{35}$S]-GTPγS (1250 Ci/mmol; NEN) in assay buffer. After 90 min incubation at room temperature, spin the plate at 1000 rpm for 5 min. The bound radionuclides were measured at TOPCOUNT®, expressed as % response relative to S1P (1 μM) activation. Data was analyzed using the four parameter logistic equation in Excel. The four parameters in the equation, $Y=A+((B-A)/(1+((EC_{50}/X)^D)))$, are described as following: A is the Y value (agonist activity) at the bottom plateau; B is the Y value at the top plateau; EC$_{50}$ is the X value (agonist concentration) when the response is halfway between bottom and top; D is Hill coefficient. Curves were not generated for compounds having Ymax values were below 50%.

Compounds of the present invention and Comparative Compound A were tested in the Receptor [$^{35}$S] GTPγS Binding Assays (Method A) and Receptor [35S] GTPγS SPA Binding Assays (Method B) described hereinabove and the results rounded to two digits, shown in Table B were obtained. In some instances, the value is an average of multiple experiments where N is the number of experiments conducted that provided satisfactory dose response curves. When more than one batch of an example was tested, the value presented is from a batch which allowed a comparison of GTPγS S1P$_1$ and GTPγS S1P$_3$ in which the most number of experiments were performed. Preferably, the same batch was examined in Method A and Method B. Data was not averaged across different batches of an example compound.

TABLE B

| | Method A | | | | Method B | | | |
|---|---|---|---|---|---|---|---|---|
| Ex. | GTPγS S1P$_1$ EC$_{50}$ (nM) | N | GTPγS S1P$_3$ EC$_{50}$ (nM) | N | GTPγS S1P$_1$ EC$_{50}$ (nM) | N | GTPγS S1P$_3$ EC$_{50}$ (nM) | N |
| 1 | 0.68 | 2 | 940 | 2 | 0.048 | 12 | 510 | 11 |
| 2 | 1.7 | 1 | 3600 | 1 | 0.076 | 10 | 350 | 9 |
| 3 | 0.26 | 1 | 330 | 1 | 0.16 | 2 | NC | 0 |
| 4 | 0.70 | 1 | 470 | 1 | 0.58 | 4 | ND | 0 |
| 5 | 5.3 | 1 | 1700 | 1 | NC | 0 | ND | 0 |
| 6 | 5.6 | 1 | 420 | 1 | 0.22 | 1 | NC | 0 |
| 7 | 6.6 | 1 | 3,700 | 1 | 1.5 | 1 | 8,100 | 1 |
| 8 | 3.7 | 1 | 520 | 1 | NC | 0 | ND | 0 |
| 9 | 3.1 | 1 | 2,500 | 1 | 0.14 | 11 | 910 | 1 |
| 10 | 0.84 | 1 | 190 | 1 | 0.055 | 1 | ND | 0 |
| 11 | 0.47 | 1 | ND | 0 | 0.017 | 1 | 50 | 1 |
| 12 | ND | 0 | 3,600 | 1 | 0.15 | 6 | 1,600 | 1 |
| 13 | 1.9 | 1 | 1,100 | 1 | ND | 0 | ND | 0 |
| 14 | 150 | 1 | 5,200 | 1 | 1.2 | 1 | ND | 0 |
| 15 | 29 | 1 | 5,100 | 1 | ND | 0 | ND | 0 |
| 16 | 112 | 1 | 2,050 | 1 | ND | 0 | ND | 0 |
| 17 | 0.73 | 13 | 20 | 39 | 0.12 | 2 | 13.5 | 2 |
| 18 | 1.0 | 1 | ND | 0 | 0.015 | 1 | 21 | 1 |
| 19 | 3.0 | 1 | 810 | 1 | 0.72 | 1 | NC | 0 |
| 20 | 0.56 | 2 | 2,200 | 1 | ND | 0 | ND | 0 |
| 21 | 0.32 | 2 | 1,100 | 1 | ND | 0 | ND | 0 |
| 22 | 0.52 | 2 | 1,600 | 1 | ND | 0 | ND | 0 |

TABLE B-continued

| | Method A | | | | Method B | | | |
|---|---|---|---|---|---|---|---|---|
| Ex. | GTPγS S1P$_1$ EC$_{50}$ (nM) | N | GTPγS S1P$_3$ EC$_{50}$ (nM) | N | GTPγS S1P$_1$ EC$_{50}$ (nM) | N | GTPγS S1P$_3$ EC$_{50}$ (nM) | N |
| 23 | 1.9 | 1 | 8,300 | 1 | ND | 0 | ND | 0 |
| 24 | 6.4 | 1 | 31,000 | 1 | ND | 0 | ND | 0 |
| 25 | 9.2 | 1 | 3,400 | 1 | ND | 0 | ND | 0 |
| Comp. A | 84 | 1 | 97 | 1 | 0.25 | 10 | 20 | 3 |

ND = not determined.
NC = a satisfactory dose response curve was not obtained.

The ratios of the GTPγS S1P$_3$ EC$_{50}$ values to the GTPγS S1P$_1$ EC$_{50}$ values, calculated from the data in Table B, are shown in Table C.

TABLE C

| Ex. | GTPγS S1P$_3$/S1P$_1$ (Method A) | GTPγS S1P$_3$/S1P$_1$ (Method B) |
|---|---|---|
| 1 | 1,400 | 11,000 |
| 2 | 2,100 | 4,600 |
| 3 | 1,300 | ND |
| 4 | 670 | ND |
| 5 | 320 | ND |
| 6 | 75 | ND |
| 7 | 560 | 5,400 |
| 8 | 140 | ND |
| 9 | 810 | 6,500 |
| 10 | 230 | ND |
| 11 | ND | 2,900 |
| 12 | ND | 11,000 |
| 13 | 578 | ND |
| 14 | 35 | ND |
| 15 | 175 | ND |
| 16 | 18 | ND |
| 17 | 27 | 112 |
| 18 | ND | 1,400 |
| 19 | 270 | ND |
| 20 | 3,900 | ND |
| 21 | 3,500 | ND |
| 22 | 3,000 | ND |
| 23 | 4,400 | ND |
| 24 | 4,900 | ND |
| 25 | 371 | ND |
| A | 1.2 | 78 |

In Table C, a larger value for the ratio of the GTPγS S1P$_3$ EC$_{50}$ value to the GTPγS S1P$_1$ EC$_{50}$ value indicates greater selectivity of S1P$_1$ activity over S1P$_3$ activity.

The compounds of the present invention, as exemplified by Examples 1 to 19, show the surprising advantage as agonists of S1P$_1$ and are selective over S1P$_3$. For example, as compared to Comparative Compound A, the exemplified compounds of the invention reported in Table C had selectivity ratios in the range of 18 to 4,900, while in contrast, Comparative Compound A had a selectivity ratio of 1.2, as measured by Method A. Exemplified compounds of the invention reported in Table C had selectivity ratios in the range of 112 to 11,000, while in contrast, Comparative Compound A had a selectivity ratio of 78, as measured by Method B.

The compounds of the present invention possess activity as agonists of S1P$_1$ and are selective over S1P$_3$, and thus may be used in treating, preventing, or curing various S1P$_1$ receptor-related conditions while reducing or minimizing the side effects due to S1P$_3$ activity. The surprising selectivity of the compounds of the present invention indicate their potential use in treating, preventing, or curing autoimmune and inflammatory diseases such as multiple sclerosis, rheumatoid arthritis, inflammatory bowel disease, or psoriasis, while reducing or minimizing possible cardiovascular side effects such as bradycardia and hypertension. Other potential uses of the compounds of the present invention include minimizing or reducing rejection of transplanted organs, while reducing or minimizing side effects due to S1P$_3$ activity.

Blood Lymphocyte Reduction Assay (BLR) in Rodents

Lewis rats or BALB/c mice were dosed orally with test article (as a solution or suspension in the vehicle) or vehicle alone (polyethylene glycol 300, "PEG300"). Blood was drawn at 4 hr and 24 h by retro-orbital bleeding. Blood lymphocyte counts were determined on an ADVIA® 120 Hematology Analyzer (Siemens Healthcare Diagnostics). The results were measured as a reduction in the percentage of circulating lymphocytes as compared to the vehicle treated group at the 4 hr and 24 hr measurement. The results represent the average results of all animals within each treatment group (n=3-4).

Examples 1 and 2 were tested in the Blood Lymphocyte Reduction assay (BLR) described hereinabove and the results are shown in Table D for rats and Table E for mice.

TABLE D

| Dose (mg/kg) | Example 1 % reduction in lymphocytes at 4 hr. | Example 1 % reduction in lymphocytes at 24 hr. | Example 2 % reduction in lymphocytes at 4 hr. | Example 2 % reduction in lymphocytes at 24 hr. |
|---|---|---|---|---|
| 0.03 | 75% | 45% | 70% | 56% |
| 0.3 | 82% | 73% | 80% | 79% |
| 1.0 | ND | ND | 84% | 85% |

TABLE E

| Dose (mg/kg) | Example 1 % reduction in lymphocytes at 4 hr. | Example 1 % reduction in lymphocytes at 24 hr. | Example 2 % reduction in lymphocytes at 4 hr. | Example 2 % reduction in lymphocytes at 24 hr. |
|---|---|---|---|---|
| 0.001 | 12% | 31% | −26% | 17% |
| 0.01 | 32% | 45% | −4% | 15% |
| 0.1 | 85% | 89% | 70% | 62% |
| 1.0 | 90% | 91% | 83% | 84% |

Rat Adjuvant Induced Arthritis Assay (AA)

Male Lewis rats (150-175 g; Harlan, n=8 treatment group) were immunized at the base of the tail with 100 nl of 10 mg/ml freshly ground *Mycobacterium butyricum* (Difco Laboratories) in incomplete Freund's adjuvant (sigma) Animals were dosed once daily with the test article (as a solution or suspension in the vehicle) or vehicle alone (polyethylene glycol 300, "PEG300") starting from the day of immunization. The volumes of their hind paws were measured in a water displacement plethysmometer (Ugo Basile, Italy). The baseline paw measurements were taken before onset of the disease (between day 7 to day 10). The paw measurements were then taken three times a week until the end of the study on day 20. All procedures involving animals were reviewed and approved by the Institutional Animal Care Use Committee.

Example 1 was tested in the Rat Adjuvant Induced Arthritis assay described hereinabove and the results are shown in Table F.

TABLE F

| Group | | Paw Swelling (mL) on Day 20 |
|---|---|---|
| Vehicle | Mean | 1.53 |
| | SD | 0.46 |
| Example 1 (0.03 mg/kg) | Mean | 1.39 |
| | SD | 0.52 |
| Example 1 (0.1 mg/kg) | Mean | 0.55 |
| | SD | 0.23 |
| Example 1 (0.5 mg/kg) | Mean | 0.23 |
| | SD | 0.09 |
| Example 1 (3.0 mg/kg) | Mean | 0.29 |
| | SD | 0.07 |

In the rat adjuvant—induced arthritis model, an animal model for rheumatoid arthritis, Example 1 inhibits disease progression as measured by paw swelling in the Lewis rat using a prophylactic oral dosing regiment.

Mouse Experimental Autoimmune Encephalomyelitis Assay (EAE)

Mice (C57BL/6 female, 6-8 weeks of age, Charles River, n=10-12 treatment group) were immunized subcutaneously with 150 µg $MOG_{35-55}$ emulsified 1:1 with incomplete Freund's adjuvant (sigma) supplemented with 150 µg *Mycobacterium tuberculosis* H37RA (Difco Laboratories). 400 ng of pertussis toxin (CalBiochem) was injected intraperitoneally on the day of immunization and two days later. Animals were dosed once daily with the test article (as a solution or suspension in the vehicle) or vehicle alone (polyethylene glycol 300, "PEG300") starting from 1 day after immunization. Clinical scoring and body weight were taken 3 times per week until the end of the study on day 24. Clinical scoring system: 0.5: partial tail weakness; 1: limp tail or waddling gait with tail tonicity; 1.5: waddling gait with partial tail weakness; 2: waddling gait with limp tail (ataxia); 2.5: ataxia with partial limb paralysis; 3: full paralysis of one limb; 3.5: full paralysis of one limbs with partial paralysis of a second limb; 4: full paralysis of two limbs; 4.5: moribund; 5: death.

Example 1 was tested in the Mouse Experimental Autoimmune Encephalomyelitis assay described hereinabove and the results are shown in Table G.

TABLE G

| | | Clinical Score on day 21 |
|---|---|---|
| Vehicle | Mean | 2.79 |
| | SD | 1.30 |
| Example 1 (0.02 mg/kg) | Mean | 1.75 |
| | SD | 0.26 |
| Example 1 (0.2 mg/kg) | Mean | 1.13 |
| | SD | 0.61 |
| Example 1 (2.0 mg/kg) | Mean | 1.15 |
| | SD | 0.24 |

In the mouse experimental autoimmune encephalomyelitis (EAE) model, an animal model for multiple sclerosis, Example 1 inhibits disease progression as determined by the clinical scores in C57Bl/6 mice using a prophylactic oral dosing regiment.

What is claimed is:

1. A compound of Formula (I):

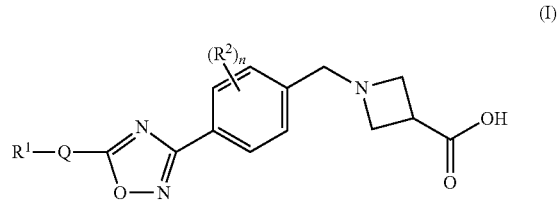

(I)

or a pharmaceutically acceptable salt thereof, wherein:
Q is

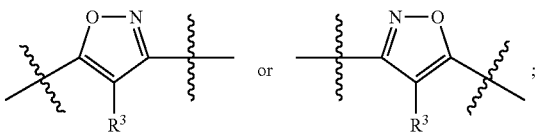

n is zero or an integer selected from 1 through 4;
$R^1$ is alkyl or aryl, said aryl optionally substituted with one to five substituents independently selected from $C_1$ to $C_6$ alkyl, $C_1$ to $C_4$ haloalkyl, —$OR^4$, and/or halogen;
each $R^2$ is independently selected from $C_1$ to $C_6$ alkyl, $C_1$ to $C_4$ haloalkyl, —$OR^4$, and/or halogen;
$R^3$ is hydrogen, alkyl, cycloalkyl, haloalkyl, —C(O)$OR^5$, —C(O)$NR_aR_b$, or aryl, said aryl optionally substituted with one to five substituents independently selected from $C_1$ to $C_6$ alkyl, $C_1$ to $C_4$ haloalkyl, —$OR^4$, and/or halogen;
each $R^4$ is independently selected from $C_1$ to $C_6$ alkyl, $C_1$ to $C_4$ haloalkyl, and/or benzyl;
$R^5$ is hydrogen, alkyl, or benzyl; and
$R_a$ and $R_b$ are independently selected from hydrogen, alkyl, haloalkyl, and/or benzyl.

2. The compound of claim 1 or a pharmaceutically acceptable salt thereof, wherein:
Q is

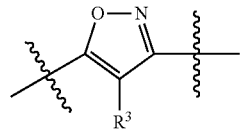

3. The compound of claim 1 or a pharmaceutically acceptable salt thereof, wherein:
Q is

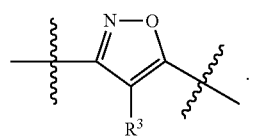

4. The compound of claim 1 or a pharmaceutically acceptable salt thereof, wherein:
$R_1$ is aryl optionally substituted with one to five substituents independently selected from $C_1$ to $C_6$ alkyl, $C_1$ to $C_4$ haloalkyl, —$OR^4$, and/or halogen.

5. The compound of claim 1 or a pharmaceutically acceptable salt thereof, wherein:
- $R^1$ is phenyl optionally substituted with one to five substituents independently selected from $C_1$ to $C_6$ alkyl, $C_1$ to $C_4$ haloalkyl, —$OR^4$, and/or halogen;
- $R^3$ is $C_1$ to $C_6$ alkyl, $C_1$ to $C_4$ haloalkyl, $C_3$ to $C_6$ cycloalkyl, —$C(O)OR^5$, —$C(O)NR^aR^b$, or phenyl optionally substituted with one to five substituents independently selected from $C_1$ to $C_6$ alkyl, $C_1$ to $C_4$ haloalkyl, —$OR^4$, and/or halogen;
- $R^5$ is hydrogen or $C_1$ to $C_6$ alkyl; and
- $R^a$ and $R^b$ are independently selected from hydrogen, $C_1$ to $C_6$ alkyl, and/or $C_1$ to $C_4$ haloalkyl.

6. The compound of claim 5 or a pharmaceutically acceptable salt thereof, wherein:
- n is zero or 1;
- $R^1$ is phenyl;
- $R^2$ is halogen;
- $R^3$ is $C_1$ to $C_4$ alkyl, cyclopropyl, phenyl, —$CF_3$, —$CF_2H$, —$(CH_2)_2CF_3$, —$CF_2CH_3$, —$CF_2CH_2CH_3$, —$C(O)NHR^a$, or —$C(O)OR^5$;
- $R^5$ is hydrogen or methyl; and
- $R^a$ is methyl or 2,2,2-trifluoroethyl.

7. The compound of claim 1 or a pharmaceutically acceptable salt thereof, wherein:
- $R^1$ is alkyl.

8. The compound of claim 1 or a pharmaceutically acceptable salt thereof, wherein:
- n is zero;
- $R^1$ is $C_1$ to $C_6$ alkyl; and
- $R^3$ is $C_1$ to $C_6$ alkyl.

9. The compound of claim 1 or a pharmaceutically acceptable salt thereof, selected from the group consisting of:
- 1-(4-(5-(3-phenyl-4-(trifluoromethyl)isoxazol-5-yl)-1,2,4-oxadiazol-3-yl)benzyl)azetidine-3-carboxylic acid;
- 1-(4-(5-(5-phenyl-4-(trifluoromethyl)isoxazol-3-yl)-1,2,4-oxadiazol-3-yl)benzyl)azetidine-3-carboxylic acid;
- 1-(4-(5-(4-butyl-5-phenylisoxazol-3-yl)-1,2,4-oxadiazol-3-yl)benzyl)azetidine-3-carboxylic acid;
- 1-(4-(5-(4-isobutyl-5-phenylisoxazol-3-yl)-1,2,4-oxadiazol-3-yl)benzyl)azetidine-3-carboxylic acid;
- 1-(4-(5-(4-ethyl-5-phenylisoxazol-3-yl)-1,2,4-oxadiazol-3-yl)benzyl)azetidine-3-carboxylic acid;
- 1-(4-(5-(4-cyclopropyl-5-phenylisoxazol-3-yl)-1,2,4-oxadiazol-3-yl)benzyl)-azetidine-3-carboxylic acid, 2,2,2-trifluoroacetic acid salt;
- 1-(4-(5-(4-tert-butyl-5-phenylisoxazol-3-yl)-1,2,4-oxadiazol-3-yl)benzyl)-azetidine-3-carboxylic acid;
- 1-(4-(5-(5-phenyl-4-(3,3,3-trifluoropropyl)isoxazol-3-yl)-1,2,4-oxadiazol-3-yl)benzyl)azetidine-3-carboxylic acid;
- 1-(4-(5-(4-(1,1-difluoroethyl)-5-phenylisoxazol-3-yl)-1,2,4-oxadiazol-3-yl)benzyl)azetidine-3-carboxylic acid;
- 1-(4-(5-(4-(1,1-difluoropropyl)-5-phenylisoxazol-3-yl)-1,2,4-oxadiazol-3-yl)benzyl)azetidine-3-carboxylic acid;
- 1-(4-(5-(3-phenyl-4-propylisoxazol-5-yl)-1,2,4-oxadiazol-3-yl)benzyl)azetidine-3-carboxylic acid;
- 1-(4-(5-(4-(difluoromethyl)-3-phenylisoxazol-5-yl)-1,2,4-oxadiazol-3-yl)benzyl)azetidine-3-carboxylic acid;
- 1-(4-(5-(4-(methoxycarbonyl)-3-phenylisoxazol-5-yl)-1,2,4-oxadiazol-3-yl)benzyl)azetidine-3-carboxylic acid;
- 1-(4-(5-(4-(methylcarbamoyl)-3-phenylisoxazol-5-yl)-1,2,4-oxadiazol-3-yl)benzyl)azetidine-3-carboxylic acid;
- 1-(4-(5-(3-phenyl-4-(2,2,2-trifluoroethylcarbamoyl)isoxazol-5-yl)-1,2,4-oxadiazol-3-yl)benzyl)azetidine-3-carboxylic acid;
- 5-(3-(4-((3-carboxyazetidin-1-yl)methyl)phenyl)-1,2,4-oxadiazol-5-yl)-3-phenylisoxazole-4-carboxylic acid;
- 1-(4-(5-(4,5-diphenylisoxazol-3-yl)-1,2,4-oxadiazol-3-yl)benzyl)azetidine-3-carboxylic acid;
- 1-(4-(5-(5-isobutyl-4-propylisoxazol-3-yl)-1,2,4-oxadiazol-3-yl)benzyl)azetidine-3-carboxylic acid;
- 1-(4-(5-(4-isobutyl-5-propylisoxazol-3-yl)-1,2,4-oxadiazol-3-yl)benzyl)azetidine-3-carboxylic acid.

10. A composition comprising a compound according to claim 1 or a pharmaceutically acceptable salt thereof, and a pharmaceutically acceptable carrier.

11. A method of treating a disease or disorder associated with the activity of G protein-coupled receptor $S1P_1$, the method comprising administering to a mammalian patient having said disease or disorder a compound according to claim 1 or a pharmaceutically acceptable salt thereof wherein said disease or disorder is selected from the group consisting of bone marrow, organ or transplant rejection, systemic lupus erythematosis, chronic rheumatoid arthritis, type I diabetes mellitus, inflammatory bowel disease, biliary cirrhosis, uveitis, multiple sclerosis, Crohn's disease, ulcerative colitis, bullous pemphigoid, sarcoidosis, psoriasis, autoimmune myositis, Wegener's granulomatosis, ichthyosis, Graves' ophthalmopathy and asthma.

12. A method of treating a chronic inflammatory disease, the method comprising administering to a mammalian patient having said chronic inflammatory disease a compound according to claim 1 or a pharmaceutically acceptable salt thereof.

* * * * *

UNITED STATES PATENT AND TRADEMARK OFFICE
CERTIFICATE OF CORRECTION

PATENT NO. : 8,354,398 B2
APPLICATION NO. : 13/145730
DATED : January 15, 2013
INVENTOR(S) : Scott Watterson et al.

It is certified that error appears in the above-identified patent and that said Letters Patent is hereby corrected as shown below:

In the Claims:

Claim 4, col. 120, line 65, delete "$R_1$" and insert -- $R^1$ --, therefor; and Claim 9, col. 122, line 24, after "acid;" insert -- and --.

Signed and Sealed this
Twenty-fourth Day of September, 2013

Teresa Stanek Rea
*Deputy Director of the United States Patent and Trademark Office*